(12) United States Patent
Owens et al.

(10) Patent No.: US 12,378,539 B2
(45) Date of Patent: Aug. 5, 2025

(54) EVOLVED INTEGRASES AND METHODS OF USING THE SAME FOR GENOME EDITING

(71) Applicant: University of Hawaii, Honolulu, HI (US)

(72) Inventors: Jesse B. Owens, Honolulu, HI (US); Brian Hew, Honolulu, HI (US)

(73) Assignee: University of Hawaii, Honolulu, HI (US)

( * ) Notice: Subject to any disclaimer, the term of this patent is extended or adjusted under 35 U.S.C. 154(b) by 0 days.

(21) Appl. No.: 18/915,656

(22) Filed: Oct. 15, 2024

(65) Prior Publication Data

US 2025/0043263 A1 Feb. 6, 2025

Related U.S. Application Data

(63) Continuation of application No. PCT/US2024/035414, filed on Jun. 25, 2024.

(60) Provisional application No. 63/592,945, filed on Oct. 25, 2023, provisional application No. 63/510,171, filed on Jun. 26, 2023.

(51) Int. Cl.
*C12N 9/22* (2006.01)

(52) U.S. Cl.
CPC ...................... *C12N 9/22* (2013.01)

(58) Field of Classification Search
CPC ........................................ C12N 9/22
See application file for complete search history.

(56) References Cited

U.S. PATENT DOCUMENTS

| | | | |
|---|---|---|---|
| 6,187,994 B1 | 2/2001 | Baszczynski et al. | |
| 6,890,726 B1 | 5/2005 | Sauer et al. | |
| 7,732,585 B2 | 6/2010 | Calos | |
| 8,940,533 B2 | 1/2015 | Oshimura et al. | |
| 9,023,594 B2 | 5/2015 | Liu et al. | |
| 9,394,537 B2 | 7/2016 | Liu et al. | |
| 9,691,017 B2 | 6/2017 | Lu et al. | |
| 9,765,352 B2 | 9/2017 | Gordon-Kamm et al. | |
| 9,771,574 B2 | 9/2017 | Liu et al. | |
| 9,816,077 B2 | 11/2017 | Kolot et al. | |
| 9,932,607 B2 | 4/2018 | Calos et al. | |
| 10,081,817 B2 | 9/2018 | Padidam | |
| 10,336,997 B2 | 7/2019 | Liu et al. | |
| 10,344,301 B2 | 7/2019 | Ghadessy et al. | |

(Continued)

FOREIGN PATENT DOCUMENTS

| | | |
|---|---|---|
| CN | 116004586 A | 4/2023 |
| EP | 4133086 A1 | 2/2023 |

(Continued)

OTHER PUBLICATIONS

UniProt ID A0A2P1N3E5_9CAUD, https://www.uniprot.org/uniprotkb/A0A2P1N3E5/entry (Year: 2018).*

(Continued)

*Primary Examiner* — Louise W Humphrey
*Assistant Examiner* — Rachel Emily Martin
(74) *Attorney, Agent, or Firm* — Morgan, Lewis & Bockius LLP

(57) ABSTRACT

Disclosed are evolved Bxb1 and PhiC31 integrases that exhibit increased insertion activity and efficiency as compared to their wild-type counterparts and use of the evolved integrases to modify any sequence within the genome of a cell or subject.

16 Claims, 10 Drawing Sheets

Specification includes a Sequence Listing.

(56) References Cited

U.S. PATENT DOCUMENTS

| | | |
|---|---|---|
| 10,392,674 B2 | 8/2019 | Liu et al. |
| 10,480,009 B2 | 11/2019 | Lu et al. |
| 10,731,153 B2 | 8/2020 | Weiss et al. |
| 11,030,531 B2 | 6/2021 | Wong et al. |
| 11,104,967 B2 | 8/2021 | Liu et al. |
| 11,214,792 B2 | 1/2022 | Liu et al. |
| 11,492,613 B2 | 11/2022 | Farruggio et al. |
| 11,591,604 B2 | 2/2023 | Lu et al. |
| 11,827,881 B2 | 11/2023 | Abudayyeh et al. |
| 11,905,623 B2 | 2/2024 | Liu et al. |
| 11,912,985 B2 | 2/2024 | Liu et al. |
| 11,946,054 B2 | 4/2024 | Shah et al. |
| 11,959,093 B2 | 4/2024 | Kong et al. |
| 12,129,480 B2 | 10/2024 | Ng et al. |
| 2006/0046294 A1 | 3/2006 | Ow et al. |
| 2006/0172377 A1 | 8/2006 | Padidam |
| 2008/0020465 A1 | 1/2008 | Padidam |
| 2008/0241116 A1 | 10/2008 | Calos |
| 2010/0086532 A1 | 4/2010 | Barbas, III et al. |
| 2011/0136237 A1 | 6/2011 | Ow et al. |
| 2012/0141441 A1 | 6/2012 | Calos et al. |
| 2015/0275232 A1 | 10/2015 | Padidam |
| 2016/0145645 A1 | 5/2016 | Bahr et al. |
| 2019/0169634 A1 | 6/2019 | Lu et al. |
| 2020/0255844 A1 | 8/2020 | Kosuri et al. |
| 2020/0370067 A1 | 11/2020 | Monnat, Jr. et al. |
| 2021/0002669 A1 | 1/2021 | Ng et al. |
| 2021/0123065 A1 | 4/2021 | Murphy et al. |
| 2021/0309988 A1 | 10/2021 | Sealover et al. |
| 2022/0025406 A1 | 1/2022 | Bachiller Perez et al. |
| 2022/0127642 A1 | 4/2022 | Tsai et al. |
| 2022/0139496 A1 | 5/2022 | Kemble et al. |
| 2022/0195465 A1 | 6/2022 | Bahr et al. |
| 2022/0369610 A1 | 11/2022 | Wiles et al. |
| 2023/0287441 A1 | 9/2023 | Abudayyeh et al. |
| 2023/0340467 A1 | 10/2023 | Liu et al. |
| 2023/0383274 A1 | 11/2023 | Abudayyeh et al. |
| 2024/0084291 A1 | 3/2024 | Munding et al. |
| 2024/0093210 A1 | 3/2024 | Jõers et al. |
| 2024/0240156 A1 | 7/2024 | Shen et al. |
| 2024/0263153 A1 | 8/2024 | Rubens et al. |
| 2024/0263183 A1 | 8/2024 | Shah et al. |
| 2024/0271161 A1 | 8/2024 | Rubio et al. |

FOREIGN PATENT DOCUMENTS

| | | |
|---|---|---|
| EP | 4380969 A1 | 6/2024 |
| WO | WO2021102390 | 5/2021 |
| WO | WO2021226558 | 7/2021 |
| WO | WO2021220020 A1 | 11/2021 |
| WO | WO2022251356 | 12/2022 |
| WO | WO2023070031 | 4/2023 |
| WO | WO2023076898 A1 | 5/2023 |
| WO | WO2023116929 A1 | 6/2023 |
| WO | WO2023147507 | 8/2023 |
| WO | WO2024026378 A2 | 2/2024 |
| WO | WO2024138194 A1 | 6/2024 |
| WO | WO2024155830 A2 | 7/2024 |
| WO | WO2024168147 A2 | 8/2024 |
| WO | WO2024170866 A1 | 8/2024 |

OTHER PUBLICATIONS

Jusniak et al., Comparison of Integrases Identifies Bxb1-GA Mutant as the Most Efficient Site-Specific Integrase System in Mammalian Cells. ACS Synth Biol. Jan. 18, 2019;8(1):16-24. doi: 10.1021/acssynbio.8b00089. Epub Jan. 9, 2019. PMID: 30609349. ( Year: 2019).*

International Search Report & Written Opinion PCT Application No. PCT/US2024/035414, dated Jan. 10, 2025, 19 pages.

Birling, et al., "Site-specific recombinases for manipulation of the mouse genome", Methods Mol Biol. 2009; 561:245-63.

Fogg, et al., "New applications for phage integrases", J Mol Biol. Jul. 2014. 29; 426(15):2703.

Gopaul, et al., "Structure and mechanism in site-specific recombination", Curr Opin Struct Biol. Feb. 1999; 9(1):14-20.

Grainge, et al., "The integrase family of recombinase: organization and function of the active site", Mol Microbiol. Aug. 1999; 33(3):449-56.

Grindley, et al., "Mechanisms of site-specific recombination", Annu Rev Biochem. 2006; 75:567-605.

Smith, et al., "Diversity in the serine recombinases", Mol Microbiol. Apr. 2002; 44(2):299-307.

Smith, et al., "Site-specific recombination by phiC31 integrase and other large serine recombinases", Biochem Soc Trans. Apr. 2010; 38(2):388-94.

Albert et al., Site-specific integration of DNA into wild-type and mutant lox sites placed in the plant genome, (1995) *The Plant Journal*, 7:649-659.

Anzalone, et al., "Programmable deletion, replacement, integration and inversion of large DNA sequences with twin prime editing," (2022) *Nature Biotechnology*, 40:731-740.

Badran et al., "Continuous evolution of *B. thuringiensis* toxins overcomes insect resistance," (2016) *Nature* 533(7601): 58-63.

Balabaskaran-Nina, et al., "Diverse target gene modifications in Plasmodium falciparum using Bxb1 integrase and an intronic attB", Parasit & Vectors. Oct. 17, 2018;11(1):548. doi: 10.1186/s13071-018-3129-5.

Chalberg et al., "Integration Specificity of Phage ΦC31 Integrase in the Human Genome," (2006) *J. Mol. Biol.* 357(1): 28-48.

Chen et al., "Enhanced prime editing systems by manipulating cellular determinants of editing outcomes," (2021) *Cell* 184:5635-5652.

Doman et al., "Designing and executing prime editing experiments in mammalian cells," (2022) *Nat. Protoc.* 17(11): 2431-2468.

Durrant, et al., "Systematic discovery of recombinases for efficient integration of large DNA sequences into the human genome", Nature Biotechnology. Apr. 2023;41(4):488-499. doi: 10.1038/s41587-022-01494-w. Epub Oct. 10, 2022.

Erhardt, et al., "Protocol for large DNA transgenesis in mice using the Cas9+Bxb1 toolbox" Cell Press (2024).

Esvelt et al., "A System for the Continuous Directed Evolution of Biomolecules," (2011) *Nature* 472(7344): 499-503.

Fauser, et al., "Systematic Development of Reprogrammed Modular Integrases Enables Precise Genomic Integration of Large DNA Sequences," bioRxiv [preprint publication], May 10, 2024, doi: https://doi.org/10.1101/2024.05.09.593242.

Gaidukov, et al., "A multi-landing pad DNA integration platform for mammalian cell engineering", Nucleic Acids Res. May 4, 2018;46(8):4072-4086. doi: 10.1093/nar/gky216.

Ghanbari, et al., "Targeted integration in CHO cells using CRISPITCh/Bxb1 recombinase-mediated cassette exchange hybrid system", Appl Microbiol Biotechnol. Feb. 2023;107(2-3):769-783. doi: 10.1007/s00253-022-12322-1. Epub Dec. 20, 2022.

Ghosh et al., "The Orientation of Mycobacteriophage Bxb1 Integration Is Solely Dependent on the Central Dinucleotide of attP and attB," (2003) *Mol. Cell* 12(5): 1101-11.

Groth, at al., "A phage integrase directe efficient site-specific integration in human cells," (2000) *Proc. Natl. Acad. Sci. USA* 97(11): 5995-6000.

Hew, et al., "Directed evolution of hyperactive integrases for site specific insertion of transgenes," bioRxiv [preprint publication], Jun. 11, 2024, doi: https://doi.org/10.1101/2024.06.10.598370.

Hosur, et al., "Programmable RNA-Guided Large DNA Transgenesis by CRISPR/Cas9 and Site-Specific Integrase Bxb1", Front Bioeng Biotechnol. Jul. 5, 2022;10:910151. doi: 10.3389/fbioe.2022.910151. eCollection 2022.

Hou, et al., "An open-source system for in planta gene stacking by Bxb1 and Cre recombinases", Mol Plant. Dec. 2014;7(12):1756-65. doi: 10.1093/mp/ssu107. Epub Oct. 3, 2014.

Huhtinen, et al., "Increased stable integration efficiency in CHO cells through enhanced nuclear localization of Bxb1 serine integrase", BMC Biotechnology (2024).

(56) References Cited

OTHER PUBLICATIONS

Inniss, et al., "A novel Bxb1 integrase RMCE system for high fidelity site-specific integration of mAb expression cassette in CHO Cells", Biotechnol Bioeng. Aug. 2017;114(8):1837-1846. doi: 10.1002/bit.26268. Epub Mar. 14, 2017.

Irion et al., "Identification and targeting of the ROSA26 locus in human embryonic stem cells," (2007) *Nat. Biotechnol.* 25(12): 1477-1482.

Jost et al., "Titrating gene expression using libraries of systematically attenuated CRISPR guide RNAs," (2020) *Nat. Biotechnol.* 38(3):355-364.

Jusiak, et al., "Comparison of Integrases Identifies Bxb1-GA Mutant as the Most Efficient Site-Specific Integrase System in Mammalian Cells", ACS Synth Biol. Jan. 18, 2019;8(1):16-24. doi: 10.1021/acssynbio.8b00089. Epub Jan. 9, 2019.

Keenholtz, et al., "Crossover-site sequence and DNA torsional stresscontrol strand interchanges by the Bxb1 site-specific serine recombinase", Nucleic Acids Research, 2016, vol. 44, No. 18, 8921-8932. Aug. 22, 2016.

Keravala et al., "Mutational Derivatives of PhiC31 Integrase With Increased Efficiency and Specificity," (2009) *Mol. Ther.* 17(1):112-20.

Low, et al., "Efficient targeted transgenesis of large donor DNA into multiple mouse genetic backgrounds using bacteriophage Bxb1 integrase", Sci Rep. Jul. 20, 2023;13(1):11756. doi: 10.1038/s41598-023-39015-7.

Miller et al., "Phase-assisted continuous and non-continuous evolution," (2020) *Nat. Protoc.* 15(12): 4101-4127.

Nelson et al., "Engineered pegRNAs improve prime editing efficiency," (2022) *Nat. Biotechnol.* 40(3): 402-410.

Oceguera-Yanez et al., "Engineering the AAVS1 locus for consistent and scalable transgene expression in human iPSCs and their differentiated derivatives," (2016) *Methods* 101:43-55.

Pandey, et al., "Efficient site-specific integration of large genes in mammalian cells via continuously evolved recombinases and prime editing", Nature Biomedical Engineering, Jun. 10, 2024.

Roelle, et al., "Mammalian Genomic Manipulation with Orthogonal Bxb1 DNA Recombinase Sites for the Functional Characterization of Protein Variants", ACS Synth Biol. Nov. 17, 2023;12(11):3352-3365. doi: 10.1021/acssynbio.3c00355. Epub Nov. 3, 2023.

Shao, et al., "Precise excision of plastid DNA by the large serine recombinase Bxb1", Plant Biotechnol J. Apr. 2014;12(3):322-9. doi: 10.1111/pbi.12139. Epub Nov. 22, 2013.

Tomimatsu, et al., "Multiple expression cassette exchange via TP901-1, R4, and Bxb1 integrase systems on a mouse artificial chromosome", FEBS Press (2017).

Voutev, et al., "Bxb1 phage recombinase assists genome engineering in Drosophila melanogaster", Biotechniques. Jan. 1, 2017;62(1):37-38. doi: 10.2144/000114494.

Voziyanov et al. "A dual reporter screening system identified the amino acid at position 82 in Flp site-specific recombinase as a determinat for target specificity," (2002) *Nucleic Acid Research* 30:7.

Wang, et al., "Bxb1 integrase serves as a highly efficient DNA recombinase in rapid metabolite pathway assembly", Acta Biochim Biophys Sin (Shanghai). Jan. 2017;49(1):44-50. doi: 10.1093/abbs/gmw115. Epub Nov. 17, 2016.

Wang, et al., "Efficient targeted insertion of large DNA fragments without DNA donors," (2022) *Nat Methods* 19(3): 331-340.

Wilkins et al., "Ultraplex: A rapid, flexible, all-in-one fastq demultiplexer," (2021) *Wellcome Open Res.* 6:141.

Yarnall et al., "Drag-and-drop genome insertion of large sequences without double-strand DNA cleavage using CRISPR-directed integrases," (2023) *Nat. Biotechnol.* 41(4): 500-512.

Yu et al., "Highly Efficient Transgenesis in Ferrets Using CRISPR/Cas9-Mediated Homology-Independent Insertion at the ROSA26 Locus," (2019) Nature Scientific Reports, 9:1971.

Zhu, et al., "DICE, an efficient system for iterative genomic editing in human pluripotent stem cells", Nucleic Acids Research, vol. 42, No. 5. e34. Dec. 4, 2013.

* cited by examiner

EVOLVED INTEGRASES AND METHODS OF USING THE SAME FOR GENOME EDITING

This application is a bypass Continuation Application under 35 U.S.C. § 111 of International Application No. PCT/US2024/035414, filed Jun. 25, 2024, which claims benefit from and priority to U.S. Provisional Patent Application Ser. Nos. 63/510,171, filed Jun. 26, 2023, and 63/592,945, filed Oct. 25, 2023, the contents of which are incorporated herein by reference in their entireties.

This invention was made with government support under grant nos. GM103457, GM132779, GM125526 and EB031124 awarded by the National Institutes of Health. The government has certain rights in this invention.

INTRODUCTION

Statement Regarding Electronic Filing of a Sequence Listing

A Sequence Listing in XML format, entitled "138774-5004_Sequence_Listing.XML," that is approximately 342,971 bytes in size, generated Oct. 8, 2024, and filed herewith, is hereby incorporated by reference into the specification.

BACKGROUND

Many genetic diseases arise from disparate mutations differing from one patient to the next. For a common therapy to be effective, a full replacement of the coding sequence is often needed. As treatments for increasingly complex diseases are undertaken, multi-gene insertions will be necessary requiring larger cargos beyond the limits of current virus-based approaches. While a multitude of genetic edits are now possible through the use of CRISPR nuclease-induced non-homologous end-joining (NHEJ; deletion) and homology-directed repair (HDR; insertion), base editing (single base pair replacement), or prime editing (small insertion, replacement, or deletion), notably HDR insertion efficiency drops significantly for larger cargos and HDR is inefficient or nonfunctional in non-dividing cells which make up most therapeutically relevant cell types. NHEJ-based insertion methods exist but are generally inefficient and, like HDR, rely on unprotected double-strand breaks that can cause uncontrolled large deletions or chromosomal rearrangements. prime editing functions in both dividing and non-dividing cells and efficiently inserts sequences <50 base pairs while minimizing double stranded breaks. An improved version or prime editing, referred to as twin prime editing, has been developed, which uses the attachment (att) site from Bxb1 to insert cargos as large as 5.6 kb at the att site (Anzalone et al. (2022) *Nat. Biotechnol.* 40:731-740). This approach overcomes many of the hurdles of current gene insertion tools and holds great promise for correcting genetic diseases.

Nevertheless, there remains a need in the art to improve the efficiency of integrase-mediated integration. The present disclosure addresses this need in the art.

SUMMARY

In one aspect is provided an evolved Bxb1 integrase comprising an amino acid sequence that is at least 90% identical to the amino acid sequence of SEQ ID NO:1, wherein the amino acid sequence of the evolved Bxb1 integrase comprises one or more mutations and exhibits at least a 2-fold increase in integration of exogenous nucleic acids into a genomic target site as compared to wild-type Bxb1 integrase In another aspect, an evolved PhiC31 integrase is provided that comprises an amino acid sequence that is at least 90% identical to the amino acid sequence of SEQ ID NO:2, wherein the amino acid sequence of the evolved PhiC31 integrase comprises at least one mutation as described herein.

Also provided herein is a method of altering the sequence of a genome of a cell by contacting a cell with the evolved Bxb1 or PhiC31 integrase of the disclosure, wherein the cell includes in its genome at least one integrase recognition sequence recognized by the evolved integrase so that the evolved integrase binds to the integrase recognition sequence and alters the sequence of the genome of the cell.

DETAILED DESCRIPTION

Figure 1:
FIG. 1. Amplicon sequencing comparison of twin prime editing using dual epegRNA at target sites AAVS1, Xq22.1, and human ROSA26 in HEK293 cells. Mean and s.d. bars represent 2 biological replicates transfected on separate days.

Serine integrases such as PhiC31 and Bxb1 enable the insertion of large DNA cargos at attachment (att) sites. By targeting att sites to the genome using technologies such as prime editing (PE), integrases can deliver cargo to safe loci while avoiding double-strand breaks. Phage-assisted continuous evolution (PACE) was used to evolve the PhiC31 and Bxb1 serine integrases to increase their activity on their respective native attachment (att) sequence. The resulting sequence of the improved integrases was subcloned into mammalian expression vectors and tested for activity of insertion of large transgenes into the human genome of cell lines. The att site that each integrase uses for insertion was first inserted into the genome using twin prime editing. Next, each integrase inserted cargo DNA into the att site at a specific location in the genome. The efficiency was accurately measured using droplet digital PCR. During pre-optimized transfection conditions without sorting for transfected cells, the wild-type integrase inserted its cargo DNA at 3.7% of the haploid genomes. By comparison, the evolved integrases inserted their cargo DNA into up to 21.9% of haploid genomes. During optimized transfection conditions using cells sorted for complete transfection, the wild-type integrase inserted its cargo DNA at 32% of the haploid genomes. By comparison, the evolved integrases inserted their cargo DNA into up to 80% of haploid genomes following sorting. The improved integrases find use in replacing defective genes in the genome. By directing insertion to specific sites in the genome, the risk of off-target insertion and insertional mutagenesis is significantly reduced. The increase in efficiency afforded by the improved integrases described herein will dramatically improve the effectiveness of this technology as a therapy for treating a disease or disorder for which altering the sequence of a gene will provide a benefit.

Accordingly, some aspects provide evolved integrases that exhibit increased insertion activity and efficiency as compared to their wild-type counterparts and use of the evolved integrases to modify, for example, any sequence within the genome of a cell or subject. In particular, evolved Bxb1 or PhiC31 integrases are described that exhibit an increase in insertion efficiency as compared to wild-type Bxb1 or PhiC31 integrase. The term "wild-type (or native) integrase" refers to an integrase that is naturally occurring and/or has not been modified through human intervention.

The evolved Bxb1 and PhiC31 integrases described herein have at least one mutation, or at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, or at least 20 mutations. Mutations may include substitutions, deletions, or insertions without eliminating recombinase activity.

A wild-type Bxb1 integrase may have the following amino acid sequence:

```
                                        (SEQ ID NO: 1)
MRALVVIRLSRVTDATTSPERQLESCQQLCAQRGWDVVGVAEDLD

VSGAVDPFDRKRRPNLARWLAFEEQPFDVIVAYRVDRLTRSIRHL

QQLVHWAEDHKKLVVSATEAHFDTTTPFAAVVIALMGTVAQMELE

AIKERNRSAAHFNIRAGKYRGSLPPWGYLPTRVDGEWRLVPDPVQ

RERILEVYHRVVDNHEPLHLVAHDLNRRGVLSPKDYFAQLQGREP

QGREWSATALKRSMISEAMLGYATLNGKTVRDDDGAPLVRAEPIL

TREQLEALRAELVKTSRAKPAVSTPSLLLRVLFCAVCGEPAYKFA
```

-continued
```
GGGRKHPRYRCRSMGFPKHCGNGTVAMAEWDAFCEEQVLDLLGDA

ERLEKVWVAGSDSAVELAEVNAELVDLTSLIGSPAYRAGSPQREA

LDARIAALAARQEELEGLEARPSGWEWRETGQRFGDWWREQDTAA

KNTWLRSMNVRLTFDVRGGLTRTIDFGDLQEYEQHLRLGSVVERL

HTGMS.
```

In one aspect is provided an evolved Bxb1 integrase having an amino acid sequence that is at least 70%, at least 80%, at least 90%, at least 95%, at least 97%, at least 98% or at least 99% identical to the amino acid sequence of SEQ ID NO:1, wherein the evolved Bxb1 integrase has at least one mutation and exhibits an increase in insertion efficiency as compared to wild-type Bxb1 integrase. In some aspects, the evolved Bxb1 integrase has between one and 8 mutations, e.g., between one and 3 mutations, between 2 and 4 mutations, between 3 and 5 mutations, between 4 and 6 mutations, between 5 and 7 mutations, between 6 and 8 mutations, between 2 and 7 mutations or between 4 and 8 mutations as compared to the wild-type Bxb1 integrase (e.g., SEQ ID NO:1). In other aspects, the evolved Bxb1 integrase has at least one mutation, at least 2 mutations, at least 3 mutations, at least 4 mutations, at least 5 mutations, at least 6 mutations, at least 7 mutations or at least 8 mutations as compared to the wild-type Bxb1 integrase (e.g., SEQ ID NO:1).

In further aspects, the evolved Bxb1 integrase has at least one mutation, the at least one mutation being at position 4, 5, 18, 24, 34, 36, 40, 42, 45, 46, 49, 50, 51, 57, 61, 62, 63, 67, 69, 70, 74, 75, 76, 79, 85, 87, 88, 89, 90, 92, 95, 99, 100, 105, 106, 110, 111, 119, 122, 130, 133, 137, 140, 145, 153, 156, 160, 164, 166, 168, 174, 175, 178, 179, 181, 187, 189, 191, 194, 203, 209, 218, 223, 229, 231, 239, 248, 251, 254, 261, 263, 264, 268, 272, 278, 280, 281, 282, 283, 285, 287, 288, 292, 295, 302, 306, 307, 311, 313, 319, 321, 328, 331, 332, 333, 334, 341, 347, 353, 355, 359, 360, 361, 362, 366, 369, 370, 375, 380, 387, 388, 397, 398, 405, 409, 411, 414, 415, 416, 419, 425, 426, 428, 434, 435, 444, 445, 453, 461, 463, 466, 468, 476, 479, 480, 483, 484, 487, 488, 489, 494, 496, and/or 499 relative to SEQ ID NO:1. In some aspects, the evolved Bxb1 integrase has at least one mutation, the at least one mutation being L4I, V5V, S18S, E24E, G34D, D36A, D36N, V40I, V40A, V40V, E42K, D45G, V46V, A49S, V50I, D51D, D51N, D51G, D51E, R57K, L61F, A62A, R63K, F67S, E69A, E69E, Q70H, V74, I75V, V76I, R79R, R85R, I87L, I87V, R88R, H89G, H89Y, L90L, Q92H, Q92Q, H95Y, D99N, H100N, H100H, V105A, S106S, A110A, H111P, A119S, V122M, A130A, E133E, I137I, R140R, A145T, K153K, G156P, P160P, L164L, T166I, V168I, L174L, V175V, V175A, P178P, V179A, V179I, R181K, R181R, V187I, V187V, H189N, H189Y, Q191Q, N194D, H203Y, G209G, A218A, R223R, E229K, S231S, M239I, A248T, N251K, N251N, T254S, A261T, A261S, L263I, V264A, P268P, R272Q, L278L, A280T, A280A, E281E, L282L, V283V, T285A, R287R, R287H, A288V, A288T, P292P, P295P, L302L, V306V, V306A, C307C, A311V, K313R, K313K, R319K, R319G, H321P, H321N, S328S, F331S, P332H, K333K, H334R, A341D, A347E, V353I, D355N, D359N, D359D, D359A, A360V, A360T, E361E, R362K, V366I, A369P, A369E, A369T, A369S, G370G, V375V, V380I, L387L, T388M, R397R, A398S, A405A, R409H, A411V, A414A, A414V, A415S, R416K, E419E, A425T, A425A, R426K S428S, E434G, T435T, R444L, E445Q, T453I, R461R, T463I, V466M, V466V, V466L, G468D, G468G, F476F, L479I, Q480STOP, E483E, Q484K, R487R, del L488, G489G, R494S, R494R, H496N, and/or M499T relative to SEQ ID NO:1. In some aspects, the evolved Bxb1 integrase has a combination of mutations as described herein, e.g., the combination of mutations being any one of the combinations listed in Table 1 with SEQ ID NO:1 (wild-type Bxb1) as reference.

TABLE 1

| Combination of Mutations | Exemplary Combination of Mutations |
|---|---|
| H111X, E434X | H111P, E434G |
| G156X, A369X | G156G, A369P |
| R63X, R88X, A110X, P295X | R63K, R88R, A110A, P295P |
| D36X, R63X, P292X, L479X | D36A, R63K, P292P, L479I |
| V5X, S106X, E434X | V5V, S106S, E434G |
| D51X, H189X | D51D, H189N |
| L164X, H203X, Q480X | L164L, H203Y, Q480STOP |
| F67X, V187X, A261X | F67S, V187I, A261T |
| I87X, B14: B33V187X, A218X, E419X, A425X, E483X | I87L, B14: B33V187V, A218A, E419E, A425T, E483E |
| R63X, A119X, P295X, E361X, M499X | R63K, A119S, P295P, E361E, M499T |
| R63X, V122X, P295X | R63K, V122M, P295P |
| R63X, A347X | R63K, A347E |
| V40X, R63X, V122X, P295X, R319X, S428X | V40I, R63K, V122M, P295P, R319K, S428S |
| R63X, V122X, P295X, R487X | R63K, V122M, P295P, R487R |
| L278X, P295X, P332X, A369X, V380X | L278L, P295P, P332H, A369T, V380I |
| E42X, R63X, D99X, E133X, A145X, K153X, P295X, A369X, R494X | E42K, R63K, D99N, E133E, A145T, K153K, P295P, A369E, R494S |
| V40X, R63X, H89X, Q191X, P295X, L302X, C307X | V40A, R63K, H89G, Q191Q, P295P, L302L, C307C |
| V40X, R63X, P295X, R362X, G370X, G468X | V40V, R63K, P295R, R362K, G370G, G468G |
| G209X, A288X, A311X, A398X, R416X, T453X, H496X, E42X, G209X | G209G, A288V, A311V, A398S, R416K, T453I, H496N, E42K, G209G |
| A288X, A311X, A398X, R416X, T453X, H496X | A288V, A311V, A398S, R416K, T453I, H496N |
| S18X, R63X, E69X, I87X, P295X, P332X, H334X, A369X | S18S, R63K, E69E, I87V, P295P, P332H, H334R, A369E |
| S18X, E42X, R63X, E69X, E133X, P295X, P332X, H334X | S18S, E42K, R63K, E69E, E133E, P295P, P332H, H334R |
| P268X, A288X, A311X, D359X, T388X, T453X, V466X, H496X | P268P, A288V, A311V, D359D, T388M, T453I, V466V, H496N |
| A288X, A311X, R319X, A398X, R416X, T453X, H496X, E434G | A288V, A311V, R319G, A398S, R416K, T453I, H496N, E434G |
| E42X, A288X, A311X, A398X, R416X, T453X, H496X, E434X | E42K, A288V, A311V, A398S, R416K, T453I, H496N, E434G |
| H95X, R287X, K313X | H95Y, R287R, K313R |
| H95X, A280X | H95Y, A280T |
| H95X, V264X | H95Y, V264A |
| H95X, T254X | H95Y, T254S |
| V46X, H95X, V179X, R223X | V46V, H95Y, V179A, R223R |
| H95X, V264X, E434X | H95Y, V264A, E434G |
| H95X, A62X, V466X | H95Y, A62A, V466M |
| A280X, A360X | A280A, A360T |
| L61X, E434X | L61F, E434G |
| L174X, S231X, A288X, E434X, T463X | L174L, S231S, A288T, E434G, T463I |
| V40X, A130X, V283X, A288X, E434X, G468X | V40V, A130A, V283V, A288T, E434G, G468D |
| E229X, K313X, A405X, T453X | E229K, K313K, A405A, T453I |
| L90X, E229X, N251X, D359X, A360X, V375X, R494X | L90L, E229K, N251K, D359N, A360T, V375V, R494R |
| Q92X, V179X, R181X, E229X, M239X, A360X, R444X | Q92Q, V179I, R181K, E229K, M239I, A360T, R444L |
| E69X, I87X, N251X, H321X, D355X | E69A, I87L, N251N, H321P, D355N |
| D51X, I87X, R272X, G489X | D51N, I87L, R272Q, G489G |
| I87X, L488X | I87L, del L488 frameshift |
| I87X, V105X, H321X, S328X, R397X, A411X | I87L, V105A, H321N, S328S, R397R, A411V |
| R79X, I87X, Q484X | R79R, I87L, Q484K |
| I87X, I137X, F331X, R409X, L488X | I87L, I137I, F331S, R409H, del L488 frameshift |
| E69X, H95X, R461X | E69A, H95Y, R461R |
| H95X, L282X | H95Y, L282L |
| I87X, A369X, F476X | I87L, A369P, F476F |
| G34X, I87X, T166X, E229X, A369X, T435X, G489X | G34D, I87L, T166I, E229K, A369P, T435T, G489G |
| I87X, R88X, R140X, K333X, A369X, A414X, V466X, F476X | I87L, R88R, R140R, K333K, A369P, A414A, V466M, F476F |
| I87X, A369X, E434X | I87L, A369S, E434G |
| I87X, A369X, A414X, A425X, E434X | I87L, A369P, A414V, A425A, E434G |
| R85X, I87X, A248X, V306X, A369X, A415X, E434X | R85R, I87L, A248T, V306V, A369P, A415S, E434G |

TABLE 1-continued

| Combination of Mutations | Exemplary Combination of Mutations |
|---|---|
| I87X, P160X, V175X, V187X, A218X, E281X, V353X, E419X, A425X, E483X | I87L, P160P, V175V, V187V, A218A, E281E, V353I, E419E, A425T, E483E |
| I87X, Q92X, P160X, V175X, P178X, V187X, A218X, E281X, V353X, E419X, A425X, E483X | I87L, Q92H, P160P, V175V, P178P, V187V, A218A, E281E, V353I, E419E, A425T, E483E |
| E24X, I87X, H100X, V187X, A218X, E419X, A425X, E483X | E24E, I87L, H100N, V187V, A218A, E419E, A425T, E483E |
| I87X, V187X, A218X, A369X, E419X, A425X, E483X | I87L, V187V, A218A, A369E, E419E, A425T, E483E |
| I87X, V187X, A218X, E419X, A425X, E434X, E483X | I87L, V187V, A218A, E419E, A425T, E434G, E483E |
| I87X, H95X | I87L, H95Y |
| I87X, V122X | I87L, V122M |
| I87X, A369X | I87L, A369P |
| I87X, E434X | I87L, E434G |
| H95X, V122X | H95Y, V122M |
| H95X, A369X | H95Y, A369P |
| H95X, E434X | H95Y, E434G |
| V122X, A369X | V122M, A369P |
| V122X, E434X | V122M, E434G |
| A369X, E434X | A369P, E434G |
| I87X, H95X, V122X | I87L, H95Y, V122M |
| I87X, H95X, A369X | I87L, H95Y, A369P |
| I87X, H95X, E434X | I87L, H95Y, E434G |
| I87X, V122X, A369X | I87L, V122M, A369P |
| I87X, V122X, E434X | I87L, V122M, E434G |
| I87X, A369X, E434X | I87L, A369P, E434G |
| H95X, V122X, A369X | H95Y, V122M, A369P |
| H95X, V122X, E434X | H95Y, V122M, E434G |
| H95X, A369X, E434X | H95Y, A369P, E434G |
| V122X, A369X, E434X | V122M, A369P, E434G |
| I87X, H95X, V122X, A369X | I87L, H95Y, V122M, A369P |
| I87X, H95X, V122X, E434X | I87L, H95Y, V122M, E434G |
| I87X, H95X, A369X, E434X | I87L, H95Y, A369P, E434G |
| I87X, V122X, A369X, E434X | I87L, V122M, A369P, E434G |
| H95X, V122X, A369X, E434X | H95Y, V122M, A369P, E434G |
| I87X, H95X, V122X, A369X, E434X | I87L, H95Y, V122M, A369P, E434G |
| L4X, R63X, I87X, H95X, H111X, V122X, A280X, A369X, E434X, V466X | L4I, R63K, I87L, H95Y, H111P, V122M, A280T, A369P, E434G, V466M |
| R63X, V122X | R63K, V122M |
| H89X, A360X | H89Y, A360V |
| R181X, A341X | R181R, A341D |
| R287X, A425X | R287H, A425A |
| V50X, V306X | V50I, V306A |
| V366X, R426X | V366I, R426K |
| D359X, L387X | D359A, L387L |
| R57X, R63X, P295X | R57K, R63K, P295P |
| R63X, I87X, H100X, N194X, P295X, C307X | R63K, I87V, H100H, N194D, P295P, C307C |

X may be any amino acid.

A wild-type PhiC31 integrase may have the following amino acid sequence:

(SEQ ID NO: 2)
MDTYAGAYDRQSRERENSSAASPATQRSANEDKAADLQREVERDG

GRFRFVGHFSEAPGTSAFGTAERPEFERILNECRAGRLNMIIVYD

VSRFSRLKVMDAIPIVSELLALGVTIVSTQEGVFRQGNVMDLIHL

IMRLDASHKESSLKSAKILDTKNLQRELGGYVGGKAPYGFELVSE

TKEITRNGRMVNVVINKLAHSTTPLTGPFEFEPDVIRWWWREIKT

HKHLPFKPGSQAAIHPGSITGLCKRMDADAVPTRGETIGKKTASS

AWDPATVMRILRDPRIAGFAAEVIYKKKPDGTPTTKIEGYRIQRD

PITLRPVELDCGPIIEPAEWYELQAWLDGRGRGKGLSRGQAILSA

MDKLYCECGAVMTSKRGEESIKDSYRCRRRKVVDPSAPGQHEGTC

NVSMAALDKFVAERIFNKIRHAEGDEETLALLWEAARRFGKLTEA

PEKSGERANLVAERADALNALEELYEDRAAGAYDGPVGRKHFRKQ

QAALTLRQQGAEERLAELEAAEAPKLPLDQWFPEDADADPTGPKS

WWGRASVDDKRVFVGLFVDKIVVTKSTTGRGQGTPIEKRASITWA

KPPTDDDEDDAQDGTEDVAA

In one aspect is provided an evolved PhiC31 integrase having an amino acid sequence that is at least 70%, at least 80%, at least 90%, at least 95%, at least 97%, at least 98% or at least 99% identical to the amino acid sequence of SEQ ID NO:2, wherein the evolved PhiC31 integrase has at least one mutation and exhibits an increase in insertion efficiency as compared to wild-type PhiC31 integrase. In some aspects, the evolved PhiC31 integrase has between one and 13 mutations, e.g., between one and 3 mutations, between 2 and 4 mutations, between 3 and 5 mutations, between 4 and 6 mutations, between 5 and 7 mutations, between 6 and 8 mutations, between 7 and 9 mutations, between 8 and 10 mutations, between 9 and 11 mutations, between 10 and 12 mutations or between 11 and 13 mutations as compared to the wild-type PhiC31 integrase (e.g., SEQ ID NO:2). In other aspects, the evolved PhiC31 integrase has at least one mutation, at least 2 mutations, at least 3 mutations, at least 4 mutations, at least 5 mutations, at least 6 mutations, at least 7 mutations, at least 8 mutations, at least 9 mutations, at least 10 mutations, at least 11 mutations, at least 12 mutations, or at least 13 mutations as compared to the wild-type PhiC31 integrase (e.g., SEQ ID NO:2).

In further aspects, the evolved PhiC31 integrase has at least one mutation, the at least one mutation being at position 1, 2, 12, 14, 18, 24, 32, 36, 41, 43, 44, 45, 49, 51, 55, 58, 74, 77, 96, 103, 107, 117, 153, 176, 196, 197, 199, 200, 228, 229, 230, 231, 235, 238, 240, 252, 254, 255, 260, 262, 264, 266, 269, 274, 278, 302, 319, 320, 322, 331, 333, 340, 344, 345, 346, 347, 351, 353, 355, 359, 362, 364, 378, 382, 393, 396, 397, 399, 406, 410, 424, 429, 431, 436, 438, 445, 448, 449, 450, 452, 457, 468, 472, 478, 498, 499, 501, 505, 512, 514, 516, 517, 520, 527, 535, 536, 549, 551, 552, 553, 563, 568, 580, 585, 586, 587, 590, 592, 594, 600, 603, 604, 609, 612, and/or 616 relative to SEQ ID NO:2. In some aspects, the evolved PhiC31 integrase has at least one mutation, the at least one mutation being M1E, M1V, D2V, D2M, S12N, E14G, S18N, A24A, D32A, D36A, V41I, R43R, D44A, G45G, R49R, V51M, S55S, P58P, I74I, E77E, R96R, I103I, S107S, V117V, I153I, I153V, E176D, N196N, K197K, A199T, H200H, H228Y, L229L, P230S, F231L, S235S, A238A, H240R, D252G, D254D, A255G, G260G, T262T, G264G, K266K, S269N, P274S, M278L, T302A, L319L, R320R, V322V, E331E, A333T, A333S, A333D, A340V, G344V, G344D, R345R, G346S, R347K, L351V, L351Q, R353R, Q355Q, S359S, D362N, D362G, L364M, E378K, K382K, V393V, S396N, S396R, A397T, G399G, N406S, A410T, I424I, G429S, E431V, L436L, W438R, G445G, W448R, E449D, A450D, E452K, R457R, L468L, E472D, R478R, A498A, L499L, L501L, G505V, G505G, G505S, E512K, E514E, A516T, E517E, K520K, F527F, P535L, P535P, T536A, D549D, R551R, V552V, F553F, V563V, T568T, A580V, A585A, K586Q, P587P, D590G, D592G, D594N, D594D, T600S, T600T, V603I, V603A, V603V, A604S, P609S, V612V, and/or A616V relative to SEQ ID NO:2. In some aspects, the evolved PhiC31 integrase has a combination of mutations, the combination of mutations being any one of the combinations listed in Table 2 with wild-type PhiC31 (SEQ ID NO:2) as reference.

TABLE 2

| Combination of Mutations | Exemplary Combinations of Mutations |
| --- | --- |
| M1X, D2X, V41X | M1E, D2V, V41I |
| D32X, D36X, D44X | D32A, D36A, D44A |
| M1X, D2X, D32X, D36X, V41X, D44X | M1V, D2V, D32A, D36A, V41I, D44A |
| M1X, D2X, V41X, R49X, M278X, L319X, F527X | M1V, D2V, V41I, R49R, M278L, L319L, F527F |
| M1X, D2X, V41X, L229X, G344X | M1V, D2V, V41I, L229L, G344V |
| M1X, D2X, V41X, E431X | M1V, D2V, V41I, E431V |
| M1X, D2X, V41X, R43X, P230X, Q355X, K520X | M1V, D2V, V41I, R43R, P230S, Q355Q, K520K |
| M1X, D2X, V41X, V117X, H228X, A255X, A580X, D594X | M1V, D2V, V41I, V117V, H228Y, A255G, A580V, D594D |
| M1X, D2X, V41X, G505X, P587X, D594X | M1V, D2V, V41I, G505V, P587P, D594N |
| D32X, A199X, P535X | D32A, A199T, P535P |
| D32X, D36X, D44X, S396X, R551X | D32A, D36A, D44A, S396N, R551R |
| D32X, D36X, D44X, N406X, E512X | D32A, D36A, D44A, N406S, E512K |
| D32X, D36X, D44X, K197X, D254X, G344X, A397X, R457X, A616X | D32A, D36A, D44A, K197K, D254D, G344D, A397T, R457R, A616V |
| D32X, D36X, D44X, S55X, E77X, I153X, G344X, S359X, V552X, A585X | D32A, D36A, D44A, S55S, E77E, I153I, G344D, S359S, V552V, A585A |
| D32X, D36X, D44X, K266X, D362X | D32A, D36A, D44A, K266K, D362G |
| D32X, D36X, D44X, F231X, G505X, D592X | D32A, D36A, D44A, F231L, G505S, D592G |
| D32X, D36X, D44X, I103X, T302X, D362X, G399X, E449X, E472X | D32A, D36A, D44A, I103I, T302A, D362G, G399G, E449D, E472D |
| D32X, D36X, D44X, E77X, I153X, H200X, P274X, G344X, K382X, T536X | D32A, D36A, D44A, E77E, I153I, H200H, P274S, G344D, K382K, T536A |
| D32X, D36X, D44X, R320X, A333X, G429X, A516X, A604X | D32A, D36A, D44A, R320R, A333T, G429S, A516T, A604S |
| D32X, D36X, D44X, A238X, R457X, P535X | D32A, D36A, D44A, A238A, R457R, P535L |
| E14X, D32X, D36X, D44X, E176X, A238X, S396X, R478X, F553X, K586X | E14G, D32A, D36A, D44A, E176D, A238A, S396R, R478R, F553F, K586Q |
| D32X, D36X, D44X, E176X, L229X, A238X, A333X, S359X | D32A, D36A, D44A, E176D, L229L, A238A, A333D, S359S |
| D32X, D36X, D44X, I74X, R96X, E176X, A238X, A333X, E378X, D590X | D32A, D36A, D44A, I74I, R96R, E176D, A238A, A333D, E378K, D590G |
| M1X, D2X, D32X, D36X, V41X, D44X | M1E, D2V, D32A, D36A, V41I, D44A |
| M1X, D2X, D32X, D36X, V41X, D44X, S235X, L364X | M1E, D2V, D32A, D36A, V41I, D44A, S235S, L364M |
| M1X, D2X, D32X, D36X, V41X, D44X, G346X, G505X | M1E, D2V, D32A, D36A, V41I, D44A, G346S, G505G |
| M1X, D2X, D32X, D36X, V41X, D44X, R345X, D362X, L468X, V603X | M1E, D2V, D32A, D36A, V41I, D44A, R345R, D362N, L468L, V603I |
| M1X, D2X, D32X, D36X, V41X, D44X, D362X, V612X | M1E, D2V, D32A, D36A, V41I, D44A, D362N, V612V |
| M1X, D2X, A24X, D36X, V41X, D44X, N196X, W448X, P609X | M1E, D2V, A24A, D36A, V41I, D44A, N196N, W448R, P609S |

TABLE 2-continued

| Combination of Mutations | Exemplary Combinations of Mutations |
|---|---|
| M1X, D2X, D32X, D36X, V41X, D44X, D362X, V563X, T600X | M1E, D2V, D32A, D36A, V41I, D44A, D362G, V563V, T600T |
| M1X, D2X, D32X, D36X, V41X, D44X, F231X, A410X, V603X | M1E, D2V, D32A, D36A, V41I, D44A, F231L, A410T, V603V |
| M1X, D2X, D32X, D36X, V41X, D44X, T262X, D362X, V393X, L436X | M1E, D2V, D32A, D36A, V41I, D44A, T262T, D362N, V393V, L436L |
| M1X, D2X, D32X, V41X, D44X, G45X, G264X, E331X, L351X, G445X, V563X, A580X, V603X | M1E, D2M, D32A, V41I, D44A, G45G, G264G, E331E, L351V, G445G, V563V, A580V, V603V |
| M1X, D2X, A24X, D32X, D36X, V41X, D44X, W438X, P609X | M1E, D2V, A24A, D32A, D36A, V41I, D44A, W438R, P609S |
| M1X, D2X, A24X, D32X, D36X, V41X, D44X, H240X, A333X, A340X, W448X, T600X, P609X | M1E, D2V, A24A, D32A, D36A, V41I, D44A, H240R, A333S, A340V, W448R, T600S, P609S |
| M1X, D2X, D32X, D36X, V41X, D44X, R347X, I424X | M1E, D2V, D32A, D36A, V41I, D44A, R347K, I424I |
| M1X, D2X, D32X, D36X, V41X, D44X, V322X, L351X, D549X | M1E, D2V, D32A, D36A, V41I, D44A, V322V, L351Q, D549D |
| M1X, D2X, D32X, D36X, V41X, D44X, S107X, D362X | M1E, D2V, D32A, D36A, V41I, D44A, S107S, D362N |
| M1X, D2X, S12X, D32X, D36X, V41X, D44X, P58X, I103X, E153X, E514X, A580X, V603X | M1E, D2V, S12N, D32A, D36A, V41I, D44A, P58P, I103I, E153V, E514E, A580V, V603A |
| M1X, D2X, D32X, D36X, V41X, D44X, R353X, D362X, L499X, T568X | M1E, D2V, D32A, D36A, V41I, D44A, R353R, D362N, L499L, T568T |
| M1X, D2X, S18X, D32X, D36X, V41X, D44X, V51X, I103X, I153X, A450X, V603X | M1E, D2V, S18N, D32A, D36A, V41I, D44A, V51M, I103I, I153V, A450D, V603A |
| M1X, D2X, D32X, D36X, V41X, D44X, I103X, I153X, S269X, A450X, E517X, V603X | M1E, D2V, D32A, D36A, V41I, D44A, I103I, I153V, S269N, A450D, E517E, V603A |
| M1X, D2X, D32X, D36X, V41X, D44X, I103X, I153X, G260X, L436X, A450X, L501X, V603X | M1E, D2V, D32A, D36A, V41I, D44A, I103I, I153V, G260G, L436L, A450D, L501L, V603A |
| M1X, D2X, D32X, D36X, V41X, D44X, I103X, I153X, A450X, E452X, V603X | M1E, D2V, D32A, D36A, V41I, D44A, I103I, I153V, A450D, E452K, V603A |

X may be any amino acid.

In some aspects, the evolved PhiC31 integrase may further include one or more of the following mutations: M1E, D2V, D32A, D36A, V41I, and/or D44A with respect to the wild-type sequence (SEQ ID NO:2). In other aspects, the evolved PhiC31 further includes the combination of V41I; D32A, D36A and D44A; or D32A, D36A, V41I, and D44A.

In still further aspects, the evolved PhiC31 integrase may have the N-terminal sequence as in SEQ ID NO:2 or may further include the N-terminal amino acid sequences listed in Table 3, which replace the methionine at position 1 of SEQ ID NO:2.

TABLE 3

| N-terminal Sequence | SEQ ID NO: |
|---|---|
| MIQGVVSG | 3 |
| MIQEVVSG | 4 |
| MTMITPSAQLTLTKGNKSWSSLVTAASVLEFATMIQGVAG | 5 |
| MTMIYPFPAQLTLTKGNKSWSSLVTAASVLEFATMIQGVAG | 6 |
| MTMITPSAQLTLTKSNKSWNSLVTAASVLEFATMIQGVAG | 7 |
| MTMITPSAQLTLTKGNKSWSSLVTAASVLEFATMIQGVAG | 8 |
| MTMITPSAQLTLTKSNKSWSSLVTAASVLEFATMIQGVTG | 9 |
| MTMITPSAQLTLTKDNKSWSSLVTAASVLEFATMIQGVAG | 10 |
| MTMITPSAQLTLTKSNKSWSSLVTAASVLEFATMIQGVAG | 11 |
| MTMITPSAQLTLTKSNKSWSSLVTAASVLEFATMIQGVAG | 12 |

In some aspects, one or more of the mutations in the evolved Bxb1 and PhiC31 integrases are amino acid substitutions. Substitutions, for example, those designated herein, e.g., in Tables 1 and 2, may be conservative or nonconservative, i.e., amino acid residues designated as "X" may conservative or nonconservative substitutions of the wild-type amino acid residue at the indicated position. In contrast to a nonconservative amino acid substitution, a conservative amino acid substitution is one in which an amino acid is substituted for another amino acid having similar properties such that the folding or activity of the protein is not significantly affected. Aromatic amino acids that can be substituted for each other are phenylalanine, tryptophan, and tyrosine; interchangeable hydrophobic amino acids are leucine, isoleucine, methionine, and valine; interchangeable polar amino acids are glutamine and asparagine; interchangeable basic amino acids are arginine, lysine, and histidine; interchangeable acidic amino acids are aspartic acid and glutamic acid; and interchangeable small amino acids are alanine, serine, threonine, cysteine, and glycine. A mutation within the context of this disclosure may also include "silent mutations" that do not result in changes to the amino acid sequence.

In some aspects, the evolved Bxb1 integrase or evolved PhiC31 integrase described herein, referred to generally as the "evolved integrase," recognizes (i.e., binds) an integrase recognition sequence that comprises a naturally occurring sequence, i.e., its canonical integrase recognition sequence. In some aspects, an evolved integrase recognizes an integrase recognition sequence that is in the genome of a mammal. In some aspects, the evolved integrase recognizes an integrase recognition sequence in the genome of a human. In some aspects, the evolved integrase recognizes an integrase recognition sequence that occurs only once in the genome of a mammal. In some aspects, the evolved integrase recognizes an integrase recognition sequence in the genome of a mammal that differs from any other site in the genome by at least 1, at least 2, at least 3, at least 4, at least 5, at least 6, at least 7, at least 8, at least 9, at least 10, at least 11, at least 12, at least 13, at least 14, or at least 15 nucleotide(s). Variants may share at least 65%, 70%, 75%, 80%, 85%, 90%, 91%, 92%, 93%, 94%, 95%, 96%, 97%, 98%, 99% or more sequence identity to the native recognition sequence, wherein the variants retain biological activity and hence facilitate a recombination event in the presence of the appropriate integrase. Assays to measure the biological activity of recombination sites are known in the art. See, for example, Senecoff et al. (1988) *J. Mol. Biol.* 201:406-421; Voziyanov et al. (2002) *Nucleic Acid Research* 30:7; U.S. Pat. No. 6,187,994; and Albert et al. (1995) *The Plant Journal* 7:649-659.

In some aspects, the evolved integrase recognizes (i.e., binds) an integrase recognition sequence located in a safe harbor genomic locus. In some aspects, the safe harbor genomic locus is a Rosa26 locus. In other aspects, the safe harbor genomic locus is an AAVS1 locus. In further aspects, the safe harbor genomic locus is an Xq22.1 locus. In some aspects, the evolved integrase recognizes an integrase recognition sequence located in a genomic locus associated with a disease or disorder. In other aspects, the present disclosure provides the use of prime editing, e.g., twin prime editing, to install one or more integrase recognition sequences into the genome at a specified location, such as a safe harbor locus, depending on the desired application. Introduction of two integrase recognition sequences could result in deletion of the intervening sequence, inversion of the intervening sequence, chromosomal translocation, or cassette exchange, depending on the identity and orientation of the targets. By choosing endogenous sequences that already closely resemble integrase recognition sequences, the scope of editing required to introduce the complete integrase recognition sequence would be reduced. Examples of integrase recognition sequences of use in combination with the evolved Bxb1 integrase described herein include, but are not limited to, those having the nucleotide sequence of SEQ ID NO:13-14. Examples of integrase recognition sequences of use in combination with the evolved PhiC31 integrase described herein include, but are not limited to, those having the nucleotide sequence of SEQ ID NO:15-16.

In other aspects, the evolved integrases exhibit at least a 2-fold, preferably at least 3-fold, at least 4-fold, at least 5-fold, at least 6-fold, at least 7-fold, at least 8-fold, at least 9-fold, or at least 10-fold improvement in integration of cargo DNA into a target site as compared to a wild-type integrase (e.g., SEQ ID NO:1 or SEQ ID NO:2).

In some aspects, nucleic acids (RNA, DNA, or a combination thereof) encoding any of the evolved integrases described herein are provided. In some aspects, the nucleic acids encoding the integrases are under the control of a heterologous promoter. In some aspects, the encoding nucleic acids are included in an expression construct, e.g., a plasmid, a viral vector, or a linear expression construct. In some aspects, the nucleic acid or expression construct is in a cell, tissue, or organism.

Nucleic acids encoding any of the evolved integrases described herein, may be in any number of nucleic acid "vectors" known in the art. As used herein, a "vector" means any nucleic acid or nucleic acid-bearing particle, cell, or organism capable of being used to transfer a nucleic acid into a host cell. The term "vector" includes both viral and nonviral products and means for introducing the nucleic acid into a cell. A "vector" can be used in vitro, ex vivo, or in vivo. Nonviral vectors include plasmids, cosmids, artificial chromosomes (e.g., bacterial artificial chromosomes or yeast artificial chromosomes) and can comprise liposomes, electrically charged lipids (cytofectins), DNA-protein complexes, and biopolymers, for example. Viral vectors include retroviruses, lentiviruses, adeno-associated virus, pox viruses, baculovirus, reoviruses, vaccinia viruses, herpes simplex viruses, Epstein-Barr viruses, and adenovirus vectors, for example. Vectors can also include the entire genome sequence or recombinant genome sequence of a virus. A vector can also include a portion of the genome that includes the functional sequences for production of a virus capable of infecting, entering, or being introduced to a cell to deliver nucleic acid therein.

Expression of any of the integrases described herein may be controlled by any regulatory sequence (e.g., a promoter sequence) known in the art. Regulatory sequences, as described herein, are nucleic acid sequences that regulate the expression of a nucleic acid sequence. A regulatory or control sequence may include sequences that are responsible for expressing a particular nucleic acid (e.g., a nucleic acid encoding an integrase) or may include other sequences, such as heterologous, synthetic, or partially synthetic sequences. The sequences can be of eukaryotic, prokaryotic, or viral origin that stimulate or repress transcription of a gene in a specific or non-specific manner and in an inducible or non-inducible manner. Regulatory or control regions may include origins of replication, RNA splice sites, introns, chimeric or hybrid introns, promoters, enhancers, transcriptional termination sequences, poly A sites, locus control regions, signal sequences that direct the polypeptide into the secretory pathways of the target cell, and introns. A heterologous regulatory region is not naturally associated with the expressed nucleic acid it is linked to. Included among the heterologous regulatory regions are regulatory regions from a different species, regulatory regions from a different gene, hybrid regulatory sequences, and regulatory sequences that do not occur in nature, but which are designed by one of ordinary skill in the art.

The term "operably linked" refers to an arrangement of sequences or regions wherein the components are configured so as to perform their usual or intended function. Thus, a regulatory or control sequence operably linked to a coding sequence is capable of affecting the expression of the coding sequence. The regulatory or control sequences need not be contiguous with the coding sequence, so long as they function to direct the proper expression or polypeptide production. Thus, for example, intervening untranslated but transcribed sequences can be present between a promoter sequence and the coding sequence and the promoter sequence can still be considered operably linked to the coding sequence. A promoter sequence, as described herein, is a DNA regulatory region a short distance from the 5' end of a gene that acts as the binding site for RNA polymerase. The promoter sequence may bind RNA polymerase in a cell and/or initiate transcription of a downstream (3' direction) coding sequence. The promoter sequence may be a promoter capable of initiating transcription in prokaryotes or eukaryotes. Some non-limiting examples of eukaryotic promoters include the cytomegalovirus (CMV) promoter, the chicken β-actin (CBA) promoter, and a hybrid form of the CBA promoter (CBh).

Some aspects of this disclosure provide for delivery of the evolved integrases described herein (e.g., as an isolated protein or via nucleic acids encoding the evolved integrase) to host cells. Some aspects provide host cells expressing an evolved integrase provided herein, e.g., by virtue of harboring nucleic acids and/or an expression construct encoding the evolved integrase. In some aspects, cells contacted with an evolved integrase (e.g., protein or nucleic acids encoding the evolved integrase) as described herein are provided, e.g., cells contacted in vitro, in vivo, or ex vivo. In some aspects, the cell is a prokaryotic cell, for example, a bacterial cell. In some aspects, the cell is an *E. coli* cell. In some aspects, the cell is a eukaryotic cell, for example, a yeast cell, an insect cell, or a mammalian cell, e.g., hamster host cell, a human host cell, a rat host cell, or a mouse host cell. In some aspects, a host cell is a Chinese hamster ovary (CHO) cell, a CHO K1 host cell, a CHO K1SV host cell, a DG44 host cell, a DUKXB-11 host cell, a CHOK1S host cell, a CHO K1M host cell, a monkey kidney CV1 line transformed by SV40 (COS-7), human embryonic kidney line (293 or HEK293T), baby hamster kidney cells (BHK), mouse sertoli cells (TM4 cells), African green monkey kidney cells (VERO-76), human cervical carcinoma cells (HELA), canine kidney cells (MDCK), buffalo rat liver cells (BRL 3A), human lung cells (W138), human liver cells (Hep G2), mouse mammary tumor (MMT 060562), TRI cells, MRC5 cells, FS4 cells, YO cells, NSO cells, Sp2/0 cells, or PER.C6® cells.

In some aspects, a host cell is a cell line that has been cultured for a certain number of generations. In certain aspects, a host cell is a primary cell. In some aspects, a host cell is a T cell.

Some aspects further provide pharmaceutical compositions comprising an evolved integrase as provided herein and a pharmaceutically acceptable carrier. In some aspects, the pharmaceutical composition is formulated for administration to a subject. In some aspects, the pharmaceutical composition comprises an effective amount of the evolved integrase for recombining an integrase recognition sequence in a cell of a subject in vivo, ex vivo, or in vitro. In some aspects, the composition further comprises a nucleic acid molecule comprising at least one integrase recognition sequence adjacent to a sequence to be inserted into a genetic locus within the genome of the subject.

As used here, the term "pharmaceutically-acceptable carrier" means a pharmaceutically-acceptable material, composition or vehicle, such as a liquid or solid filler, diluent, excipient, manufacturing aid (e.g., lubricant, talc magnesium, calcium or zinc stearate, or steric acid), or solvent encapsulating material, involved in carrying or transporting the compound from one site (e.g., the delivery site) of the body, to another site (e.g., organ, tissue or portion of the body). A pharmaceutically acceptable carrier is "acceptable" in the sense of being compatible with the other ingredients of the formulation and not injurious to the tissue of the subject (e.g., physiologically compatible, sterile, physiologic pH, etc.). Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, methylcellulose, ethyl cellulose, microcrystalline cellulose and cellulose acetate; (4) powdered tragacanth; (5) malt; (6) gelatin; (7) lubricating agents, such as magnesium stearate, sodium lauryl sulfate and talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol (PEG); (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; (22) bulking agents, such as polypeptides and amino acids (23) serum component, such as serum albumin, HDL and LDL; (22) C2-C12 alcohols, such as ethanol; and (23) other non-toxic compatible substances employed in pharmaceutical formulations. Wetting agents, coloring agents, release agents, coating agents, sweetening agents, flavoring agents, perfuming agents, preservative, and antioxidants can also be present in the formulation. The terms such as "excipient", "carrier", "pharmaceutically acceptable carrier" or the like are used interchangeably herein. In some aspects, the pharmaceutical composition is formulated for delivery to a subject, e.g., for gene editing.

The evolved integrases may be provided or packaged as a unit dose. The term "unit dose" when used in reference to a pharmaceutical composition refers to physically discrete units suitable as unitary dosage for the subject, each unit containing a predetermined quantity of active material calculated to produce the desired therapeutic effect in association with the required diluent, i.e., a carrier or vehicle.

In some aspects, a method of altering the sequence of a genome of a cell is provided. In accordance with this method, a cell is contacted with an evolved integrase described herein (e.g., an evolved Bxb1 or PhiC31 integrase protein or a nucleic acid molecule encoding an evolved Bxb1 or PhiC31 integrase), either in vivo, ex vivo, or in vitro, wherein the cell comprises in its genome at least one integrase recognition sequence recognized by the evolved integrase so that the evolved integrase binds to the integrase recognition sequence and alters the sequence of the genome of the cell. In some aspects, the alteration or change in the genome is a transversion, transition, deletion, or insertion. In some aspects, the alteration or change in the genome includes an excision of a sequence associated with a disease or disorder, such as, for example, a mutated version of a gene, or an integrated viral genome. In some aspects, the alteration or change in the genome may be a mutation-correcting change to a nucleotide sequence, insertion of a protein or RNA tag, insertion of immunoepitopes on proteins of interest, insertion of inducible dimerization domains in proteins, and/or introduce or remove sequences to alter that activity of a biomolecule, In some aspects, the contacting results in the integration of an exogenous nucleic acid sequence into the genome of the cell, e.g., at a safe harbor locus (e.g., Rosa26, AAVS1 or Xq22.1 locus) or in place of an undesired sequence.

In some aspects, the evolved integrases are used in combination with prime editing (PE), twin prime editing or multi-flap prime editing approaches to genome editing. See, e.g., PCT/US2021/31439 and PCT/US2022/078655. Twin prime editing and multi-flap prime editing involve the installation of one or more site specific integrase recognition sequences in a target genomic locus (e.g., a specific gene, exon, intron, or regulatory sequence of a target DNA, target gene, target genome, or target cell). The integrated one or more site-specific integrase recognition sequences may then undergo site-specific recombination in the presence of the integrase to effectuate a large-scale genetic alteration or change, such as an insertion, deletion, inversion, replacement, and/or chromosomal translocation.

In some aspects, insertion of a two or more integrase recognition sites can be accomplished with either prime editing having single PEgRNAs (multiplexed single flap prime editing) or twin prime editing. For example, in some aspects, a prime editor system including a single PEgRNA directs the prime editor system to introduce two or more integrase recognition sites in a target DNA. In some aspects, a prime editor system includes two or more PEgRNAs, wherein each of the two or more PEgRNAs include a DNA synthesis template that independently include an integrase recognition site. For example, a prime editor system may include a first PEgRNA and a second PEgRNA, wherein the first PEgRNA includes a first spacer that is complementary to a first target region in a target DNA, and a first DNA synthesis template that includes a first integrase recognition site, and wherein the second PEgRNA includes a second spacer that is complementary to a second target region in a target DNA, and a second DNA synthesis template that includes a second integrase recognition site, and wherein the first target region and the second target region are in different positions in the target DNA.

Integrase recognition sites introduced by prime editing can be used to generate an intended edit, including deletions, insertions, integrations, and replacement by donor sequences. In some aspects, an insertion interrupts the expression of a protein encoding gene, wherein the interruption of expression confers a therapeutic benefit in a cell. In some aspects, the insertion interrupts the expression of a protein coding gene, wherein the protein coding gene has deleterious effect to the cell or the subject, for example, a gene having a gain of function mutation. In some aspects, the insertion is at a genomic location that allows expression of the DNA sequence that is inserted. For example, in some aspects, the insertion is directly downstream of an endogenous gene promoter.

In some aspects, the inserted sequence encodes a protein, or is a portion of a gene that encodes a protein. For example, in some aspects, a target gene includes a 5' portion and a 3' portion, where the 3' portion includes a mutation associated with a disease. In some aspects, the inserted DNA sequence can be downstream of the 5' portion, e.g., at the 3' end of an endogenous exon, wherein the inserted DNA sequence has a wild-type sequence corresponding to the 3' portion of the gene, thereby restoring wild-type sequence of the gene. In some aspects, the inserted DNA sequence includes a stop codon at the 3' end. In some aspects, prime editing with an evolved integrase results in replacement of an endogenous sequence in a target DNA by an exogenous nucleic acid sequence, or replacement of a target gene by an exogeneous nucleic acid sequence.

For example, in some embodiments, the target DNA in the genome of a cell is a target gene that includes one or more mutations associated with a disease. In some embodiments, a fragment of the target gene that includes the one or more mutations can be replaced with an exogenous nucleic acid sequence that has wild-type sequence of the same gene corresponding to the endogenous portion that comprises the one or more disease associated mutations.

In some aspects, the inserted exogenous nucleic acid sequence encodes a therapeutic protein. In some aspects, the inserted exogenous nucleic acid sequence is a therapeutic gene or a portion of the therapeutic gene that encodes a therapeutic protein, wherein the target genome includes one or more endogenous copies of the same gene that has a mutation. In some aspects, the mutation is a loss of function mutation, and expression of the inserted exogenous nucleic acid sequence restores or partially restores wild-type expression of the protein. For example, the therapeutic protein is Factor VIII. In some aspects, the therapeutic protein is adult hemoglobin or fetal hemoglobin. Other therapeutic genes encoding therapeutic proteins include genes encoding, e.g., steroids, growth factors, insulin, neurotransmitters, dopamine, norepinephrine, epinephrine, histamine, serotonin, checkpoint inhibitor proteins, antibodies, antigen receptor polypeptides, cell surface marker recognition polypeptides, a chimeric antigen receptor (CAR), a T-cell receptor, a protein involved in protein process (e.g., a degron or ubiquitin). Other sequences that may be inserted include a tissue specific promoters, enhancers, repressors, or insulators.

In some aspects, the evolved integrases are used in the treatment of a disease or disorder, i.e., site-specific recombination via the evolved integrase effectuates a large-scale genetic alteration or change to delay the development or progression of the disease or reduce disease severity. Treating the disease does not necessarily require curative results. As used therein, "delaying" the development of a disease means to defer, hinder, slow, retard, stabilize, and/or postpone progression of the disease. This delay can be of varying lengths of time, depending on the history of the disease and/or individuals being treated. A method that "delays" or alleviates the development of a disease, or delays the onset of the disease, is a method that reduces probability of developing one or more symptoms of the disease in a given time frame and/or reduces extent of the symptoms in a given time frame, when compared to not using the method. Such comparisons are typically based on clinical studies, using a number of subjects sufficient to give a statistically significant result.

"Development" or "progression" of a disease means initial manifestations and/or ensuing progression of the disease. Development of the disease can be detectable and assessed using standard clinical techniques as well known in the art. However, development also refers to progression that may be undetectable. For purpose of this disclosure, development or progression refers to the biological course of the symptoms. "Development" includes occurrence, recurrence, and onset.

As used herein "onset" or "occurrence" of a disease includes initial onset and/or recurrence. Conventional methods, known to those of ordinary skill in the art of medicine, can be used to administer the isolated polypeptide or pharmaceutical composition to the subject, depending upon the type of disease to be treated or the site of the disease.

Many large-scale genomic alterations or changes, such as gene insertions, deletions, inversions, replacements, or chromosomal translocations, are implicated in genetic disease. For example, microdeletions of chromosomes can lead to disease, and replacement of these deletions by insertions of critical DNA elements could lead to a permanent amelioration of disease. In addition, diseases resulting from inversions, gene copy number changes, or chromosomal translocations could be addressed by restoring the previous gene structure in affected cells. Examples of genetic diseases linked to large-scale genomic modifications that may be treated using the evolved integrases include, but are not limited to, Trisomy 17p (a gene duplication), Charcot-Marie-Tooth disease type I (a gene duplication), Smith- Magenis syndrome (a gene deletion), Williams-Beuren syndrome (a gene deletion), De la Chapelle syndrome (a chromosomal translocation), some forms of Down Syndrome (a chromosomal translocation), Hemophilia A (a gene inversion), and Hunter syndrome (a gene inversion).

The following non-limiting examples are provided to further illustrate the present invention.

Example 1: Materials and Methods

General Methods. Oligonucleotides and synthetic DNA fragments were purchased from Integrated DNA Technologies. PCR amplification of DNA fragments was performed with KOD One™ PCR Mastermix (Toyobo). Plasmids were constructed using NEBuilder® HiFi DNA Assembly or USER® cloning (New England Biolabs) and purified with the Zyppy™ Plasmid Miniprep Kit (Zymo). DNA for transfection was purified by Zymopure™ Plasmid Miniprep Kit (Zymo), Zymopure™ Express Plasmid Midiprep Kit (Zymo), or Qiagen® Plasmid Plus Midiprep Kit (Qiagen).

Mammalian expression plasmids. Helper plasmids for mammalian expression called pCMV2 PhiC31 wt, pCMV2 HuOpt Bxb1, and pCMV2 HuOpt Pa01 encode wild-type PhiC31, Bxb1, and Pa01 integrases, respectively. The wild-type protein sequences for Bxb1 and PhiC31 are provided herein as SEQ ID NO:1 and SEQ ID NO:2, respectively. Hyperactive mutations in PhiC31 and Bxb1 integrases were incorporated into pCMV2 PhiC31 wt, and pCMV2 HuOpt Bxb1 for use in genome targeting experiments with mammalian cells. Hyperactive mutations originally identified by Keravala et al. ((2009) *Mol. Ther.* 17(1):112-20) were also incorporated into pCMV2 PhiC31 wt to generate plasmids called pCMV2 PhiC31 P1, pCMV2 PhiC31 P2, and pCMV2 PhiC31 P3. Donor plasmids contained an att site and cargo DNA for genomic insertion. Donor plasmids pCMV PhiC31 attB DsRed Hygro, pCMV Bxb1 attP DsRed Hygro, and pCMV Pa01 attP DsRed Hygro contained att sites for PhiC31, Bxb1, and Pa01 integrases, respectively. The donor plasmids each contained the DsRed fluorescent protein and hygromycin resistance gene. In addition to DsRed and hygromycin, donor plasmids pCDNA4 FVIII Bxb1 attP HIR Donor and pCDNA3.1-WT-VWF Bxb1 attP HIR Donor contained the therapeutic Factor VIII and Von Willebrand Factor (vWF) genes, respectively. The PE5max plasmid encodes an *S. pyogenes* Cas9 (SpCas9) nickase fused to a reverse transcriptase used for PE (Chen et al. (2021) *Cell* 184:5635-5652). Plasmids used for expressing the epegRNA included a spacer sequence that directs the SpCas9 nickase to the genomic target sequence (Anzalone et al. (2022) *Nat. Biotechnol.* 40:731-740; Nelson et al. *Nat. Biotechnol.* 402-410). The epegRNA expression plasmids included a reverse transcription template (RTT) for the att site that became incorporated at the target sequence by PE. The epegRNA expression plasmids were used for PE insertion of the att site at human genomic target sequences AAVS1, Xq22.1, and ROSA26. Helper, donor and epegRNA plasmids will be made available through Addgene.

Mammalian Cell Culture. HEK293 (ATCC CRL-1573) and HEK293T (Thermo Fisher Scientific) cells were maintained in Dulbecco's Modified Eagle Medium (DMEM)+ GlutaMAX™ (Gibco), HeLa cells (Sigma) were maintained in Eagle's Minimum Essential Medium (EMEM) with L-glutamine (ATCC), and K562 cells (Sigma) were maintained in RPMI-1640 medium (Sigma). All media were supplemented with 10% heat inactivated fetal bovine serum (FBS; Neuromics), 1× Penicillin/Streptomycin (Gibco), and 0.75 µg/mL Amphotericin B (Gibco). Phosphate buffered saline (PBS), trypsin, and Opti-MEM™ were purchased from Gibco. Primary hepatocytes (Xenotech) were thawed using the OptiThaw Hepatocyte Kit, plated in OptiPlate medium, and cultured in OptiCulture medium (Xenotech).

Transfection. HEK293, HEK293T, and K562 cells were transfected with TransIT®-2020 (Mirus Bio). Primary hepatocytes were transfected with TransIT®-X2 dynamic (Mirus Bio). HeLa cells were transfected with HeLaMONSTER® (Mirus Bio).

Fluorescence-Activated Cell Sorting (FACS). All donor plasmids constitutively expressed DsRed. For experiments requiring sorting of transfected cells and exclusion of non-transfected cells, including select HEK293T transfections as well as Hela and K562 transfections, a FACSAria™ IIu flow cytometer (BD Biosciences) was used to sort cells based on DsRed fluorescent intensity (excitation 488 nm, emission 610 nm). Cells were immediately pelleted and lysed for droplet digital PCR analysis.

Cell Lysis. Cell pellets were lysed by addition of 90 µl DirectPCR® Cell lysis reagent (Viagen Biotech) with 1.0 mg/mL freshly prepared proteinase K (Meridian Bioscience) and incubation in a hybridization oven for 3 hours at 55° C. with rotation. The cell lysate was heat-inactivated for 45 minutes at 85° C. and stored at −20° C. prior to assaying.

Clonal HEK293 Cell Lines. Twin prime editing was used to generate single cell clones containing an att site at the adeno-associated virus integration site 1 (AAVS1) locus or Reverse Orientation Splice Acceptor 26 (ROSA26) locus. HEK293 cells were transfected with 450 ng PE5max and 150 ng of each epegRNA plasmid (a and b) in 24-well plates. Cells were serially diluted and visually confirmed to have a single colony per well. The presence of the att site was confirmed by droplet digital PCR. Transfections with clonal lines containing a preinserted att site used 360 ng of helper and 240 ng of donor. After 3 days, cells were lysed for analysis by droplet digital PCR.

Simultaneous Twin Prime Editing and Integration Assays in HEK293, HEK293T, HeLa, K562, and Primary Hepatocyte Cell Lines. HEK293, HEK293T, and HeLa cells ($1\times10^5$) were seeded in 24-well plates. The next day, wells were transfected with 300 ng of PE5max, 30 ng of each epegRNA, 120 ng of helper (integrase), and 120 ng of donor. K562 cells ($4\times10^6$) were seeded in 6-well plates. After 3 days, cells were lysed for analysis. All donor plasmids expressed DsRed. To reduce the influence of transfection efficiency, HEK293T, K562, and HeLa cells were sorted for DsRed to ensure uptake of the DNA.

Sample Preparation for Amplicon Sequencing. HEK293 cells were transfected with 600 ng of PE5max and 60 ng of each epegRNA plasmid (a and b). After 3 days, cells were lysed by incubating the pellets with 90 µL of Direct Lysis buffer supplemented with freshly prepared 1.0 mg/mL Proteinase K (Viagen Biotech) and incubation for 3 hours at 55° C. with rotation. The cell lysate was heat-inactivated for 45 minutes at 85° C. To determine editing outcomes using amplicon sequencing, a first round of PCR (PCR1) was performed using KOD One™ Blue polymerase (Toyobo), 0.3 µM of locus-specific barcoded primers containing a Nextera™ P5- and P7-tag (Table 4) and 1 µL of cell lysate in a total volume of 20 µL. An 8 bp barcode sequence was inserted between the Nextera™ tag sequence and the annealing sequence of the primers. PCR cycle conditions were 98° C. for 2 min followed by 30 cycles of 98° C. for 10 sec, 60° C. for 5 sec, and 68° C. for 5 sec with a final extension at 68° C. for 30 sec. Products from PCR1 were separated on a 2% gel in TAE (Tris-acetate-EDTA) buffer and fragments were extracted using the Zymo™ Gel DNA recovery Kit (Zymo). Eluted products were pooled in equimolar amounts and were submitted to the UC Davis DNA Technologies and Expression Analysis Core lab for a second round of PCR (PCR2) and amplicon sequencing.

TABLE 4

| Primer name | Sequence | SEQ ID NO: |
|---|---|---|
| NGS-AAV-1F | TCGTCGGCAGCGTCAGATGTGTATAAGAGACA G GATGACCTaactgcttctcctcttgggaag | 17 |
| NGS-AAV-2F | TCGTCGGCAGCGTCAGATGTGTATAAGAGACA G CTGTCTGTaactgcttctcctcttgggaag | 18 |
| NGS-AAV-3F | TCGTCGGCAGCGTCAGATGTGTATAAGAGACA G CACACAGTaactgcttctcctcttgggaag | 19 |
| NGS-AAV-4F | TCGTCGGCAGCGTCAGATGTGTATAAGAGACA G AACCGGTTaactgcttctcctcttgggaag | 20 |
| NGS-AAV-5F | TCGTCGGCAGCGTCAGATGTGTATAAGAGACA G TCTCTCAGaactgcttctcctcttgggaag | 21 |
| NGS-AAV-6F | TCGTCGGCAGCGTCAGATGTGTATAAGAGACA G GAGTCACTaactgcttctcctcttgggaag | 22 |
| NGS-AAV-25F | TCGTCGGCAGCGTCAGATGTGTATAAGAGACA G AGACTGAGaactgcttctcctcttgggaag | 23 |
| NGS-AAV-26F | TCGTCGGCAGCGTCAGATGTGTATAAGAGACA G GGAATACGaactgcttctcctcttgggaag | 24 |
| NGS-AAV-27F | TCGTCGGCAGCGTCAGATGTGTATAAGAGACA G AGACCTGTaactgcttctcctcttgggaag | 25 |
| NGS-AAV-28F | TCGTCGGCAGCGTCAGATGTGTATAAGAGACA G TAGGCGTTaactgcttctcctcttgggaag | 26 |
| NGS-AAV-29F | TCGTCGGCAGCGTCAGATGTGTATAAGAGACA G TGACGACTaactgcttctcctcttgggaag | 27 |
| NGS-AAV-7F | TCGTCGGCAGCGTCAGATGTGTATAAGAGACA G AGAGACTGaactgcttctcctcttgggaag | 28 |
| NGS-AAV-8F | TCGTCGGCAGCGTCAGATGTGTATAAGAGACA G ATATGCCGaactgcttctcctcttgggaag | 29 |
| NGS-AAV-9F | TCGTCGGCAGCGTCAGATGTGTATAAGAGACA G CCTACGAAcactaaggcaattggggtgc | 30 |
| NGS-AAV-10F | TCGTCGGCAGCGTCAGATGTGTATAAGAGACA G CGTAGGAAcactaaggcaattggggtgc | 31 |
| NGS-AAV-11F | TCGTCGGCAGCGTCAGATGTGTATAAGAGACA G CTCTGACTgccaggacggggctg | 32 |
| NGS-AAV-12F | TCGTCGGCAGCGTCAGATGTGTATAAGAGACA G GTCATCAGgccaggacggggctg | 33 |
| NGS-Xq22-1F | TCGTCGGCAGCGTCAGATGTGTATAAGAGACA G TCACTCTGaaggagaatgacagacaatagtatatatgaaat | 37 |
| NGS-Xq22-2F | TCGTCGGCAGCGTCAGATGTGTATAAGAGACA G CTGACAGTaaggagaatgacagacaatagtatatatgaaat | 35 |
| NGS-Xq22-3F | TCGTCGGCAGCGTCAGATGTGTATAAGAGACA G AGTGACAGaaggagaatgacagacaatagtatatatgaaat | 36 |
| NGS-Xq22-4F | TCGTCGGCAGCGTCAGATGTGTATAAGAGACA G ACCTACCTaaggagaatgacagacaatagtatatatgaaat | 37 |
| NGS-Xq22-5F | TCGTCGGCAGCGTCAGATGTGTATAAGAGACA G CATGTGGTaaggagaatgacagacaatagtatatatgaaat | 38 |
| NGS-Xq22-6F | TCGTCGGCAGCGTCAGATGTGTATAAGAGACA G TTCGTAGGaaggagaatgacagacaatagtatatatgaaat | 39 |
| NGS-Xq22-7F | TCGTCGGCAGCGTCAGATGTGTATAAGAGACA GGTCTTGAGaaggagaatgacagacaatagtatatatgaaat | 40 |
| NGS-Xq22-8F | TCGTCGGCAGCGTCAGATGTGTATAAGAGACA GACAGAGTGaaggagaatgacagacaatagtatatatgaaat | 41 |

TABLE 4-continued

| Primer name | Sequence | SEQ ID NO: |
|---|---|---|
| NGS-ROSA-1F | TCGTCGGCAGCGTCAGATGTGTATAAGAGACA<br>GTTCGAACGgtgaatgactaagctccatttccc | 42 |
| NGS-ROSA-2F | TCGTCGGCAGCGTCAGATGTGTATAAGAGACA<br>GGATGAGGTgtgaatgactaagctccatttccc | 43 |
| NGS-ROSA-3F | TCGTCGGCAGCGTCAGATGTGTATAAGAGACA<br>GCCTACGTTgtgaatgactaagctccatttccc | 44 |
| NGS-ROSA-4F | TCGTCGGCAGCGTCAGATGTGTATAAGAGACA<br>GGAGTTGAGgtgaatgactaagctccatttccc | 45 |
| NGS-ROSA-1F_2 | TCGTCGGCAGCGTCAGATGTGTATAAGAGACA<br>GTTCGAACGctccatttccctacccca | 46 |
| NGS-ROSA-2F_2 | TCGTCGGCAGCGTCAGATGTGTATAAGAGACA<br>GGATGAGGTctccatttccctacccca | 47 |
| NGS-ROSA-3F_2 | TCGTCGGCAGCGTCAGATGTGTATAAGAGACA<br>GCCTACGTTctccatttccctacccca | 48 |
| NGS-ROSA-4F_2 | TCGTCGGCAGCGTCAGATGTGTATAAGAGACA<br>GGAGTTGAGctccatttccctacccca | 49 |
| NGS-ROSA-5F | TCGTCGGCAGCGTCAGATGTGTATAAGAGACA<br>GGGTTCGATgggagggaagcactggttt | 50 |
| NGS-ROSA-6F | TCGTCGGCAGCGTCAGATGTGTATAAGAGACA<br>GATCGTTGGgggagggaagcactggttt | 51 |
| NGS-ROSA-7F | TCGTCGGCAGCGTCAGATGTGTATAAGAGACA<br>GAGACTCTGgagagggagaaagctagtgctat | 52 |
| NGS-ROSA-8F | TCGTCGGCAGCGTCAGATGTGTATAAGAGACA<br>GCAGTACTGgagagggagaaagctagtgctat | 53 |
| NGS-AAV-13R | GTCTCGTGGGCTCGGAGATGTGTATAAGAGAC<br>AGCATCCAAGccccatttcctggagcc | 54 |
| NGS-AAV-14R | GTCTCGTGGGCTCGGAGATGTGTATAAGAGAC<br>AGCGTTGGATccccatttcctggagcc | 55 |
| NGS-AAV-15R | GTCTCGTGGGCTCGGAGATGTGTATAAGAGAC<br>AGGATCTGGTccccatttcctggagcc | 56 |
| NGS-AAV-16R | GTCTCGTGGGCTCGGAGATGTGTATAAGAGAC<br>AGGTTCCTTGccccatttcctggagcc | 57 |
| NGS-AAV-17R | GTCTCGTGGGCTCGGAGATGTGTATAAGAGAC<br>AGCTAGTGGTccccatttcctggagcc | 58 |
| NGS-AAV-18R | GTCTCGTGGGCTCGGAGATGTGTATAAGAGAC<br>AGCAGTCAGTccccatttcctggagcc | 59 |
| NGS-AAV-30R | GTCTCGTGGGCTCGGAGATGTGTATAAGAGAC<br>AGGTGTACTGccccatttcctggagcc | 60 |
| NGS-AAV-31R | GTCTCGTGGGCTCGGAGATGTGTATAAGAGAC<br>AGGTTGTCCTccccatttcctggagcc | 61 |
| NGS-AAV-32R | GTCTCGTGGGCTCGGAGATGTGTATAAGAGAC<br>AGACCATGGTccccatttcctggagcc | 62 |
| NGS-AAV-33R | GTCTCGTGGGCTCGGAGATGTGTATAAGAGAC<br>AGCACAACTGccccatttcctggagcc | 63 |
| NGS-AAV-1F | TCGTCGGCAGCGTCAGATGTGTATAAGAGACA<br>GGATGACCTaactgcttctcctcttgggaag | 64 |
| NGS-AAV-2F | TCGTCGGCAGCGTCAGATGTGTATAAGAGACA<br>GCTGTCTGTaactgcttctcctcttgggaag | 65 |
| NGS-AAV-3F | TCGTCGGCAGCGTCAGATGTGTATAAGAGACA<br>GCACACAGTaactgcttctcctcttgggaag | 66 |

TABLE 4-continued

| Primer name | Sequence | SEQ ID NO: |
|---|---|---|
| NGS-AAV-4F | TCGTCGGCAGCGTCAGATGTGTATAAGAGACA GAACCGGTTaactgcttctcctcttgggaag | 67 |
| NGS-AAV-5F | TCGTCGGCAGCGTCAGATGTGTATAAGAGACA GTCTCTCAGaactgcttctcctcttgggaag | 68 |
| NGS-AAV-6F | TCGTCGGCAGCGTCAGATGTGTATAAGAGACA GGAGTCACTaactgcttctcctcttgggaag | 69 |
| NGS-AAV-25F | TCGTCGGCAGCGTCAGATGTGTATAAGAGACA GAGACTGAGaactgcttctcctcttgggaag | 70 |
| NGS-AAV-26F | TCGTCGGCAGCGTCAGATGTGTATAAGAGACA GGGAATACGaactgcttctcctcttgggaag | 71 |
| NGS-AAV-27F | TCGTCGGCAGCGTCAGATGTGTATAAGAGACA GAGACCTGTaactgcttctcctcttgggaag | 72 |
| NGS-AAV-28F | TCGTCGGCAGCGTCAGATGTGTATAAGAGACA GTAGGCGTTaactgcttctcctcttgggaag | 73 |
| NGS-AAV-29F | TCGTCGGCAGCGTCAGATGTGTATAAGAGACA GTGACGACTaactgcttctcctcttgggaag | 74 |
| NGS-AAV-7F | TCGTCGGCAGCGTCAGATGTGTATAAGAGACA GAGAGACTGaactgcttctcctcttgggaag | 75 |
| NGS-AAV-8F | TCGTCGGCAGCGTCAGATGTGTATAAGAGACA GATATGCCGaactgcttctcctcttgggaag | 76 |
| NGS-AAV-9F | TCGTCGGCAGCGTCAGATGTGTATAAGAGACA GCCTACGAAcactaaggcaattggggtgc | 77 |
| NGS-AAV-10F | TCGTCGGCAGCGTCAGATGTGTATAAGAGACA GCGTAGGAAcactaaggcaattggggtgc | 78 |
| NGS-AAV-11F | TCGTCGGCAGCGTCAGATGTGTATAAGAGACA GCTCTGACTgccaggacggggctg | 79 |
| NGS-AAV-12F | TCGTCGGCAGCGTCAGATGTGTATAAGAGACA GGTCATCAGgccaggacggggctg | 80 |
| NGS-Xq22-1F | TCGTCGGCAGCGTCAGATGTGTATAAGAGACA GTCACTCTGaaggagaatgacagacaatagtatatgaaat | 81 |
| NGS-Xq22-2F | TCGTCGGCAGCGTCAGATGTGTATAAGAGACA GCTGACAGTaaggagaatgacagacaatagtatatgaaat | 82 |
| NGS-Xq22-3F | TCGTCGGCAGCGTCAGATGTGTATAAGAGACA GAGTGACAGaaggagaatgacagacaatagtatatgaaat | 83 |
| NGS-Xq22-4F | TCGTCGGCAGCGTCAGATGTGTATAAGAGACA GACCTACCTaaggagaatgacagacaatagtatatgaaat | 84 |
| NGS-Xq22-5F | TCGTCGGCAGCGTCAGATGTGTATAAGAGACA GCATGTGGTaaggagaatgacagacaatagtatatgaaat | 85 |
| NGS-Xq22-6F | TCGTCGGCAGCGTCAGATGTGTATAAGAGACA GTTCGTAGGaaggagaatgacagacaatagtatatgaaat | 86 |
| NGS-Xq22-7F | TCGTCGGCAGCGTCAGATGTGTATAAGAGACA GGTCTTGAGaaggagaatgacagacaatagtatatgaaat | 87 |
| NGS-Xq22-8F | TCGTCGGCAGCGTCAGATGTGTATAAGAGACA GACAGAGTGaaggagaatgacagacaatagtatatgaaat | 88 |
| NGS-ROSA-1F | TCGTCGGCAGCGTCAGATGTGTATAAGAGACA GTTCGAACGgtgaatgactaagctccatttccc | 89 |
| NGS-ROSA-2F | TCGTCGGCAGCGTCAGATGTGTATAAGAGACA GGATGAGGTgtgaatgactaagctccatttccc | 90 |
| NGS-ROSA-3F | TCGTCGGCAGCGTCAGATGTGTATAAGAGACA GCCTACGTTgtgaatgactaagctccatttccc | 91 |

TABLE 4-continued

| Primer name | Sequence | SEQ ID NO: |
|---|---|---|
| NGS-ROSA-4F | TCGTCGGCAGCGTCAGATGTGTATAAGAGACA GGAGTTGAGgtgaatgactaagctccatttccc | 92 |
| NGS-ROSA-1F_2 | TCGTCGGCAGCGTCAGATGTGTATAAGAGACA GTTCGAACGctccatttccctacccca | 93 |
| NGS-ROSA-2F_2 | TCGTCGGCAGCGTCAGATGTGTATAAGAGACA GGATGAGGTctccatttccctacccca | 94 |
| NGS-ROSA-3F_2 | TCGTCGGCAGCGTCAGATGTGTATAAGAGACA GCCTACGTTctccatttccctacccca | 95 |
| NGS-ROSA-4F_2 | TCGTCGGCAGCGTCAGATGTGTATAAGAGACA GGAGTTGAGctccatttccctacccca | 96 |
| NGS-ROSA-5F | TCGTCGGCAGCGTCAGATGTGTATAAGAGACA GGGTTCGATgggagggaagcactggttt | 97 |
| NGS-ROSA-6F | TCGTCGGCAGCGTCAGATGTGTATAAGAGACA GATCGTTGGgggagggaagcactggttt | 98 |
| NGS-ROSA-7F | TCGTCGGCAGCGTCAGATGTGTATAAGAGACA GAGACTCTGgagagggagaaagctagtgctat | 99 |
| NGS-ROSA-8F | TCGTCGGCAGCGTCAGATGTGTATAAGAGACA GCAGTACTGgagagggagaaagctagtgctat | 100 |
| NGS-AAV-13R | GTCTCGTGGGCTCGGAGATGTGTATAAGAGAC AGCATCCAAGccccatttcctggagcc | 101 |
| NGS-AAV-14R | GTCTCGTGGGCTCGGAGATGTGTATAAGAGAC AGCGTTGGATccccatttcctggagcc | 102 |
| NGS-AAV-15R | GTCTCGTGGGCTCGGAGATGTGTATAAGAGAC AGGATCTGGTccccatttcctggagcc | 103 |
| NGS-AAV-16R | GTCTCGTGGGCTCGGAGATGTGTATAAGAGAC AGGTTCCTTGccccatttcctggagcc | 104 |
| NGS-AAV-17R | GTCTCGTGGGCTCGGAGATGTGTATAAGAGAC AGCTAGTGGTccccatttcctggagcc | 105 |
| NGS-AAV-18R | GTCTCGTGGGCTCGGAGATGTGTATAAGAGAC AGCAGTCAGTccccatttcctggagcc | 106 |
| NGS-AAV-30R | GTCTCGTGGGCTCGGAGATGTGTATAAGAGAC AGGTGTACTGccccatttcctggagcc | 107 |
| NGS-AAV-31R | GTCTCGTGGGCTCGGAGATGTGTATAAGAGAC AGGTTGTCCTccccatttcctggagcc | 108 |
| NGS-AAV-32R | GTCTCGTGGGCTCGGAGATGTGTATAAGAGAC AGACCATGGTccccatttcctggagcc | 109 |
| NGS-AAV-33R | GTCTCGTGGGCTCGGAGATGTGTATAAGAGAC AGCACAACTGccccatttcctggagcc | 110 |
| NGS-AAV-34R | GTCTCGTGGGCTCGGAGATGTGTATAAGAGAC AGCTCTCTCTccccatttcctggagcc | 111 |
| NGS-AAV-19R | GTCTCGTGGGCTCGGAGATGTGTATAAGAGAC AGTAGGAACGccccatttcctggagcc | 112 |
| NGS-AAV-20R | GTCTCGTGGGCTCGGAGATGTGTATAAGAGAC AGTCTCCAGTccccatttcctggagcc | 113 |
| NGS-AAV-21R | GTCTCGTGGGCTCGGAGATGTGTATAAGAGAC AGAGTCGACTgcctagttttagcactgaaaccc | 114 |
| NGS-AAV-22R | GTCTCGTGGGCTCGGAGATGTGTATAAGAGAC AGAACGTAGGgcctagttttagcactgaaaccc | 115 |
| NGS-AAV-23R | GTCTCGTGGGCTCGGAGATGTGTATAAGAGAC AGACTGGACTggccaccctgcgctac | 116 |

TABLE 4-continued

| Primer name | Sequence | SEQ ID NO: |
|---|---|---|
| NGS-AAV-24R | GTCTCGTGGGCTCGGAGATGTGTATAAGAGAC AGACTCACAGggccaccctgcgctac | 117 |
| NGS-Xq22-9R | GTCTCGTGGGCTCGGAGATGTGTATAAGAGAC AGCTACGTAGcccaggttacatttggttgatatgtc | 118 |
| NGS-Xq22-10R | GTCTCGTGGGCTCGGAGATGTGTATAAGAGAC AGTTCCGGTTcccaggttacatttggttgatatgtc | 119 |
| NGS-Xq22-11R | GTCTCGTGGGCTCGGAGATGTGTATAAGAGAC AGGACATGAGcaggtattttaaatggtccccagg | 120 |
| NGS-Xq22-12R | GTCTCGTGGGCTCGGAGATGTGTATAAGAGAC AGCAACCATGcaggtattttaaatggtccccagg | 121 |
| NGS-Xq22-13R | GTCTCGTGGGCTCGGAGATGTGTATAAGAGAC AGACACCTCTcaggtattttaaatggtccccagg | 122 |
| NGS-Xq22-14R | GTCTCGTGGGCTCGGAGATGTGTATAAGAGAC AGCTCAACAGcaggtattttaaatggtccccagg | 123 |
| NGS-Xq22-15R | GTCTCGTGGGCTCGGAGATGTGTATAAGAGAC AGACGTTGGTcaggtattttaaatggtccccagg | 124 |
| NGS-Xq22-16R | GTCTCGTGGGCTCGGAGATGTGTATAAGAGAC AGAACGATGGcaggtattttaaatggtccccagg | 125 |
| NGS-ROSA-9R | GTCTCGTGGGCTCGGAGATGTGTATAAGAGAC AGACTGTGTGagaagaggtcagaaagccagtc | 126 |
| NGS-ROSA-10R | GTCTCGTGGGCTCGGAGATGTGTATAAGAGAC AGTGGTGAAGagaagaggtcagaaagccagtc | 127 |
| NGS-ROSA-11R | GTCTCGTGGGCTCGGAGATGTGTATAAGAGAC AGCTTCTCCTagaagaggtcagaaagccagtc | 128 |
| NGS-ROSA-12R | GTCTCGTGGGCTCGGAGATGTGTATAAGAGAC AGGAGTGTCTagaagaggtcagaaagccagtc | 129 |
| NGS-R_2OSA-9R_2 | GTCTCGTGGGCTCGGAGATGTGTATAAGAGAC AGACTGTGTGgtcagaaagccagtcgcg | 130 |
| NGS-R_2OSA-10R_2 | GTCTCGTGGGCTCGGAGATGTGTATAAGAGAC AGTGGTGAAGgtcagaaagccagtcgcg | 131 |
| NGS-R_2OSA-11R_2 | GTCTCGTGGGCTCGGAGATGTGTATAAGAGAC AGCTTCTCCTgtcagaaagccagtcgcg | 132 |
| NGS-R_2OSA-12R_2 | GTCTCGTGGGCTCGGAGATGTGTATAAGAGAC AGGAGTGTCTgtcagaaagccagtcgcg | 133 |
| NGS-ROSA-13R | GTCTCGTGGGCTCGGAGATGTGTATAAGAGAC AGTCTCAGAGggttattgtaataagggtggggtagg | 134 |
| NGS-ROSA-14R | GTCTCGTGGGCTCGGAGATGTGTATAAGAGAC AGCAGTTCAGggttattgtaataagggtggggtagg | 135 |
| NGS-ROSA-15R | GTCTCGTGGGCTCGGAGATGTGTATAAGAGAC AGAGTGCACTcctgagttttataccatttgagaccc | 136 |
| NGS-ROSA-16R | GTCTCGTGGGCTCGGAGATGTGTATAAGAGAC AGACCTAGGTcctgagttttataccatttgagaccc | 137 |
| NGS-ROSA-1F | TCGTCGGCAGCGTCAGATGTGTATAAGAGACA GTTCGAACGgtgaatgactaagctccatttccc | 138 |
| NGS-ROSA-2F | TCGTCGGCAGCGTCAGATGTGTATAAGAGACA GGATGAGGTgtgaatgactaagctccatttccc | 139 |
| NGS-ROSA-3F | TCGTCGGCAGCGTCAGATGTGTATAAGAGACA GCCTACGTTgtgaatgactaagctccatttccc | 140 |
| NGS-ROSA-4F | TCGTCGGCAGCGTCAGATGTGTATAAGAGACA GGAGTTGAGgtgaatgactaagctccatttccc | 141 |

TABLE 4-continued

| Primer name | Sequence | SEQ ID NO: |
|---|---|---|
| NGS-ROSA-1F_2 | TCGTCGGCAGCGTCAGATGTGTATAAGAGACA GTTCGAACGctccatttccctacccca | 142 |
| NGS-ROSA-2F_2 | TCGTCGGCAGCGTCAGATGTGTATAAGAGACA GGATGAGGTctccatttccctacccca | 143 |
| NGS-ROSA-3F_2 | TCGTCGGCAGCGTCAGATGTGTATAAGAGACA GCCTACGTTctccatttccctacccca | 144 |
| NGS-ROSA-4F_2 | TCGTCGGCAGCGTCAGATGTGTATAAGAGACA GGAGTTGAGctccatttccctacccca | 145 |
| NGS-ROSA-9R | GTCTCGTGGGCTCGGAGATGTGTATAAGAGAC AGACTGTGTGagaagaggtcagaaagccagtc | 146 |
| NGS-ROSA-10R | GTCTCGTGGGCTCGGAGATGTGTATAAGAGAC AGTGGTGAAGagaagaggtcagaaagccagtc | 147 |
| NGS-ROSA-11R | GTCTCGTGGGCTCGGAGATGTGTATAAGAGAC AGCTTCTCCTagaagaggtcagaaagccagtc | 148 |
| NGS-ROSA-12R | GTCTCGTGGGCTCGGAGATGTGTATAAGAGAC AGGAGTGTCTagaagaggtcagaaagccagtc | 149 |
| NGS-R_2OSA-9R_2 | GTCTCGTGGGCTCGGAGATGTGTATAAGAGAC AGACTGTGTGgtcagaaagccagtcgcg | 150 |
| NGS-R_2OSA-10R_2 | GTCTCGTGGGCTCGGAGATGTGTATAAGAGAC AGTGGTGAAGgtcagaaagccagtcgcg | 151 |
| NGS-R_2OSA-11R_2 | GTCTCGTGGGCTCGGAGATGTGTATAAGAGAC AGCTTCTCCTgtcagaaagccagtcgcg | 152 |
| NGS-R_2OSA-12R_2 | GTCTCGTGGGCTCGGAGATGTGTATAAGAGAC AGGAGTGTCTgtcagaaagccagtcgcg | 153 |
| SG Rosa 1a + 1b For | gtgaatgactaagctccatttccc | 154 |
| SG Rosa 1a + 1b rev | agaagaggtcagaaagccagtc | 155 |
| SG Rosa 1a + 1b For 2 | ctccatttccctacccca | 156 |
| SG Rosa 1a + 1b rev2 | gtcagaaagccagtcgcg | 157 |
| SG Rosa 1a + 1b For 3 | ccctaccccacccttattaca | 158 |
| SG Rosa 1a + 1b rev 3 | gaggtcagaaagccagtcgc | 159 |

Analysis of Amplicon Sequencing Data. Amplicon sequencing results were first demultiplexed using Ultraplex (Wilkins et al. (2021) *Wellcome Open Res.* 6:141) based on barcodes allowing one barcode mismatch. The barcode sequences were trimmed, and low-quality reads were discarded using a q-score of 20 (default is 30). To sort the forward and reverse reads in the same order, the sequences were re-paired with the repair function in BBtools. Editing and indel frequencies were determined as previously described (Doman et al. (2022) *Nat. Protoc.* 17:2431-2468). Briefly, CRISPResso2 was run in HDR mode, discard_indel_reads flag was on and quantification window coordinates were set to 10 base pairs upstream of each nick site. Unedited template and PE sequences were input. Data from the "CRISPResso_quantification_of_editing_frequency" file was used to determine editing frequency by dividing "Read-aligned" (in the HDR tab) by "Reads_aligned_all_amplicons". The indel frequency was determined by dividing total discarded reads (Reference+HDR) by "Reads_aligned_all_amplicons". Examples of prime editing sequences as well as primers are provided in Table 5.

TABLE 5

| Target | Sequence | SEQ ID NO: |
|---|---|---|
| AAV 1a + 1b (Unedited) | CACTAAGGCAATTGGGGTGCAGGAATGGGGCAGGG TACCAGCCTCACCAAGTGGTTGATAAACCCACGTGG GGTACCCTAAGAACTTGGGAACAGCCACAGCAGGGG | 160 |

TABLE 5-continued

| Target | Sequence | SEQ ID NO: |
|---|---|---|
| | GGCGATGCTTGGGGACCTGCCTGGAGAAGGATGCAG GACGAGAAACACAGCCCCAGGTGGAGAAACTGGCC GGGAATCAAGAGTCACCCAGAGACAGTGACCAACCA TCCCTGTTTTCCTAGGACTGAGGGTTTCAGTGCTAAA ACTAGGC | |
| AAV 1a + 1b attB35 | CACTAAGGCAATTGGGGTGCAGGAATGGGGGCAGGG TACCAGCCTCACCAAGTGGTTGATAAACCCGTGCCA GGGCGTGCCCTTGGGCTCCCCGGGCGCGTGTGGAGA AACTGGCCGGGAATCAAGAGTCACCCAGAGACAGTG ACCAACCATCCCTGTTTTCCTAGGACTGAGGGTTTCA GTGCTAAAACTAGGC | 161 |
| AAV 1a + 1b attP41 | CACTAAGGCAATTGGGGTGCAGGAATGGGGGCAGGG TACCAGCCTCACCAAGTGGTTGATAAACCCGCCCCC AACTGAGAGAACTCAAAGGTTACCCCAGTTGGGGCG TGGAGAAACTGGCCGGGAATCAAGAGTCACCCAGAG ACAGTGACCAACCATCCCTGTTTTCCTAGGACTGAGG GTTTCAGTGCTAAAACTAGGC | 162 |
| AAV 2a + 2b (Un-edited) | GCCAGGACGGGGCTGGCTACTGGCCTTATCTCACAG GTAAAACTGACGCACGGAGGAACAATATAAATTGGG GACTAGAAAGGTGAAGAGCCAAAGTTAGAACTCAGG ACCAACTTATTCTGATTTTGTTTTTCCAAACTGCTTCT CCTCTTGGGAAGTGTAAGGAAGCTGCAGCACCAGGA TCAGTGAAACGCACCAGACAGCCGCGTCAGAGCAGC TCAGGTTCTGGGAGAGGGTAGCGCAGGGTGGCC | 163 |
| AAV 2a + 2b attB35 | GCCAGGACGGGGCTGGCTACTGGCCTTATCTCACAG GTAAAACTGACGCAGTGCCAGGGCGTGCCCTTGGGC TCCCCGGGCGCGTGGGAAGTGTAAGGAAGCTGCAGC ACCAGGATCAGTGAAACGCACCAGACAGCCGTCA GAGCAGCTCAGGTTCTGGGAGAGGGTAGCGCAGGGT GGCC | 164 |
| AAV 2a + 2b attP41 | GCCAGGACGGGGCTGGCTACTGGCCTTATCTCACAG GTAAAACTGACGCAGCCCCAACTGAGAGAACTCAA AGGTTACCCCAGTTGGGGGGGAAGTGTAAGGAAGC TGCAGCACCAGGATCAGTGAAACGCACCAGACAGCC GCGTCAGAGCAGCTCAGGTTCTGGGAGAGGGTAGCG CAGGGTGGCC | 165 |
| AAV 3a + 3b (Un-edited) | AACTGCTTCTCCTCTTGGGAAGTGTAAGGAAGCTGCA GCACCAGGATCAGTGAAACGCACCAGACAGCCGCGT CAGAGCAGCTCAGGTTCTGGGAGAGGGTAGCGCAGG GTGGCCACTGAGAACCGGGCAGGTCACGCATCCCCC CCTTCCCTCCCACCCCCTGCCAAGCTCTCCCTCCCAG GATCCTCTCTGGCTCCATCGTAAGCAAACCTTAGAGG TTCTGGCAAGGAGAGAGATGGCTCCAGGAAATGGGGG | 166 |
| AAV 3a + 3b (Liu lab) attP | AACTGCTTCTCCTCTTGGGAAGTGTAAGGAAGCTGCA GCACCAGGATCAGTGAAACGCACCAGGTTTGTCTGG TCAACCACCGCGGTCTCAGTGGTGTACGGTACAAAC CTCCTCTCTGGCTCCATCGTAAGCAAACCTTAGAGGT TCTGGCAAGGAGAGAGATGGCTCCAGGAAATGGGGG | 167 |
| AAV 3a + 3b attB35 | AACTGCTTCTCCTCTTGGGAAGTGTAAGGAAGCTGCA GCACCAGGATCAGTGAAACGCACCGTGCCAGGGCGT GCCCTTGGGCTCCCCGGGCGCGTTCCTCTCTGGCTCC ATCGTAAGCAAACCTTAGAGGTTCTGGCAAGGAGAG AGATGGCTCCAGGAAATGGGGG | 168 |
| AAV 3a + 3b attP41 | AACTGCTTCTCCTCTTGGGAAGTGTAAGGAAGCTGCA GCACCAGGATCAGTGAAACGCACCGCCCCCAACTGA GAGAACTCAAAGGTTACCCCAGTTGGGGCTCCTCTCT GGCTCCATCGTAAGCAAACCTTAGAGGTTCTGGCAA GGAGAGAGATGGCTCCAGGAAATGGGGG | 169 |
| AAV 4a + 3b (Un-edited) | AACTGCTTCTCCTCTTGGGAAGTGTAAGGAAGCTGCA GCACCAGGATCAGTGAAACGCACCAGACAGCCGCGT CAGAGCAGCTCAGGTTCTGGGAGAGGGTAGCGCAGG GTGGCCACTGAGAACCGGGCAGGTCACGCATCCCCC CCTTCCCTCCCACCCCCTGCCAAGCTCTCCCTCCCAG GATCCTCTCTGGCTCCATCGTAAGCAAACCTTAGAGG TTCTGGCAAGGAGAGAGATGGCTCCAGGAAATGGGGG | 170 |
| AAV 4a + 3b (Liu lab) attP | AACTGCTTCTCCTCTTGGGAAGTGTAAGGAAGCTGCA GCACCAGGATCAGTGAAACGCACCAGACAGCCGCGT | 171 |

TABLE 5-continued

| Target | Sequence | SEQ ID NO: |
|---|---|---|
| | CAGAGCAGCTCAGGTTCTGGGAGGTTTGTCTGGTCA<br>ACCACCGCGGTCTCAGTGGTGTACGGTACAAACCTC<br>CTCTCTGGCTCCATCGTAAGCAAACCTTAGAGGTTCT<br>GGCAAGGAGAGAGATGGCTCCAGGAAATGGGGG | |
| AAV 4a + 3b<br>attB35 | AACTGCTTCTCCTCTTGGGAAGTGTAAGGAAGCTGCA<br>GCACCAGGATCAGTGAAACGCACCAGACAGCCGCGT<br>CAGAGCAGCTCAGGTTCTGGGGTGCCAGGGCGTGCC<br>CTTGGGCTCCCCGGGCGCGTTCCTCTCTGGCTCCATC<br>GTAAGCAAACCTTAGAGGTTCTGGCAAGGAGAGAGA<br>TGGCTCCAGGAAATGGGGG | 172 |
| AAV 4a + 3b<br>attP41 | AACTGCTTCTCCTCTTGGGAAGTGTAAGGAAGCTGCA<br>GCACCAGGATCAGTGAAACGCACCAGACAGCCGCGT<br>CAGAGCAGCTCAGGTTCTGGGGCCCCCAACTGAGAG<br>AACTCAAAGGTTACCCCAGTTGGGGCTCCTCTCTGGC<br>TCCATCGTAAGCAAACCTTAGAGGTTCTGGCAAGGA<br>GAGAGATGGCTCCAGGAAATGGGGG | 173 |
| Rosa 3a + 3b (Un-<br>edited) | GGGAGGGAAGCACTGGTTTCTCAAGCAAAAGCTAAA<br>ATTTTTCTATTAAGATTTAACCTGATGCTACACTTTGGT<br>GGTGCAGCAAGGGTCTCAAATGGTATAAAACTCAGGT<br>GATCATGCTTTATGTCTGTCTAGAAAAATGCTCCAA<br>AAATGATAAGTAGTGATAATCCGCAGTCTCGTTGCATA<br>AAATCAGCCCCAGGTGAATGACTAAGCTCCATTTCCC<br>TACCCCACCCTTATTACAATAACC | 174 |
| Rosa 3a + 3b<br>attB35 | GGGAGGGAAGCACTGGTTTCTCAAGCAAAAGCTAAA<br>ATTTTTCTATTAAGATTTAACCTGATGCTACACTTTGGT<br>GGTGCAGCAAGGGTCTCAAATGGTATAAAGTGCCA<br>GGGCGTGCCCTTGGGCTCCCCGGGCGCGTGTGAATG<br>ACTAAGCTCCATTTCCCTACCCCACCCTTATTACAATA<br>ACC | 175 |
| Rosa 3a + 3b<br>attP41 | GGGAGGGAAGCACTGGTTTCTCAAGCAAAAGCTAAA<br>ATTTTTCTATTAAGATTTAACCTGATGCTACACTTTGGT<br>GGTGCAGCAAGGGTCTCAAATGGTATAAAAGCCCCCA<br>ACTGAGAGAACTCAAAGGTTACCCCAGTTGGGGCGT<br>GAATGACTAAGCTCCATTTCCCTACCCCACCCTTATTA<br>CAATAACC | 176 |
| Rosa 4a + 4b (Un-<br>edited) | GAGAGGGAGAAAGCTAGTGCTATGTCTGAATACTAGA<br>GGAGCAAGTACAACAAATGGAAAATGGGATCAAGTA<br>TGAGTGAGAGTTGCTAAGATGCCTGGTAGGGATGCAA<br>AGGGGTAGAGAGCCTGGGGAGAGAGGGTGAGGGAG<br>GGAAGCACTGGTTTCTCAAGCAAAAGCTAAAATTTTT<br>CTATTAAGATTTAACCTGATGCTACACTTTGGTGGTGC<br>AGCAAGGGTCTCAAATGGTATAAAACTCAGG | 177 |
| Rosa 4a + 4b<br>attB35 | GAGAGGGAGAAAGCTAGTGCTATGTCTGAATACTAGA<br>GGAGCAAGTACAACAAATGGAAAATGGGATCAAGTA<br>TGAGTGAGAGTTGCTAAGATGCCTGGTAGGGATGCGT<br>GCCAGGGCGTGCCCTTGGGCTCCCCGGGCGCGTGCTA<br>CACTTTGGTGGTGCAGCAAGGGTCTCAAATGGTATAA<br>AACTCAGG | 178 |
| Rosa 4a + 4b<br>attP41 | GAGAGGGAGAAAGCTAGTGCTATGTCTGAATACTAGA<br>GGAGCAAGTACAACAAATGGAAAATGGGATCAAGTA<br>TGAGTGAGAGTTGCTAAGATGCCTGGTAGGGATGCGC<br>CCCCAACTGAGAGAACTCAAAGGTTACCCCAGTTGG<br>GGCGCTACACTTTGGTGGTGCAGCAAGGGTCTCAAAT<br>GGTATAAAACTCAGG | 179 |
| Xq22 1a + 1b (Un-<br>edited) | AAGGAGAATGACAGACAATAGTATATATGAAATATTCT<br>TATCAAAAGATAAGATCTACTCTAATTAAACCTGTAGG<br>GAAAAAAGGGACAAAGGAGCATGTTAAACAATATCA<br>TGAGAATAGAATGAGCAAACTCTAGAATGTGGGAAA<br>CTTAGGAAGACACCCAGTTTCTTCAACAAAAAAATTG<br>CAAAAATAAAAAGGAACAAGGAGAACCTATAGATTA<br>AATGAGGCATTAAAGACATATCAACCAAATGTAACCT<br>GGG | 180 |
| Xq22 1a + 1b<br>attB35 | AAGGAGAATGACAGACAATAGTATATATGAAATATTCT<br>TATCAAAAGATAAGATCTACTCTAATTAAACCTGTGCC<br>AGGGCGTGCCCTTGGGCTCCCCGGGCGCGTGATTAAA<br>TGAGGCATTAAAGACATATCAACCAAATGTAACCTGGG | 181 |

TABLE 5-continued

| Target | Sequence | SEQ ID NO: |
|---|---|---|
| Xq22 1a + 1b attP41 | AAGGAGAATGACAGACAATAGTATATATGAAATATTCT TATCAAAAGATAAGATCTACTCTAATTAAACCTGCCCC CAACTGAGAGAACTCAAAGGTTACCCCAGTTGGGGC GATTAAATGAGGCATTAAAGACATATCAACCAAATGTA ACCTGGG | 182 |
| Xq22 1a + 2b (Unedited) | AAGGAGAATGACAGACAATAGTATATATGAAATATTCT TATCAAAAGATAAGATCTACTCTAATTAAACCTGTAGG GAAAAAAGGGACAAAGGAGCATGTTAAACAATATCA TGAGAATAGAATGAGCAAACTCTAGAATGTGGGAAA CTTAGGAAGACACCCAGTTTCTTCAACAAAAAAATTG CAAAAATAAAAAGGAACAAGGAGAACCTATAGATTA AATGAGGCATTAAAGACATATCAACCAAATGTAACCT GGGGACCATTTAAAATACCTG | 183 |
| Xq22 1a + 2b attB35 | AAGGAGAATGACAGACAATAGTATATATGAAATATTCT TATCAAAAGATAAGATCTACTCTAATTAAACCTGTGCC AGGGCGTGCCCTTGGGCTCCCCGGGCGCGTGTAACCT GGGGACCATTTAAAATACCTG | 184 |
| Xq22 1a + 2b attP41 | AAGGAGAATGACAGACAATAGTATATATGAAATATTCT TATCAAAAGATAAGATCTACTCTAATTAAACCTGCCCC CAACTGAGAGAACTCAAAGGTTACCCCAGTTGGGGC GTAACCTGGGGACCATTTAAAATACCTG | 185 |
| Xq22 2a + 1b (Unedited) | AAGGAGAATGACAGACAATAGTATATATGAAATATTCT TATCAAAAGATAAGATCTACTCTAATTAAACCTGTAGG GAAAAAAGGGACAAAGGAGCATGTTAAACAATATCA TGAGAATAGAATGAGCAAACTCTAGAATGTGGGAAA CTTAGGAAGACACCCAGTTTCTTCAACAAAAAAATTG CAAAAATAAAAAGGAACAAGGAGAACCTATAGATTA AATGAGGCATTAAAGACATATCAACCAAATGTAACCT GGGGACCATTTAAAATACCTG | 186 |
| Xq22 2a + 1b attB35 | AAGGAGAATGACAGACAATAGTATATATGAAATATTCT TATCAAAAGATAAGATCTACTCTAATTAAACCTGTAGG GAAAAAAGGGACAAAGGAGCATGTTAAACAATATCA TGAGAATAGAATGAGCAAACTCTAGAGTGCCAGGGC GTGCCCTTGGGCTCCCCGGGCGCGTGATTAAATGAGG CATTAAAGACATATCAACCAAATGTAACCTGGGGACC ATTTAAAATACCTG | 187 |
| Xq22 2a + 1b attP41 | AAGGAGAATGACAGACAATAGTATATATGAAATATTCT TATCAAAAGATAAGATCTACTCTAATTAAACCTGTAGG GAAAAAAGGGACAAAGGAGCATGTTAAACAATATCA TGAGAATAGAATGAGCAAACTCTAGAGCCCCCAACTG AGAGAACTCAAAGGTTACCCCAGTTGGGGCGATTAA ATGAGGCATTAAAGACATATCAACCAAATGTAACCTG GGGACCATTTAAAATACCTG | 188 |
| Xq22 2a + 2b (Unedited) | AAGGAGAATGACAGACAATAGTATATATGAAATATTCT TATCAAAAGATAAGATCTACTCTAATTAAACCTGTAGG GAAAAAAGGGACAAAGGAGCATGTTAAACAATATCA TGAGAATAGAATGAGCAAACTCTAGAATGTGGGAAA CTTAGGAAGACACCCAGTTTCTTCAACAAAAAAATTG CAAAAATAAAAAGGAACAAGGAGAACCTATAGATTA AATGAGGCATTAAAGACATATCAACCAAATGTAACCT GGGGACCATTTAAAATACCTG | 189 |
| Xq22 2a + 2b attB35 | AAGGAGAATGACAGACAATAGTATATATGAAATATTCT TATCAAAAGATAAGATCTACTCTAATTAAACCTGTAGG GAAAAAAGGGACAAAGGAGCATGTTAAACAATATCA TGAGAATAGAATGAGCAAACTCTAGAGTGCCAGGGC GTGCCCTTGGGCTCCCCGGGCGCGTGTAACCTGGGGA CCATTTAAAATACCTG | 190 |
| Xq22 2a + 2b attP41 | AAGGAGAATGACAGACAATAGTATATATGAAATATTCT TATCAAAAGATAAGATCTACTCTAATTAAACCTGTAGG GAAAAAAGGGACAAAGGAGCATGTTAAACAATATCA TGAGAATAGAATGAGCAAACTCTAGAGCCCCCAACTG AGAGAACTCAAAGGTTACCCCAGTTGGGGCGTAACC TGGGGACCATTTAAAATACCTG | 191 |

Droplet Digital PCR (ddPCR) Protocol. ddPCR was performed according to manufacturer's instructions (BioRad Laboratories). Briefly, each reaction (22 μL) contained 1.0 μL of cell lysate (1:1 dilution in water), 11 μL of 2× ddPCR Supermix for Probes (no dUTP), 10 U XhoI (New England Biolabs), primers (Table 6) for target and reference at 900 nM and probes at 250 nM. The plate was sealed with PX1 PCR Plate Sealer (BioRad), vortexed thoroughly to mix, and centrifuged 1 minute at 1000 rpm prior to droplet generation using the QX200 AutoDG Droplet Generator System (Bio-Rad). PCR was performed as follows: denaturation at 95° C. for 10 min, 45 cycles of 95° C. for 30 sec, 60° C. for 2 mi and 72° C. for 2 mi, followed by a final incubation at 98° C. for 10 min. Droplets were read on a QX200 Droplet Reader (BioRad) and analyzed using QX Manager 1.2 Standard Edition software (BioRad).

TABLE 6

| Primer | Sequence | SEQ ID NO: |
|---|---|---|
| ddPCR pCMV Rev | gtttgtccaaactcagcggc | 192 |
| ddPCR pCMV OPP Rev | gaaggtacgcctgcaggtac | 193 |
| ddPCR pCMV OPP Rev2 | atccagcctccggactctag | 194 |
| ddPCR attB35 Rev | ccggggagcccaaggg | 195 |
| ddPCR attP41 Rev | gagttctctcagttggggc | 196 |
| ddPCR attP41 Rev2 | ccaactggggtaacctttgagt | 197 |
| ddPCR Rosa1a For | tccgcagtctcgttgcataa | 198 |
| ddPCR Rosa3a For | acaacaaatggaaaatgggatca | 199 |
| ddPCR Rosa3a For2 | agaacgtgaactagggagga | 200 |
| ddPCR Xq1a For | agcctctatattctaatccacttgt | 201 |
| ddPCR Xq1a For2 | ctgtgcctagcctaagcctc | 202 |
| ddPCR Xq1a For3 | tgctggaattacaggcgtga | 203 |
| ddPCR AAV3a For | gcttctcctcttgggaagtgtaa | 204 |
| ddPCR AAV2a For | aagggagttttccacacgga | 205 |
| ddPCR AAV1a For | cactaaggcaattggggtgc | 206 |
| ddPCR BxBI attB38 Rev | gtcgacgacggcggtctc | 207 |
| ddPCR BxBI attB38 Rev2 | ctccgtcgtcaggatcatcc | 208 |
| ddPCR BxBI attP48 Rev | gtacaccactgagaccgcg | 209 |
| ddPCR Pa01 attB33 Rev | ccgtgacctacatgctcgc | 210 |
| ddPCR Pa01 attB33 Rev2 | ctcgaagggcgtatgcgc | 211 |
| ddPCR Rosa1a Probe | ccccaggtgaatgactaagctccatttccctac | 212 |
| Opti Rosa1a Probe | ggggagtgagcagctgtaag | 213 |
| ddPCR Rosa3a Probe | agtgagagttgctaagatgcctggtagggatgc | 214 |
| Opti Rosa3a Probe | tgctgcaccaccaaagtgta | 215 |
| ddPCR Xq1a Probe | tagggccctgatatgggcacccaaatgtagctt | 216 |
| Opti Xq1a Probe | aacatgctcctttgtcccctt | 217 |
| ddPCR AAV3a Probe | ctgcagcaccaggatcagtgaaacgcac | 218 |
| Opti AAV3a Probe | gttctcagtggccaccctg | 219 |
| ddPCR AAV2a Probe | cccctcctcaccacagccctgcca | 220 |
| Opti AAV2a Probe | ggctcttcacctttctagtccc | 221 |
| ddPCR AAV1a Probe | taccagcctcaccaagtggttgataaacccacg | 222 |
| Opti AAV1a Probe | ctcgtcctgcatccttctcc | 223 |
| ACTB For | acactgtgcccatctctac | 224 |
| ACTB Rev | aatgtcacgcacgatttc | 225 |

TABLE 6-continued

| Primer | Sequence | SEQ ID NO: |
|---|---|---|
| RPP30 For | agatttggacctgcgagcg | 226 |
| RPP30 Rev | gagcggctgtctccacaagt | 227 |
| UBE2D2 For | gtactcttgtccatctgttctctg | 228 |
| UBE2D2 Rev2 | ggccgatattcagcccttaaac | 229 |

Phage-Assisted Continuous Evolution. PACE achieves selection by linking the desired activity of the gene of interest to the production of infectious phage progeny. Expression of the phage's gene III (gIII) is proportionally related to proliferation. Using an accessory plasmid (AP), gIII expression is solely driven by the desired activity of the evolving gene. Each selection phage (SP) encodes the gene to be evolved. Phage encoding active variants of the gene produce infectious progeny, and phage encoding less-active variants fail to produce as many progeny and become outcompeted. Beneficial mutations multiply with successful phage life cycles. An inducible mutagenesis plasmid (MP) increases the mutation rate by decreasing proofreading and increasing error-prone bypass during replication.

During PACE, host cells containing the AP, XP, and MP are continually added to a fixed-volume flask (the 'lagoon') where they encounter phage. After infection, host cells begin expressing the integrase protein from the SP. A successfully evolved integrase, bearing beneficial mutations enhancing its activity on the attP site, aligns the gIII promoter on the AP. Activated gIII expression leads to propagation of the SP that encoded the improved integrase. These SP are again mutated during the next cycle of DNA replication, effectively generating a new library from the fittest variants of the previous library. Fresh host cells are then infected by this new library within the lagoon and the process is repeated. The proliferation of the phage scales with increasing levels of gIII expression over a range of two orders of magnitude. This establishes a competition between mutation library members resulting in the most active variants outcompeting the others.

PACE strategy and Selection Stringency. In addition to the MP for mutagenesis, host cells contained the AP and CP to enable selection for integrases with improved activity. The AP contained the attP site upstream of the C-terminus of a split gIII. The CP contained a promoter aligned with the N-terminus of gIII (the leader sequence) and the attB site. Successful crossover of the att sites on the AP and CP by an active integrase variant forms a single plasmid with a complete gIII. The resulting attL site is encoded and resides in a linker region between the leader sequence and N1 domain to prevent disruption of gene III activity. Stringency was periodically increased during each PACE experiment by decreasing promoter strength, decreasing plasmid copy number, or increasing flow rate.

Phage Preparation and Mutagenesis. The SP backbone was modified by replacing the gene VI promoter with RecA to decrease generation of recombinant wild-type M13 phage. Lagoons were infected with $10^8$ PFU of starter phage. Mutagenesis via MP6 plasmid was induced at concentrations of 100 mM arabinose. Lagoons were sampled every 1-4 hours throughout each PACE experiment.

PACE procedures were as described by Miller et al. ((2020) Nat. Protoc. 15(12):4101-4127) with modifications. In particular, the modified PACE setup included two chemostats that were maintained at volumes ranging from 300-400 mL in 2 L bottles, in which host cell cultures were changed every 2 days to insure arabinose sensitivity.

S2060 cells were transformed with AP, XP, and MP6 plasmids and cultured in Davis Rich Media (DRM) (Harvard Custom Media A and C—US Biological) supplemented with trace metals, 0.1% polysorbate 80, and appropriate antibiotics to maintain plasmids (AP—50 µg/mL Carbenicillin, CP—50 µg/mL Kanamycin, MP—25 µg/mL Chloramphenicol) in addition to 10 µg/mL Tetracycline, 10 µg/mL Fluconazole, and 10 µg/mL Amphotericin B). Host cell colonies were tested for sensitivity to arabinose before expansion to chemostats. A fixed volume 100 mL mixer in a 500 mL bottle was used to mix the two cultures before distribution to 2-6 lagoons which were generally maintained at 40 mL in a 100 mL bottle (except when extremely high flow rates were used to increase stringency) and flow rates ranged from 1-10 V/hr. L-arabinose was supplied to the lagoons at a constant rate of 0.5 µL/min (concentration was dependent on flow rate to maintain 100 mM L-arabinose in the lagoon). In experiments with 6 lagoons, a second chemostat was added along with a mixer prior to distribution to the lagoons which was maintained at 100 mL (Tables 7 and 8).

TABLE 7

| PACE | Time | AP | CP | Flow Rate |
|---|---|---|---|---|
| PhiC31 PACE | 0-72 hr | AP pUC PhiC31 attP | CP RSF1030 PhiC31 attB ProB | 2 V/hr |
| | 72-120 hr | AP pUC PhiC31 attP | CP RSF1030 PhiC31 attB ProA | 2 V/hr |
| | 120-168 hr | AP pUC PhiC31 attP | CP RSF1030 PhiC31 attB Pro3 | 2 V/hr |
| | 168-192 hr | AP pUC PhiC31 attP | CP RSF1030 PhiC31 attB Pro1 | 2 V/hr |
| | 192-212 hr | AP pUC PhiC31 attP | CP RSF1030 PhiC31 attB Pro1 | 3 V/hr |
| Bxb1 PACE 1 | 0-24 hr | AP pUC Bxb1 attP | CP RSF1030 Bxb1 attB ProB | 2 V/hr |

TABLE 7-continued

| PACE | Time | AP | CP | Flow Rate |
|---|---|---|---|---|
| | 24-48 hr | AP pUC Bxb1 attP | CP RSF1030 Bxb1 attB ProA | 2 V/hr |
| | 48-72 hr | AP pUC Bxb1 attP | CP RSF1030 Bxb1 attB Pro3 | 2 V/hr |
| | 72-124 hr | AP pUC Bxb1 attP | CP RSF1030 Bxb1 attB Pro1 | 2 V/hr |
| Bxb1 PACE 2 | 0-24 hr | AP pUC Bxb1 attP | CP RSF1030 Bxb1 attB Pro1 | 3 V/hr |
| | 24-48 hr | AP pUC Bxb1 attP | CP RSF1030 Bxb1 attB Pro1 | 4 V/hr |
| | 48-72 hr | AP pUC Bxb1 attP | CP RSF1030 Bxb1 attB Pro1 | 6 V/hr |
| Bxb1 PACE 3 | 0-24 hr | AP pUC Bxb1 attP | CP RSF1030 Bxb1 attB Pro1 | 2 V/hr |
| | 24-48 hr | AP pUC Bxb1 attP | CP RSF1030 Bxb1 attB Pro1 | 4 V/hr |
| | 48-72 hr | AP pUC Bxb1 attP | CP RSF1030 Bxb1 attB Pro1 | 6 V/hr |
| | 72-96 hr | AP pUC Bxb1 attP | CP RSF1030 Bxb1 attB Pro1 | 8 V/hr |
| | 96-98 hr | AP pUC Bxb1 attP | CP RSF1030 Bxb1 attB Pro1 | 10 V/hr |
| Bxb1 PACE 4 | 0-48 hr | AP R6k Bxb1 attP | CP RSF1030 Bxb1 attB Pro1 | 2 V/hr |
| | 48-72 hr | AP R6k Bxb1 attP | CP RSF1030 Bxb1 attB Pro1 | 3 V/hr |
| | 72-96 hr | AP R6k Bxb1 attP | CP RSF1030 Bxb1 attB Pro1 | 4 V/hr |

TABLE 8

| PACE | | Starting Material |
|---|---|---|
| PhiC31 PACE | Lagoon 1 | SP RecA PhiC31 Int605 (wild-type) |
| | Lagoon 2 | SP RecA PhiC31 P2 |
| | Lagoon 3 | SP RecA PhiC31 P1 |
| | Lagoon 4 | SP RecA PhiC31 P1 |
| | Lagoon 5 | SP RecA PhiC31 P3 |
| | Lagoon 6 | SP RecA PhiC31 P3 |
| Bxb1 PACE 1 | Lagoon 1 | SP RecA Bxb1 (wild-type) |
| | Lagoon 2 | SP RecA Bxb1 (wild-type) |
| | Lagoon 3 | SP RecA Bxb1 (wild-type) |
| | Lagoon 4 | SP RecA Bxb1 (wild-type) |
| | Lagoon 5 | SP RecA Bxb1 (wild-type) |
| | Lagoon 6 | SP RecA Bxb1 (wild-type) |
| Bxb1 PACE 2 | Lagoon 1 | SP RecA Bxb1 PACE1 L4-100 hr |
| | Lagoon 2 | SP RecA Bxb1 PACE1 L6-100 hr |
| Bxb1 PACE 3 | Lagoon 1 | SP RecA Bxb1 L2-9 |
| | Lagoon 2 | SP RecA Bxb1 PACE2 pool |
| Bxb1 PACE 4 | Lagoon 1 | SP RecA Bxb1 (wild-type) |
| | Lagoon 2 | SP RecA Bxb1-c2 |
| | Lagoon 3 | SP RecA Bxb1-c3 |
| | Lagoon 4 | SP RecA Bxb1-c9 |
| | Lagoon 5 | SP RecA Bxb1-c22 |
| | Lagoon 6 | SP RecA Bxb1 L7-3 |

Phage Enrichment Assay. E. coli cultures containing both AP and CP (2 mL, $OD_{600}$=0.3-0.6) were inoculated with $10^5$ PFU/mL of purified M13 phage and incubated at 37° C. at 180 rpm for 18 hours. Cultures were centrifuged at 12,000×g for 2 minutes and supernatants were collected. Phage counts were obtained by activity-independent plaque assay in S2208 cells (Badran et al. (2016) Nature 533:58-63).

Flipper Flow Cytometry Assay. Helper plasmids encoding integrase variants (100 ng) and a flipper plasmid containing ZsGreen flanked by attB and attP sites (500 ng; Table 9) were transfected into 24-well plates seeded with HEK293T cells as described above. Following 3 days of culture, cells were resuspended using cold Live Cell Imaging Solution (Thermo Fisher Scientific) and fluorescein-5-isothiocyanate (FITC) emission was assessed by flow cytometry (excitation 488 nm, emission 530 nm (BL1)) of >20.000 live, single cells per condition using an Attune NXT flow cytometer (Thermo Fisher Scientific),

TABLE 9

| Phage Integrase | Minimal att | Sequence | SEQ ID NO: |
|---|---|---|---|
| PhiC31[1] | attB | gtgccagggcgtgcccttgggctccccgggcgcgt | 15 |
| | attP | tgccccaactggggtaacctttgagttctctcagttgggggc | 16 |
| Bxb1[2] | attB | ggcttgtcgacgacggcggtctccgtcgtcaggatcat | 13 |
| | attP | ggtttgtctggtcaaccaccgcggtctcagtggtgtacggta caaacc | 14 |
| PaO1[3] | attB | ccgtgacctacatgctcgaagggcgtatgcgcc | 230 |
| | attP | gtaacgctcttcgagaaagcagattctcatatccatcttgagt cttctttctcgcaagacaacacgaaatagacacagtctcttc cctagctgtacactgagcc | 231 |

[1]Groth et al. (2009) Proc. Natl. Acad. Sci. USA 97:5995-6000;
[2]Ghosh et al. (2003) Mol. Cell 12(5):1101-11;
[3]Durrant et al. (2023) Nat. Biotechnol. 41:488-499, Phage Preparation and Mutagenesis. The SP backbone was modified by replacing the gene VI promoter with RecA to decrease generation of recombinant wild-type phage. Lagoons were infected with $10^8$ PFU of starter phage. Mutagenesis via MP6 plasmid was induced at concentrations of 100 mM arabinose. Lagoons were sampled every 1-4 hours throughout each PACE experiment.

Rationale for Normalization Using the Product/Reference Ratio (PRR). Two options exist for the location of the target probe: (1) The probe can be placed in the donor, with the forward primer in the donor and the reverse primer in the genome, or (2) The probe can be placed in the genome, with the forward primer in the donor and the reverse primer in the genome. An issue with the donor-located probe is that insertion at an off-target sequence positions the probe and reverse primer downstream of an unknown genomic sequence. Mispriming from the genome could generate a false signal. A second issue is that a donor-located probe cannot be used to determine the ratio of potential target sequences to reference sequences. If a greater number of target sequences exist than reference sequences, then a greater number of opportunities exist for targeting, and the final targeting efficiency will be over-reported. Accounting for this issue is especially important when assaying cell lines with abnormal numbers of chromosomes and where the reference sequence often is located on a different chromosome than the target sequence. To prevent ddPCR over- or under-reporting, the ratio of target product to reference signal was defined as the product/reference ratio (PRR). Targeting efficiencies for unknown samples were divided by the PRR to normalize for differences in available targets and references. To determine the PRR, untransfected cell lines were assayed using FAM probes designed to bind the genomic target sequence. The reverse primer is located in the genome and a second PRR optimization primer is also located in the genome and flanks the probe. The ddPCR is run with standard HEX probes designed to bind the genomic reference sequence that are flanked by genomic primers. PRR values for target sequences used herein are provided in Table 10. Templates were lysates isolated from wells of untransfected cells from the indicated cell lines (n=3). HEK293 clones were first edited by prime editing for insertion of the indicated att site. Probes were designed to bind the genomic target sequence. Primers for the HEK293 clones included the forward primer in the att site and the reverse primer in the genome. Primers for the remaining cell lines included the forward primer and reverse primer in the genome.

TABLE 10

| ref | cell line | target | ave PRR | stdev |
|---|---|---|---|---|
| RPP30 | HEK293 | ROSA 1a | 0.72 | 0.034 |
| | HEK293 | ROSA 3a | 0.76 | 0.037 |
| | HEK293 | Xq22 1a | 1.01 | 0.087 |
| | HEK293 | AAV 3a | 0.47 | 0.007 |
| | HEK293 | AAV 2a | 0.43 | 0.007 |
| | HEK293 | AAV 1a | 0.42 | 0.017 |
| UBE2D2 | HEK293 | ROSA 3a | 1.01 | 0.006 |
| | HEK293 | AAV 3a | 0.63 | 0.017 |
| | HEK293T | ROSA 3a | 1.22 | 0.011 |
| | HeLa | ROSA 3a | 0.92 | 0.008 |
| | K562 | ROSA 3a | 1.24 | 0.004 |
| | HEK293 clone | PhiC31 attP41 ROSA 3a | 0.67 | 0.004 |
| | HEK293 clone | PhiC31 attP41 AAV 3a | 0.65 | 0.004 |
| | HEK293 clone | Bxb1 attB38 ROSA 3a | 0.38 | 0.011 |

Off Target Analysis. Genomic PCR primers (Table 11) were generated to previously predicted Bxb1 pseudo sites (Anzalone et al. (2022) *Nat. Biotechnol.* 40:731-740; Yarnall et al. (2023) *Nat. Biotechnol.* 41:500-512). For each site, two primer sets were designed. The first (control) set was made to amplify the genome to verify ample template was used. The second set was made to amplify the junction of the genome and donor. Additional primers were generated to amplify successful insertion at ROSA26. Lysates from HEK293T transfections performed on two separate days were used as template for genomic PCR using the Q5 polymerase (NEB) and visualized on a 2% agarose gel.

TABLE 11

| Primer | Sequence | SEQ ID NO: |
|---|---|---|
| Rosa OnT Rev | ttctagagacagacataaagcatgatca | 232 |
| DL OT1 fwd | GGAAATAAGTTATCACAATGGGAAAT | 233 |
| DL OT1 rev | TCGCGATTCTTAAAAGGAGAGG | 234 |
| DL OT2 fwd | CCATTCATATTTTGAAACAAAAGG | 235 |
| DL OT2 rev | GCATTGCACTCCTACATACAACA | 236 |
| DL OT3 fwd | GCTGTGGTTATTCCCAGCTC | 237 |
| DL OT3 rev | CTGGGAACACTGGACAAAATCC | 238 |
| DL OT4 fwd | GGAAAGCTTTGACAAGTGGAA | 239 |
| DL OT4 rev | GCCTACTTGCCCTTCTTCCT | 240 |
| PASTE ch2 off For | AGGGACCTTTGCCTGTGTGAGTC | 241 |
| PASTE ch2 off Rev | cactcacacagacagaggcc | 242 |
| PASTE ch3 off For | CCAGGTGAGAGTCAGGGTAGTGTTCA | 243 |
| PASTE ch3 off Rev | gcttgcgcggcctacgt | 244 |
| PASTE ch9 off For | TCAGCTCTGTGCTGAGGCGAA | 245 |
| PASTE ch9 off Rev | GCACAACCCTGGCTGTCC | 246 |
| ddPCR pCMV Rev2 | tgaatgcaattgttgttgttaacttgt | 247 |

Factor VIII and Von Willebrand Factor. To measure expression and export of recombinant proteins, HEK293T cells were transfected with 300 ng of PE5max, 30 ng of each epegRNA plasmid, 120 ng of helper (integrase), 120 ng of donor, and 40 ng of DsRed expression plasmid (for sorting). Media was collected three days post transfection and Factor VIII protein expression was assayed using the Human Coagulation Factor VIII Total Antigen ELISA kit (Innovative Research) and Factor VIII protein activity was assayed using the Chromogenix Coamatic® Factor VIII kit (DiaPharma). Von Willebrand Factor was detected using the VWF Human ELISA Kit (Invitrogen).

Example 2: Directed Evolution of Serine Integrases Improves Site Specific Insertion of Transgenes Using Prime Editing Previously, directed evolution was used to improve PhiC31 integrase activity on its native att sites (Keravala et al. (2009) *Mol. Ther.* 17(1):112-20). It was posited that PhiC31 and its improved variants could increase targeted integrase insertion efficiency. Initially, previously characterized safe harbor loci were selected that were distant from cancer-related genes and shown to permit expression of inserted genes. These included AAVS1 (Oceguera-Yanez et al. (2016) *Methods* 101:43-55), Xq22.1 (Chalberg et al. (2006) *J. Mol. Biol.* 357(1):28-48), and ROSA26 (Irion et al. (2007) *Nat. Biotechnol.* 25:1477-1482). PE uses a fusion protein consisting of a Cas9 nickase and reverse transcriptase called PE5, as well as a prime editing guide RNA (pegRNA). The pegRNA is a modified version of a single guide RNA (sgRNA) that both directs PE5 to the target genomic sequence and encodes the desired edit. The pegRNA contains a 5' spacer sequence that directs PE5 to nick the target sequence. The primer binding site (PBS)

found on the 3' end of the pegRNA anneals to the non-target DNA strand following the nick in the target strand. The pegRNA contains a reverse transcriptase template (RTT) that is reverse transcribed to generate a 3' single-strand flap of DNA that encodes the inserted DNA, such as the att site. During twin PE, a second pegRNA directs the insertion of an adjacent flap that includes overlapping homologous sequence so that the two flaps form a double-stranded intermediate. Upon resolution of the intermediate, the new sequence becomes permanently inserted.

Because prime editing efficiency is generally higher for shorter inserts, pegRNA were designed for inserting the minimal PhiC31 attB site (35 bp) or attP site (41 bp). To maximize efficiency, an epegRNA containing a structured RNA motif was used to prevent degradation (Nelson et al. (2022) Nat. Biotechnol. 40(3):402-410). In addition, an optimized cr772 scaffold (Jost et al. (2020) Nat. Biotechnol. 38(3):355-364) and PE5max which includes a dominant negative mutant of human mutL homolog 1 (MLH1) involved in DNA mismatch repair with an optimized editor architecture were used (Chen et al. (2021) Cell 184(22): 5635-5652.e29)(Tables 15-16). PE5max and two twin epegRNA expression plasmids for each target site were transfected into HEK293 cells. Droplet digital PCR (ddPCR) is a form of quantitative PCR that reports highly accurate copy number of genomic inserts over a wide range of template concentrations.

Prime editing insertion of att sites ranged from 0.3% to 62.1% as measured by amplicon sequencing using genomic primers flanking the insert (FIG. 1) and confirmed by ddPCR. Clonal HEK293 cell lines were generated, which included the most efficient and accurate epegRNA pairs targeted to AAVS1 and ROSA26, which were used to compare integration efficiency of PhiC31 integrase variants. Wild-type PhiC31 integrase was compared to three hyperactive variants called P1, P2, and P3 (Keravala et al. (2009) Mol. Ther. 17(1):112-20). Two of these three variants (P1 and P3) demonstrated increased activity measured by ddPCR relative to the wild-type integrase at both loci with integration efficiencies for P3 reaching 11.1% and 3.0% at ROSA26 and AAVS1, respectively (FIG. 1). In place of using a cell line containing a pre-inserted att site, PE and integrase expression plasmids were combined in a single transfection. This strategy allowed for the insertion of an att site using PE followed by the insertion of the donor plasmid by PhiC31 integrase at the target sequence. PE5max and epegRNA plasmids were co-transfected to insert the 41 bp PhiC31 attP site at ROSA26 along with a 6.6 kb donor containing the attB site and a helper expressing PhiC31 integrase. Notably, PhiC31 insertion of the donor plasmid was detected for all four integrase variants with a favorable efficiency of 1.9% for P3 compared to 0.54% for wild-type. This demonstrated that hyperactive variants outperform wild-type PhiC31 integrase during PE-mediated gene insertion. Based upon these results, it was reasoned that directed evolution of PhiC31 variants may further increase the efficiency of gene insertion.

The prior directed evolution campaigns that generated P1, P2, and P3 required laborious steps of mutagenesis, gene expression, screening, and replication. Alternatively, PACE rapidly and iteratively selects, replicates, and mutates genes at rates of >70 generations per day without human intervention (Esvelt et al. (2011) Nature 472:499-503). PACE achieves selection by linking the desired activity of the gene of interest to the production of infectious phage progeny.

Expression of M13 phage's gene III (gIII) is proportionally related to proliferation. Using an accessory plasmid (AP), gIII expression is solely driven by the desired activity of the evolving gene. Each selection phage (SP) encodes the gene to be evolved. Phage encoding active variants of the gene produce infectious progeny, and phage encoding less-active variants fail to produce as many progeny and become outcompeted. Beneficial mutations multiply with successful phage life cycles. An inducible mutagenesis plasmid (MP) increases the mutation rate by decreasing proofreading and increasing error-prone bypass during replication. During PACE, host cells containing the AP, CP, and MP are continually added to a fixed-volume flask (called the 'lagoon') where they encounter phage. After infection, host cells begin expressing the integrase protein from the SP. A successfully evolved integrase, bearing beneficial mutations enhancing its activity on the attP site, aligns the gIII promoter on the AP. Activated gIII expression leads to propagation of the SP that encoded the improved integrase. These SP are again mutated during the next cycle of DNA replication, effectively generating a new library from the fittest variants of the previous library. Fresh host cells are then infected by this new library within the lagoon and the process is repeated. The proliferation of the phage scales with increasing levels of gIII expression over a range of two orders of magnitude. This establishes a competition between mutation library members resulting in the most active variants outcompeting the others.

To adapt PACE to improve integrase activity, the integrase was encoded on a selection phage (SP) and pIII expression was linked to a successful crossover event between the attB and attP sites. A promoter and the amino-terminus of gene III (gIII encodes pIII), called the leader sequence, followed by the attP site were placed on a on a complementary plasmid (CP). An accessory plasmid (AP) contained the attB site and the remaining portion of gIII (N1-C domains). During a crossover event between the attB and attP, the promoter and leader sequence become aligned with gIII that subsequently leads to expression. The resulting attL site is encoded within a flexible loop so as not to disrupt the function of pIII. Successful events require precise and directional recombination of the attL site.

PACE experiments were initiated with SP encoding PhiC31, P1, P2, and P3 and run for 212 hours (222 cycles of evolution) as stringency was increased incrementally by decreasing gIII promoter strength and increasing the flow rate. Different host cells containing CP with four gIII promoters were sequentially added to the lagoon. In order from strongest to weakest, promoters ProB, ProA, Pro3, and Pro1 were used to challenge the evolving integrases. Because each recombination event produces low levels of pIII when using a weak gIII promoter, only highly active integrase variants capable of recombining more plasmids than less active variants can generate enough pIII to make sufficient infectious progeny to maintain in the system. Less active integrase variants fail to perform enough recombination events to produce sufficient numbers of progeny and are drained from the system. To further challenge the evolving integrases, the flow rate was increased from 2 to 3 lagoon volumes per hour, thereby reducing the time the integrase variants had to generate progeny. The presence of the phage in each lagoon was monitored by collecting the media outflow and performing the activity-independent plaque assay. Dilutions of media containing phage were plated on the S2208 E. coli strain that produces blue plaques that were counted to calculate phage concentration. For each of the four host cell transfers, outflow media was collected at 0, 1, 2, and 4 hour time points and every 4 hours afterwards. The expected pattern of an initial drop in titer was observed as many of the early phage were drained. This was followed by a gradual increase in titer, presumably due to the integrase variants accumulating beneficial mutations. Next, phage numbers plateaued, likely due to the integrase variants reaching a point of hyperactivity that they were no longer challenged by the current level of stringency, necessitating increases in stringency for continued productive evolution. Isolated phage were selected at time points throughout the IntePACE experiment and recombination activity was separately measured using the overnight phage enrichment assay. Cells containing the AP and CP using the ProA promoter to drive gIII were inoculated with $10^5$ PFU/ml of purified phage isolated from IntePACE. The cells were cultured in the presence of the phage overnight and the next day the phage concentration was measured using the activity-independent plaque assay, similar to above. Time points containing phage encoding hyperactive integrase variants were expected to recombine more AP and CP and generate more phage progeny than phage encoding unevolved integrase. This method allows for individual time points to be directly compared. Evolved libraries increased efficiency by 15.4-, 70.2-, and 16.4-fold over P1, P2, and P3, respectively, as measured by overnight phage enrichment assay. To test activity in human cells, evolved integrase variants were isolated from single plaques and cloned into expression plasmids. A plasmid-based 'flipper' assay was designed in which a crossover event between the attP and attB sites flips the orientation of ZsGreen to align with the H1 promoter and activate expression. In agreement with results from *E. coli*, increased numbers of ZsGreen expressing cells were observed for evolved integrases, with the greatest improvement by P2 from 9.9% to 44.9%.

Figure 2:
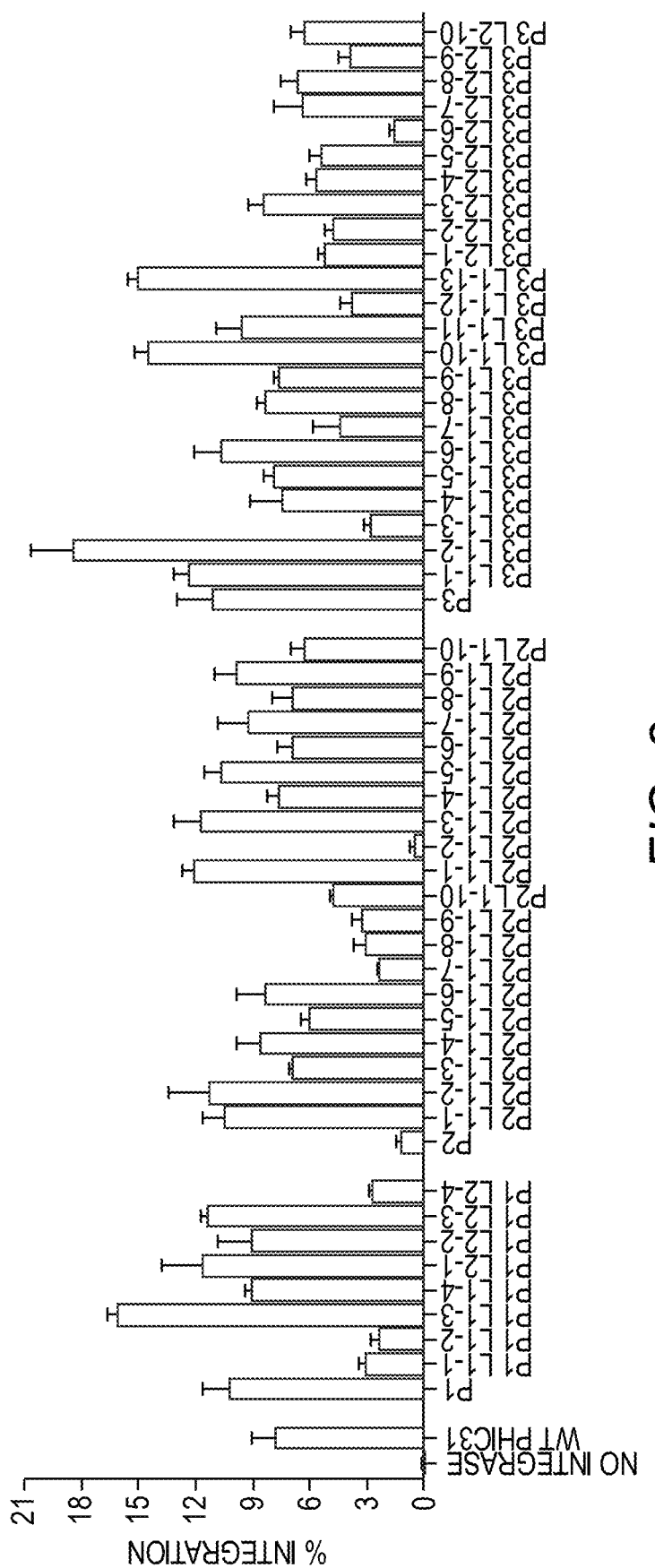
FIG. 2. Evolved integrase helper plasmids were co-transfected into the clonal HEK293 cell line containing a pre-installed attP landing pad with a 6.6 kb donor plasmid. Unevolved controls are shown for comparison. On-target integrations were measured with droplet digital PCR. n=3.
Figure 3:
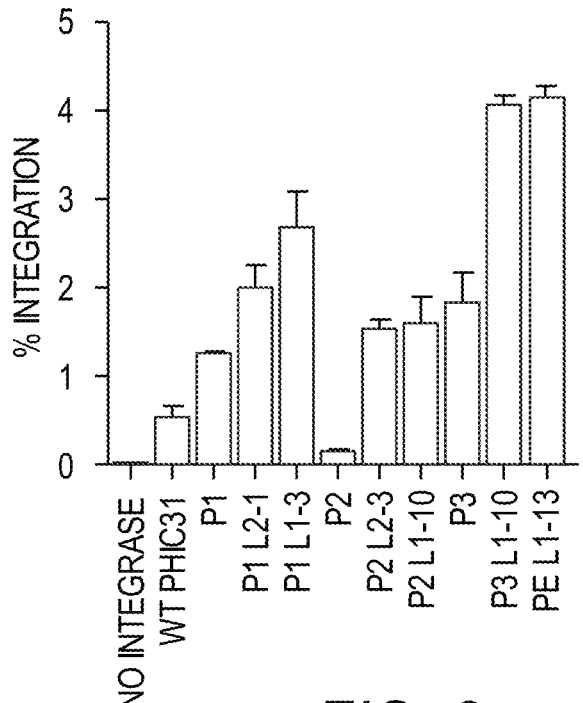
FIG. 3. Integration by PACE evolved PhiC31 mutants with twin prime editing at ROSA in HEK293 cells measured by droplet digital PCR. Unevolved controls are also shown. n=3.

Evolved variants (Table 12) were compared in clonal HEK293 cell lines with a pre-inserted PhiC31 attP site at the AAVS1 or ROSA26 locus. Notably, gene insertion by evolved integrases outcompeted their starting variants. The greatest improvement was between P2 (1.3%) and a 36-hour evolved variant P2-L2-3 (11.8%). The highest integration rates came from a P3 variant (L1-2) that integrated 18.4% at the ROSA26 site (FIG. 2). Similarly, evolved integrases co-transfected with prime editing components for attP insertion resulted in higher gene targeting efficiencies. Specifically, a 36-hour variant evolved from P2 (L1-10) increased by 10.5-fold and a 184-hour variant from P3 (L1-13) reached 4.2% efficiency at the ROSA26 target sequence (up from 1.9% from the P3 starting variant) (FIG. 3).

TABLE 12

| Mutant | N-terminal Addition[1] | Internal Mutations[2] |
|---|---|---|
| Wild-Type PhiC31 | — | — |
| P1 | MIQGVVSG (SEQ ID NO: 3) | M1E, D2V, V41I |
| P2 | | D32A, D36A, D44A |
| P3 | MTMITPSAQLTLTK GNKSWSSLVTAAS VLEFATMIQGVAG (SEQ ID NO: 5) | M1V, D2V, D32A, D36A, V41I, D44A |
| P1 L1-1 | MIQEVVSG (SEQ ID NO: 4) | M1V, D2V, V41I, R49R, M278L, L319L, F527F |
| P1 L1-2 | MIQGVVSG (SEQ ID NO: 3) | M1V, D2V, V41I, L229L, G344V |
| P1 L1-3 | MIQGVVSG (SEQ ID NO: 3) | M1V, D2V, V41I, E431V |
| P1 L2-1 | MIQGVVSG (SEQ ID NO: 3) | M1V, D2V, V41I, R43R, P230S, Q355Q, K520K |
| P1 L2-2 | MIQGVVSG (SEQ ID NO: 3) | M1V, D2V, V41I, V117V, H228Y, A255G, A580V, D594D |
| P1 L2-3 | MIQGVVSG (SEQ ID NO: 3) | M1V, D2V, V41I, G505V, P587P, D594N |
| P2 L1-1 | | D32A, A199T, P535P |
| P2 L1-2 | | D252G |
| P2 L1-3 | | D32A, D36A, D44A, S396N, R551R |
| P2 L1-4 | | D32A, D36A, D44A, N406S, E512K |
| P2 L1-5 | | D32A, D36A, D44A, K197K, D254D, G344D, A397T, R457R, A616V |
| P2 L1-6 | | D32A, D36A, D44A, S55S, E77E, I153I, G344D, S359S, V552V, A585A |
| P2 L1-7 | | D32A, D36A, D44A, K266K, D362G |
| P2 L1-8 | | D32A, D36A, D44A, F231L, G505S, D592G |

TABLE 12-continued

| Mutant | N-terminal Addition[1] | Internal Mutations[2] |
|---|---|---|
| P2 L1-9 | | D32A, D36A, D44A, I103I, T302A, D362G, G399G, E449D, E472D |
| P2 L1-10 | | D32A, D36A, D44A, E77E, I153I, H200H, P274S, G344D, K382K, T536A |
| P2 L2-1 | | A498A |
| P2 L2-2 | | D32A, D36A, D44A, R320R, A333T, G429S, A516T, A604S |
| P2 L2-3 | | D32A, D36A, D44A, A238A, R457R, P535L |
| P2 L2-4 | | E14G, D32A, D36A, D44A, E176D, A238A, S396R, R478R, F553F, K586Q |
| P2 L2-5 | | D32A, D36A, D44A, E176D, L229L, A238A, A333D, S359S |
| P2 L2-6 | | D32A, D36A, D44A, I74I, R96R, E176D, A238A, A333D, E378K, D590G |
| P3 L1-1 | MTMITPSAQLTLTKGNKSWSSLVTAASVLEFATMIQGVAG (SEQ ID NO: 5) | M1E, D2V, D32A, D36A, V41I, D44A |
| P3 L1-2 | MTMITPSAQLTLTKGNKSWSSLVTAASVLEFATMIQGVAG (SEQ ID NO: 5) | M1E, D2V, D32A, D36A, V41I, D44A, S235S, L364M |
| P3 L1-3 | MTMITPSAQLTLTKGNKSWSSLVTAASVLEFATMIQGVAG (SEQ ID NO: 5) | M1E, D2V, D32A, D36A, V41I, D44A, G346S, G505G |
| P3 L1-4 | MTMIYPFPAQLTLTKGNKSWSSLVTAASVLEFATMIQGVAG (SEQ ID NO: 6) | M1E, D2V, D32A, D36A, V41I, D44A, R345R, D362N, L468L, V603I |
| P3 L1-5 | MTMITPSAQLTLTKGNKSWSSLVTAASVLEFATMIQGVAG (SEQ ID NO: 5) | M1E, D2V, D32A, D36A, V41I, D44A, D362N, V612V |
| P3 L1-6 | MTMITPSAQLTLTKGNKSWSSLVTAASVLEFATMIQGVAG (SEQ ID NO: 5) | M1E, D2V, A24A, D36A, V41I, D44A, N196N, W448R, P609S |
| P3 L1-7 | MTMITPSAQLTLTKSNKSWNSLVTAASVLEFATMIQGVAG (SEQ ID NO: 7) | M1E, D2V, D32A, D36A, V41I, D44A, D362G, V563V, T600T |
| P3 L1-8 | MTMITPSAQLTLTKGNKSWSSLVTAASVLEFATMIQGVAG (SEQ ID NO: 8) | M1E, D2V, D32A, D36A, V41I, D44A, F231L, A410T, V603V |
| P3 L1-9 | MTMITPSAQLTLTKGNKSWSSLVTAASVLEFATMIQGVAG (SEQ ID NO: 5) | M1E, D2V, D32A, D36A, V41I, D44A, T262T, D362N, V393V, L436L |
| P3 L1-10 | MTMITPSAQLTLTKSNKSWSSLVTAASVLEFATMIQGVTG (SEQ ID NO: 9) | M1E, D2M, D32A, V41I, D44A, G45G, G264G, E331E, L351V, G445G, V563V, A580V, V603V |
| P3 L1-11 | MTMITPSAQLTLTKGNKSWSSLVTAASVLEFATMIQGVAG (SEQ ID NO: 5) | M1E, D2V, A24A, D32A, D36A, V41I, D44A, W438R, P609S |

TABLE 12-continued

| Mutant | N-terminal Addition[1] | Internal Mutations[2] |
|---|---|---|
| P3 L1-12 | MTMITPSAQLTLTK GNKSWSSLVTAAS VLEFATMIQGVAG (SEQ ID NO: 5) | M1E, D2V, A24A, D32A, D36A, V41I, D44A, H240R, A333S, A340V, W448R, T600S, P609S |
| P3-L2-1 | MTMITPSAQLTLTK GNKSWSSLVTAAS VLEFATMIQGVAG (SEQ ID NO: 5) | M1E, D2V, D32A, D36A, V41I, D44A, R347K, I424I |
| P3-L2-2 | MTMITPSAQLTLTK DNKSWSSLVTAAS VLEFATMIQGVAG (SEQ ID NO: 10) | M1E, D2V, D32A, D36A, V41I, D44A, V322V, L351Q, D549D |
| P3-L2-3 | MTMITPSAQLTLTK GNKSWSSLVTAAS VLEFATMIQGVAG (SEQ ID NO: 5) | M1E, D2V, D32A, D36A, V41I, D44A, S107S, D362N |
| P3-L2-4 | MTMITPSAQLTLTK SNKSWSSLVTAAS VLEFATMIQGVAG (SEQ ID NO: 11) | M1E, D2V, S12N, D32A, D36A, V41I, D44A, P58P, I103I, E153V, E514E, A580V, V603A |
| P3-L2-5 | MTMITPSAQLTLTK GNKSWSSLVTAAS VLEFATMIQGVAG (SEQ ID NO: 5) | M1E, D2V, D32A, D36A, V41I, D44A, R353R, D362N, L499L, T568T |
| P3-L2-6 | MTMITPSAQLTLTK SNKSWSSLVTAAS VLEFATMIQGVAG (SEQ ID NO: 11) | M1E, D2V, S18N, D32A, D36A, V41I, D44A, V51M, I103I, I153V, A450D, V603A |
| P3-L2-7 | MTMITPSAQLTLTK SNKSWSSLVTAAS VLEFATMIQGVAG (SEQ ID NO: 11) | M1E, D2V, D32A, D36A, V41I, D44A, I103I, I153V, S269N, A450D, E517E, V603A |
| P3-L2-8 | MTMITPSAQLTLTK SNKSWSSLVTAAS VLEFATMIQGVAG (SEQ ID NO: 11) | M1E, D2V, D32A, D36A, V41I, D44A, I103I, I153V, G260G, L436L, A450D, L501L, V603A |
| P3-L2-9 | MTMITPSAQLTLTK SNKSWSSLVTAAS VLEFATMIQGVAG (SEQ ID NO: 12) | M1E, D2V, D32A, D36A, V41I, D44A, I103I, I153V, A450D, E452K, V603A |

[1]Keravala et al. (2009) Mol. Ther. 17(1):112-120.
[2]Amino acid positions are with reference to the wild-type 605 amino acid PhiC31 protein (SEQ ID NO: 2).

Figure 4:
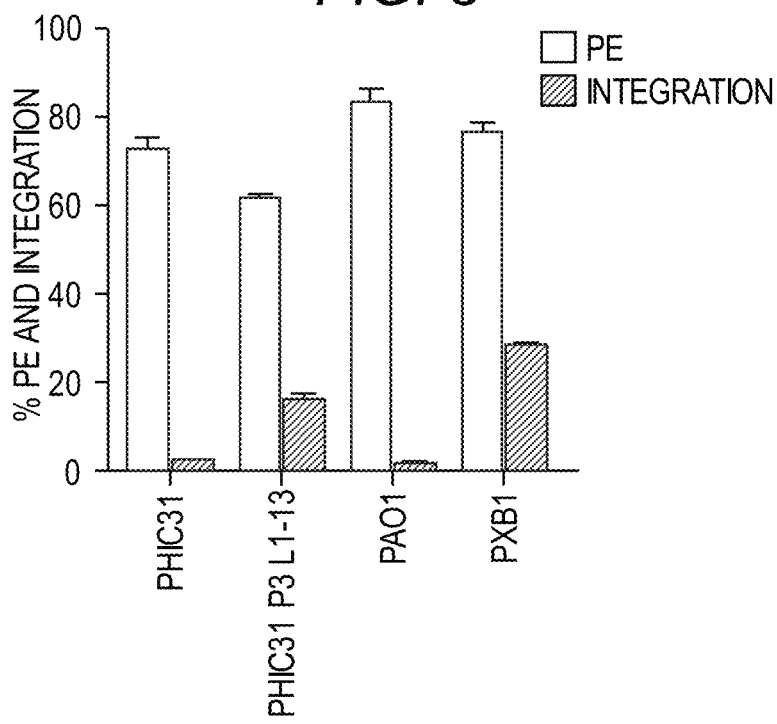
FIG. 4. Comparison of twin prime editing and integration frequencies of 6.6 kb donor with PhiC31, evolved PhiC31, Pa01, and Bxb1 integrases in HEK293T cells measured by droplet digital PCR. n=3.

Using the optimized prime editing parameters for inserting att sites, evolved PhiC31 integration rates were compared with previously described integrases Bxb1 (Anzalone et al. (2022) Nat. Biotechnol. 40:731-740) and Pa01 (Durrant et al. (2023) Nat. Biotechnol. 41:488-499). Surprisingly, wild-type Bxb1 had greater efficiencies compared to evolved PhiC31 mutants (FIG. 4). It was reasoned that Bxb1 might serve as a superior starting point for evolution. Encouraged by the results with PhiC31, the same PACE strategy was adapted to increase Bxb1 integrase activity on its native att sites. The full Bxb1 attP site and minimal attB site (Ghosh et al. (2003) Mol. Cell 12(5):1101-11; Anzalone et al. (2022) Nat. Biotechnol. 40:731-740) were substituted for the PhiC31 att sites in the AP and CP, respectively (Tables 7 and 8). In total, phage were evolved for 9 days (approximately 276 cycles of mutagenesis) (Esvelt et al. (2011) Nature 472:499-503).

Figure 5A:
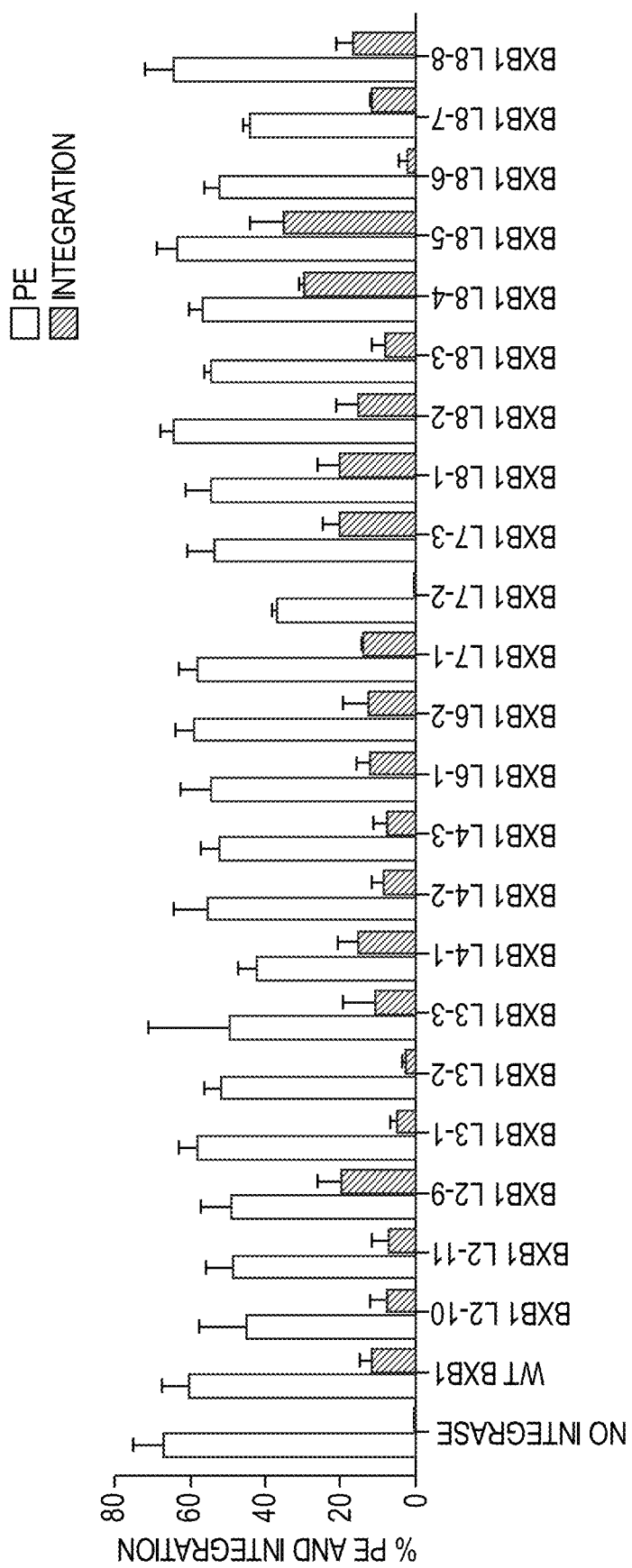
FIGS. 5A and 5B. Twin prime editing and integration frequency in HEK293 cells of PACE evolved Bxb1 mutants measured by droplet digital PCR. n≥4 on multiple days.
Figure 5B:
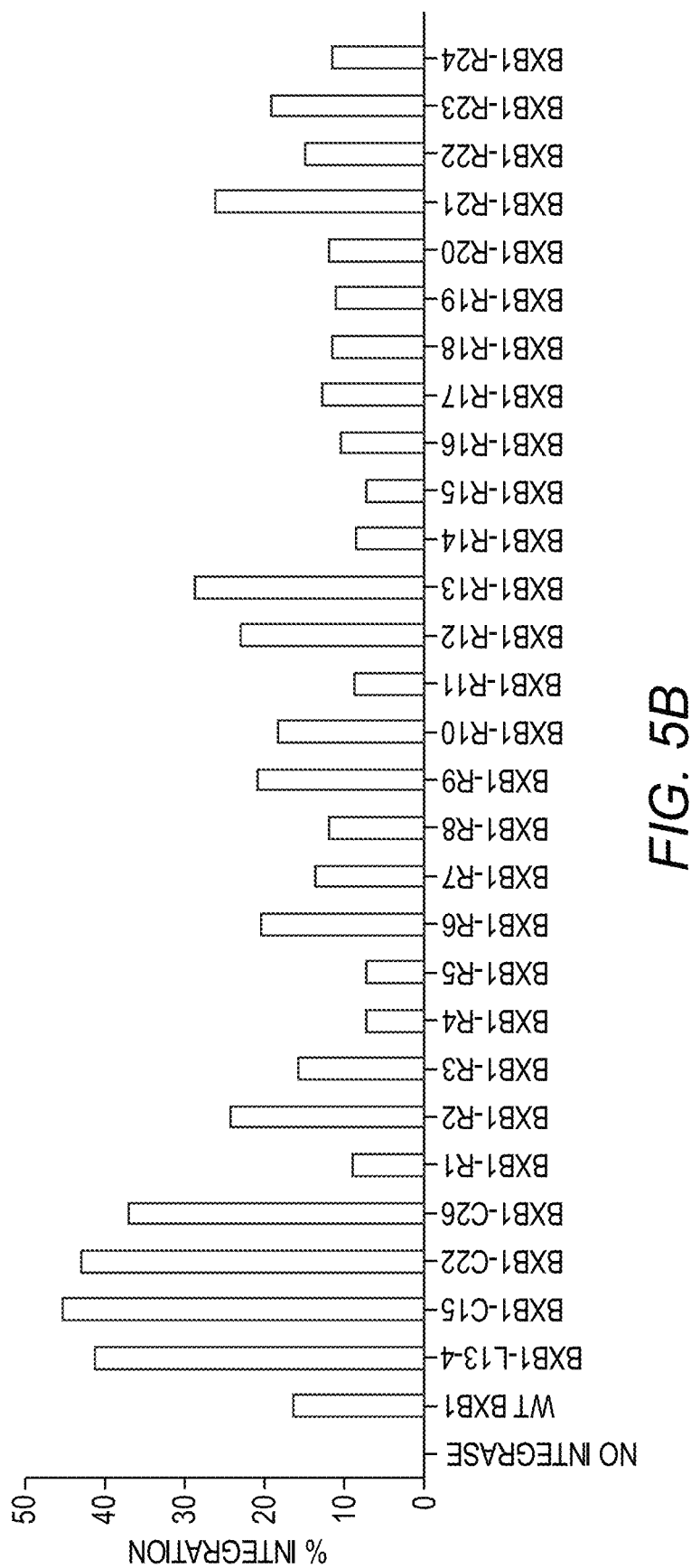

Similar to PACE with PhiC31, enrichment assays demonstrated that evolved variants of Bxb1 vastly improved in the bacterial system. New variants (Table 13) were cloned into mammalian expression plasmids which were then co-transfected with a donor into a clonal HEK293 cell line containing a pre-inserted Bxb1 attB site at ROSA26. It was observed that efficiencies up to 21% with the highest activity variant (Bxb1-L8-5) were 2.5-fold over wild-type Bxb1 integrase. Simultaneous prime editing and evolved Bxb1 integrase-mediated gene insertion resulted in efficiencies ranging from 2.1%-35.4%, up to a 3.1-fold increase in efficiency over wild-type Bxb1 (FIG. 5A and FIG. 5B). Additional rounds of evolution did not result in variants with increased efficiency.

TABLE 13

| Bxb1 Mutant | Mutations |
|---|---|
| Wild-Type Bxb1 | — |
| Bxb1-L4-1 | H111P, E434G |
| Bxb1-L6-1 | T285A |
| Bxb1-L6-2 | G156G, A369P |
| Bxb1-L4-2 | R63K, R88R, A110A, P295P |
| Bxb1-L4-3 | D36A, R63K, P292P, L479I |
| Bxb1-L2-9 | H95Y |
| Bxb1-L2-10 | V5V, S106S, E434G |
| Bxb1-L2-11 | D51D, H189N |
| Bxb1-L3-1 | L164L, H203Y, Q480STOP |
| Bxb1-L3-2 | F67S, V187I, A261T |
| Bxb1-L3-3 | L4I |
| Bxb1-L7-3 | I87L, V187V, A218A, E419E, A425T, E483E |
| Bxb1-L8-1 | R63K, A119S, P295P, E361E, M499T |
| Bxb1-L8-2 | R63K, V122M, P295P |
| Bxb1-L8-3 | R63K, A347E |
| Bxb1-L8-4 | V40I, R63K, V122M, P295P, R319K, S428S |
| Bxb1-L8-5 | R63K, V122M, P295P, R487R |
| Bxb1-L8-7 | L278L, P295P, P332H, A369T, V380I |
| Bxb1-L8-8 | E42K, R63K, D99N, E133E, A145T, K153S, P295P, A369E, R494S |
| Bxb1-L9-1 | V40A, R63K, H89G, Q191Q, P295P, L302L, C307C |
| Bxb1-L9-2 | V40V, R63K, P295P, R362K, G370G, G468G |
| Bxb1-L9-3 | G209G, A288V, A311V, A398S, R416K, T453I, H496N, E42K, G209G |
| Bxb1-L9-4 | A288V, A311V, A398S, R416K, T453I, H496N |
| Bxb1-L9-5 | S18S, R63K, E69E, I87V, P295P, P332H, H334R, A369E |
| Bxb1-L9-6 | S18S, E42K, R63K, E69E, E133E, P295P, P332H, H334R |
| Bxb1-L9-7 | P268P, A288V, A311V, D359D, T388M, T453I, V466V, H496N |
| Bxb1-L9-8 | A288V, A311V, R319G, A398S, R416K, T453I, H496N, E434G |
| Bxb1-L9-9 | E42K, A288V, A311V, A398S, R416K, T453I, H496N, E434G |
| Bxb1-L10-1 | H95Y, R287R, K313R |
| Bxb1-L10-2 | H95Y, A280T |
| Bxb1-L10-3 | H95Y, V264A |
| Bxb1-L10-4 | H95Y, T254S |
| Bxb1-L10-5 | V46V, H95Y, V179A, R223R |
| Bxb1-L10-6 | H95Y, V264A, E434G |
| Bxb1-L10-7 | H95Y, A62A, V466M |
| Bxb1-L11-1 | A280A, A360T |
| Bxb1-L11-2 | L61F, E434G |
| Bxb1-L11-3 | L174L, S231S, A288T, E434G, T463I |
| Bxb1-L11-4 | V40V, A130A, V283V, A288T, E434G, G468D |
| Bxb1-L11-5 | E229K, K313K, A405A, T453I |
| Bxb1-L11-6 | L90L, E229K, N251K, D359N, A360T, V375V, R494R |
| Bxb1-L11-7 | Q92Q, V179I, R181K, E229K, M239I, A360T, R444L |
| Bxb1-L12-1 | E69A, I87L, N251N, H321P, D355N |
| Bxb1-L12-2 | D51N, I87L, R272Q, G489G |
| Bxb1-L12-3 | I87L, del L488 frameshift |
| Bxb1-L12-4 | I87L, V105A, H321N, S328S, R397R, A411V |
| Bxb1-L12-5 | R79R, I87L, Q484K |
| Bxb1-L12-6 | I87L, I137I, F331S, R409H, del L488 frameshift |
| Bxb1-L13-1 | E69A, H95Y, R461R |
| Bxb1-L13-2 | H95Y |
| Bxb1-L13-3 | H95Y, L282L |
| Bxb1-L14-1 | I87L, A369P, F476F |
| Bxb1-L14-2 | G34D, I87L, T166I, E229K, A369P, T435T, G489G |
| Bxb1-L14-3 | I87L, R88R, R140R, K333K, A369P, A414A, V466M, F476F |
| Bxb1-L15-1 | I87L, A369S, E434G |
| Bxb1-L15-2 | I87L, A369P, A414V, A425A, E434G |
| Bxb1-L15-3 | R85R, I87L, A248T, V306V, A369P, A415S, E434G |
| Bxb1-L16-1 | I87L, P160P, V175V, V187V, A218A, E281E, V353I, E419E, A425T, E483E |
| Bxb1-L16-2 | I87L, Q92H, P160P, V175V, P178P, V187V, A218A, E281E, V353I, E419E, A425T, E483E |
| Bxb1-L16-3 | E24E, I87L, H100N, V187V, A218A, E419E, A425T, E483E |
| Bxb1-L16-4 | I87L, V187V, A218A, A369E, E419E, A425T, E483E |
| Bxb1-L16-5 | I87L, V187V, A218A, E419E, A425T, E434G, E483E |
| Bxb1-c1 | — |
| Bxb1-c2 | I87L |
| Bxb1-c3 | H95Y |
| Bxb1-c4 | V122M |
| Bxb1-c5 | A369P |
| Bxb1-c6 | E434G |
| Bxb1-c7 | I87L, H95Y |
| Bxb1-c8 | I87L, V122M |
| Bxb1-c9 | I87L, A369P |
| Bxb1-c10 | I87L, E434G |
| Bxb1-c11 | H95Y, V122M |

TABLE 13-continued

| Bxb1 Mutant | Mutations |
|---|---|
| Bxb1-c12 | H95Y, A369P |
| Bxb1-c13 | H95Y, E434G |
| Bxb1-c14 | V122M, A369P |
| Bxb1-c15 | V122M, E434G |
| Bxb1-c16 | A369P, E434G |
| Bxb1-c17 | I87L, H95Y, V122M |
| Bxb1-c18 | I87L, H95Y, A369P |
| Bxb1-c19 | I87L, H95Y, E434G |
| Bxb1-c20 | I87L, V122M, A369P |
| Bxb1-c21 | I87L, V122M, E434G |
| Bxb1-c22 | I87L, A369P, E434G |
| Bxb1-c23 | H95Y, V122M, A369P |
| Bxb1-c24 | H95Y, V122M, E434G |
| Bxb1-c25 | H95Y, A369P, E434G |
| Bxb1-c26 | V122M, A369P, E434G |
| Bxb1-c27 | I87L, H95Y, V122M, A369P |
| Bxb1-c28 | I87L, H95Y, V122M, E434G |
| Bxb1-c29 | I87L, H95Y, A369P, E434G |
| Bxb1-c30 | I87L, V122M, A369P, E434G |
| Bxb1-c31 | H95Y, V122M, A369P, E434G |
| Bxb1-c32 | I87L, H95Y, V122M, A369P, E434G |
| Bxb1-c33 | L4I, R63K, I87L, H95Y, H111P, V122M, A280T, A369P, E434G, V466M |
| Bxb1-c34 | R63K, V122M |
| Bxb1-R1 | H189Y |
| Bxb1-R2 | D45G |
| Bxb1-R3 | V466L |
| Bxb1-R4 | V76I |
| Bxb1-R5 | R63K, I87V, H100H, N194D, P295P, C307C |
| Bxb1-R6 | R57K, R63K, P295P |
| Bxb1-R7 | V168I |
| Bxb1-R8 | H89Y, A360V |
| Bxb1-R9 | D36N |
| Bxb1-R10 | E445Q |
| Bxb1-R11 | D51G |
| Bxb1-R12 | R181R, A341D |
| Bxb1-R13 | R287H, A425A |
| Bxb1-R14 | V50I, V306A |
| Bxb1-R15 | V366I, R426K |
| Bxb1-R16 | A261S |
| Bxb1-R17 | V74I |
| Bxb1-R18 | D359A, L387L |
| Bxb1-R19 | L263I |
| Bxb1-R20 | Q70H |
| Bxb1-R21 | A49S |
| Bxb1-R22 | D51E |
| Bxb1-R23 | I75V |
| Bxb1-R24 | V175A |

Figure 6:
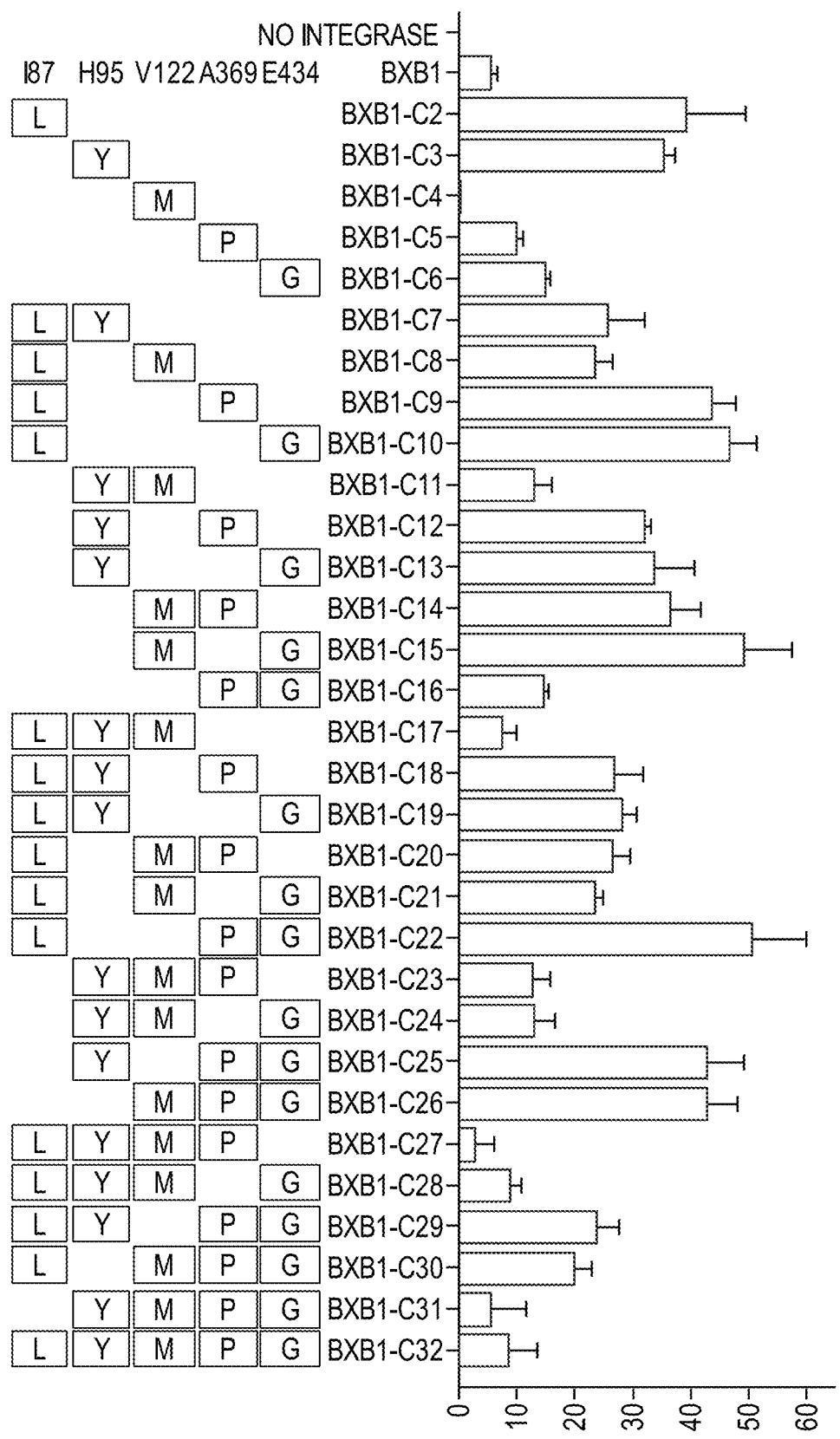
FIG. 6. Comparison of combination mutants on HEK293 ROSA attB cell line. Integration of a 6.6 kb donor plasmid measured by droplet digital PCR. n=4.

Five mutations from top-performing Bxb1 integrase variants isolated from PACE were assembled in all combinations to generate new mutants. To compare activity between mutants independent of PE, helper plasmids encoding combination mutants were co-transfected with a donor plasmid into a clonal HEK293 cell line with a pre-inserted attB site at ROSA26. Notably, combination mutants increased activity over wild-type Bxb1 integrase by up to 9.2-fold (FIG. 6). A variety of synergistic and antagonistic effects were observed. Of the five mutations, I87L and H95Y had the greatest individual effect on integration efficiency (6.4 and 7.1-fold higher than wild-type Bxb1 integrase, respectively), but when combined they were less effective (4.7-fold higher than wild-type Bxb1 integrase). Mutations A369P and E434G had a modest effect on integration activity on their own but exhibited a synergistic effect with every other mutation tested, including V122M, which decreased activity relative to wild-type Bxb1 integrase on its own.

Figure 7:
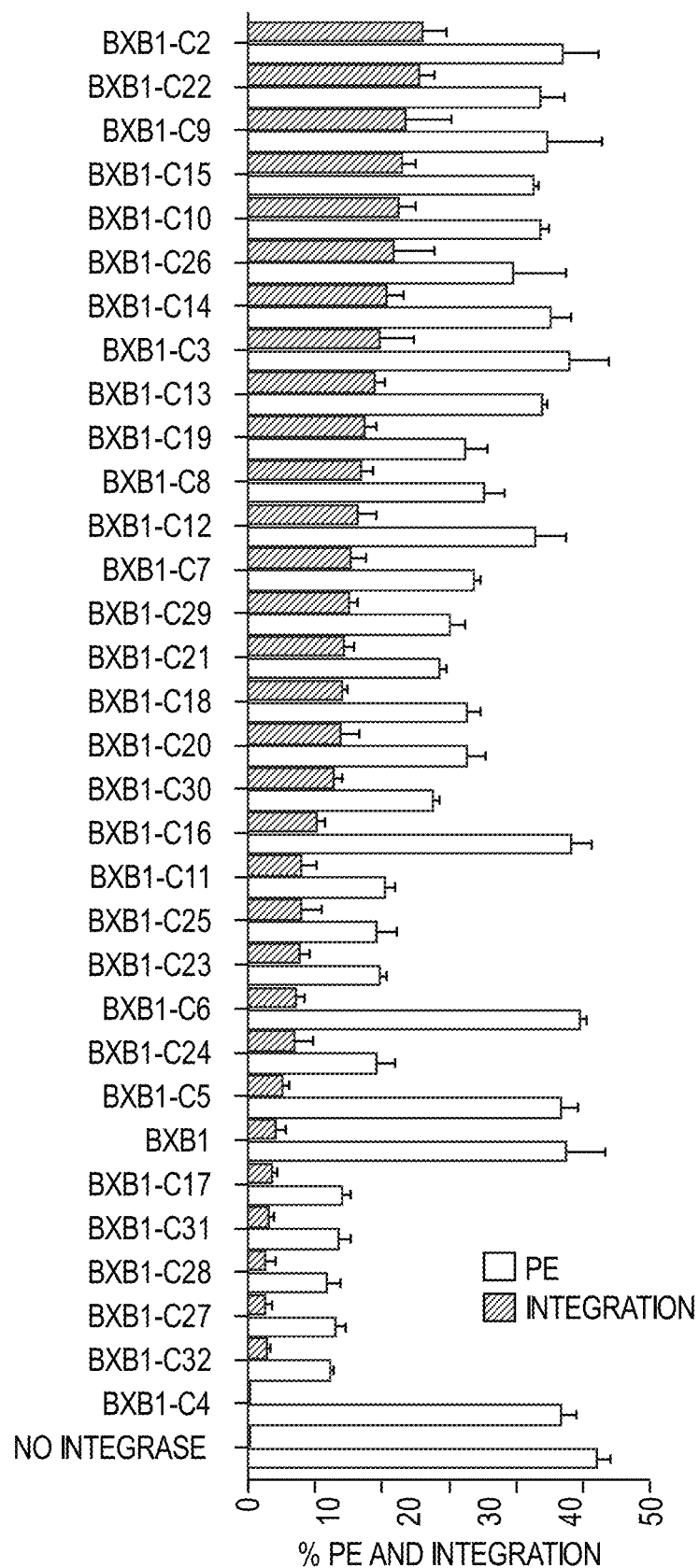
FIG. 7. Integration and twin-PE frequencies in HEK293T cells with selected PACE evolved clones and combination mutants. n=4 on two separate days.

PE was subsequently used to insert the attB site at ROSA26 in HEK293 cells by co-transfecting PE plasmids with combination mutant helper plasmids and a donor plasmid. When combined with PE, combination mutants demonstrated increased activity over wild-type Bxb1 integrase up to 6-fold (FIG. 7). Different patterns of activity were observed for the combination mutants between experiments performed with and without PE (Table 14). For example, Bxb1-c25 had high activity on the clonal cell line and low activity when paired with PE, indicating that the mutations had a negative effect on PE which in turn decreased the integrase's insertion efficiency despite being hyperactive. Similarly, in all cases where H95Y and V122M were combined, PE efficiency decreased significantly (2.3- to 4-fold relative to wild-type Bxb1 integrase). It has been previously shown that the att site found on the epegRNA expression plasmid could recombine the att site on the donor plasmid, rendering both plasmids nonfunctional. This is expected to reduce the amount of epegRNA available for PE as well as reduce the number of donor plasmids available for integrase insertion. To reduce the effect of Bxb1 integrase recombining these plasmids, the epegRNA expression plasmids herein contained a partial att site. During twin PE, although each inserted 3' single strand flap contains only part of the att site, there is enough overlapping sequence to form a double-stranded intermediate. The remaining single-stranded sequence of the att sites can subsequently be filled in to promote insertion of the full att site. While this strategy appears sufficient for preventing unwanted wild-type Bxb1 integrase recombination, it is speculated that certain hyperactive integrase mutants gained activity on the partial att site sequence and recombined the epegRNA expression plasmids, which may explain the reduction in PE efficiency.

AlphaFold modeling of Bxb1 integrase as a dimer revealed that three mutations I87L, H95Y and V122M are in close proximity to each other on the catalytic domain. Mutations A369P and E434G are located together proximal to a predicted leucine zipper motif suggesting they may affect dimerization.

Higher transfection rates were observed for HEK293T compared to HEK293 cells. Top variants were re-assayed using HEK293T cells resulting in insertion efficiencies up to 44.1%, with combination mutants outperforming parent variants (FIG. 7). Furthermore, No off-target insertions were detected by genomic PCR at predicted Bxb1 pseudo sites (Anzalone et al. (2022) Nat. Biotechnol. 40:731-740; Yarnall et al. (2023) Nat. Biotechnol. 41:500-512). Combination mutants were evolved using PACE but variants with further increases in efficiency were not recovered.

The programmable addition via site-specific targeting elements (PASTE) system has been described, which uses single PEG prime editing and a fusion of Bxb1 to the nCas9-RT (Yarnall et al. (2023) Nat. Biotechnol. 41:500-512). Similar to others, lower prime editing efficiencies were observed using a single pegRNA (Wang et al. (2022) Nat. Methods 19(3):331-340; Anzalone et al. (2022) Nat. Biotechnol. 40:731-740), with PASTE prime editing and integration into the ROSA26 locus reaching 11.2% and 2.4%, respectively. PASTE was improved by incorporating twin prime editing pegRNA and it was observed that the fused integrase architecture indeed outperformed traditional twin prime editing with wild-type Bxb1, However, neither traditional PASTE nor twin prime editing PASTE reached the levels of the evolved Bxb1 integrase. Several hyperactive mutations were introduced into both PASTE and twin prime editing PASTE but a further increase in efficiency was not observed.

Figure 8:
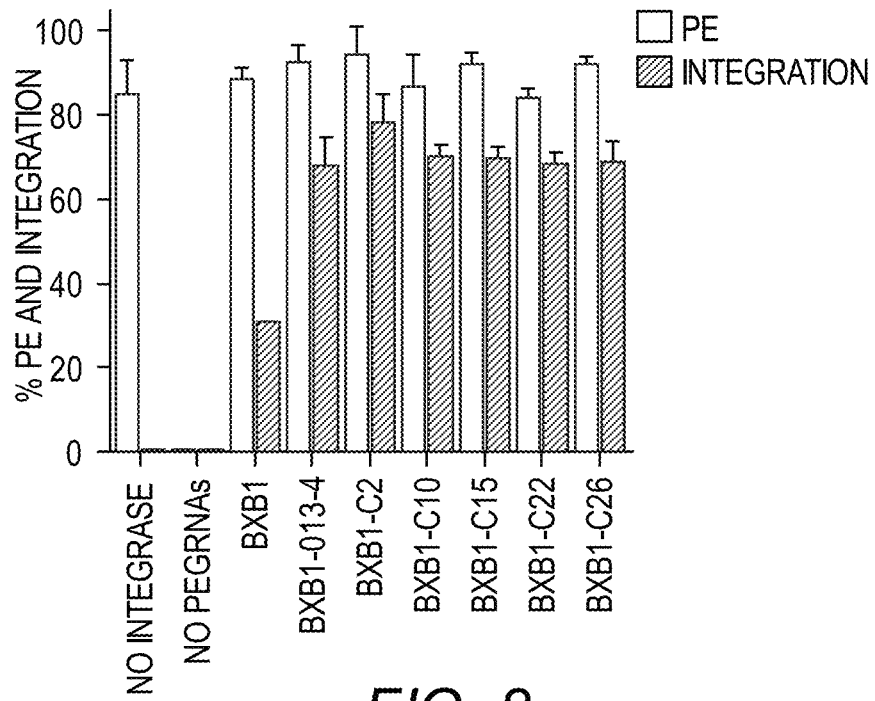
FIG. 8. Optimized twin prime editing and integration in HEK293T. Cells were transfected and sorted 3 days post transfection for dsRed expression before lysis and measurement by droplet digital PCR. n=3.

To exclude the influence of incomplete transfection efficiency, top evolved variants were assayed in HEK293T cells and sorted for DsRed expression. These optimized conditions resulted in insertion rates greater than 80% of target sites (FIG. 8). In a therapeutic context, given that normal cells contain a target site on each of two chromosomes, this efficiency equates to a >96% probability that a cell will receive at least one insertion.

Figure 9:
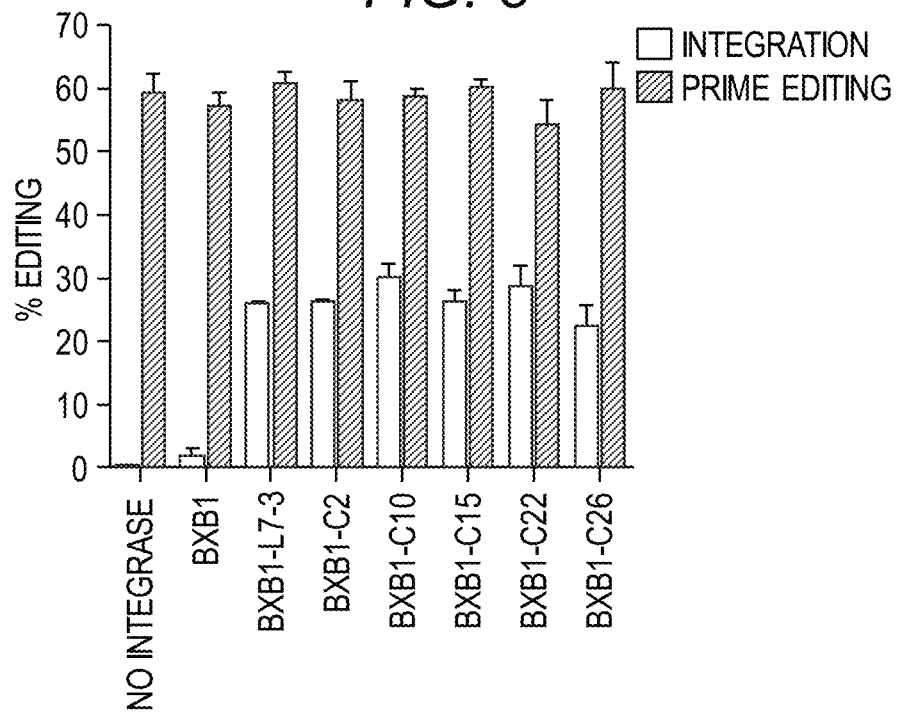
FIG. 9. Optimized twin prime editing and integration in K562. Cells were transfected and sorted 3 days post transfection for dsRed expression before lysis and measurement by droplet digital PCR. n=3.
Figure 10:
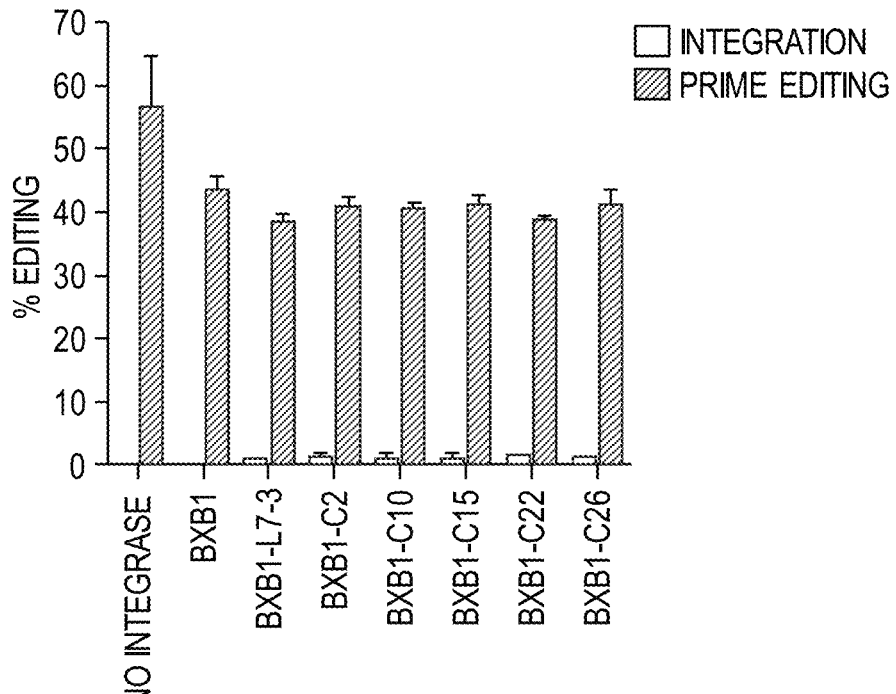
FIG. 10. Optimized twin prime editing and integration in HeLa. Cells were transfected and sorted 3 days post transfection for dsRed expression before lysis and measurement by droplet digital PCR. n=3.

Evolved Bxb1 variants were active on HeLa and K562 cells. Surprisingly, although prime editing was efficient in HeLa cells (>40%), integration was not detected using wild-type Bxb1 integrase. However, evolved integrases successfully performed integration, albeit at low levels. In K562 cells, evolved integrases outperformed wild-type Bxb1 by 11.2-fold (2.7% vs 30.3%; FIG. 9 and FIG. 10).

Figure 11:
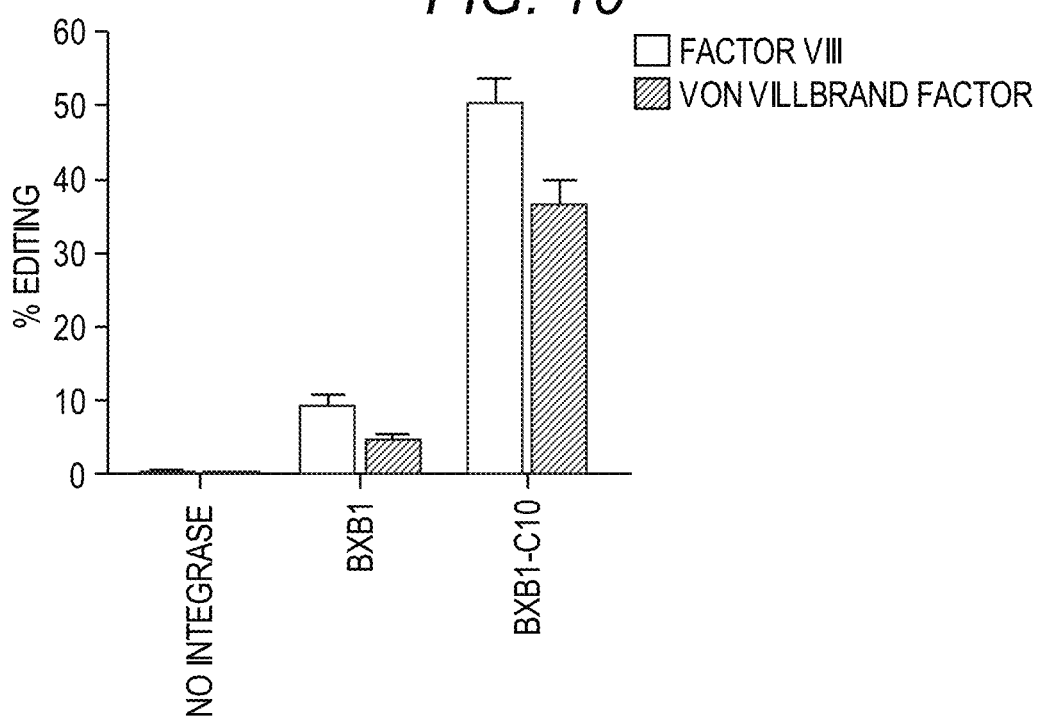
FIG. 11. Droplet digital PCR detection of Human Factor VIII (FVIII) and Von Willebrand Factor (VWF) donor integration at ROSA26.
Figure 12:
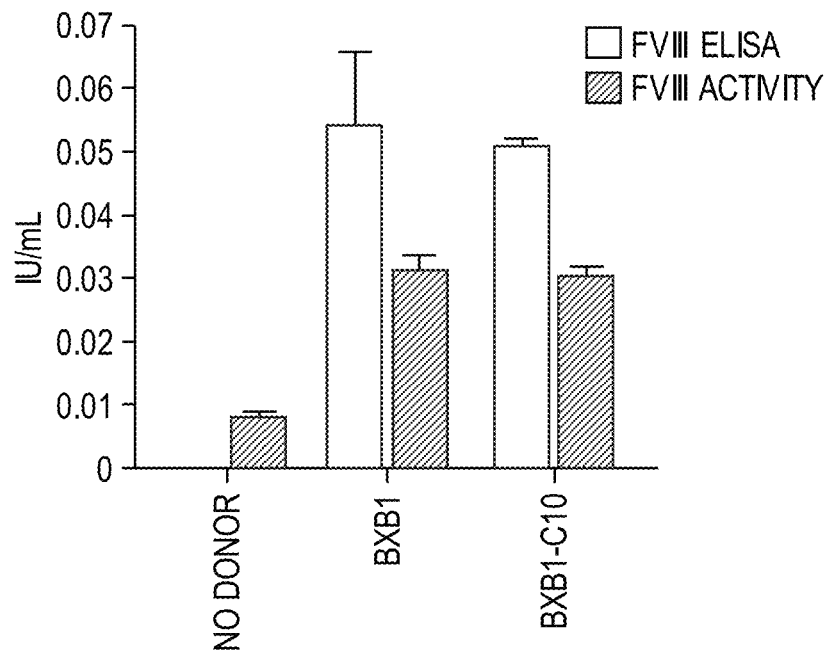
FIG. 12. Detection of secreted FVIII in culture media by ELISA and Factor X activation assay.
Figure 13:
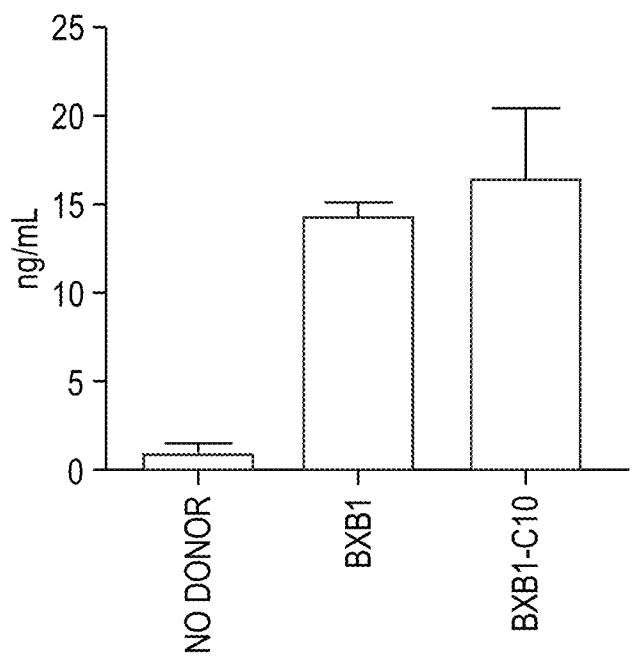
FIG. 13. Detection of secreted VWF in culture media by ELISA.

Integrase insertion of large cargos would enable therapies inaccessible to current methods. Specifically, the full-length Human Factor VIII (FVIII) gene (7 kb cDNA) and Von Willebrand Factor (VWF) gene (8.5 kb cDNA) are not amenable for HDR, AAV, or lentiviral delivery. Prime editing and integrase insertion of 14 kb FVIII (50.5%) and 15.7 kb VWF (36.4%) expression cargos were measured, and expression was verified by ELISA and Factor X activation (FIG. 11 to FIG. 13).

Active insertion by integrases does not rely on host repair and is highly specific for the att sequence that is not present in the unmodified human genome. Importantly, it has been shown that the efficiency of targeted insertion using evolved integrases and prime editing exceeds current approaches. A key finding was that evolved integrases outcompeted wild-type Bxb1 particularly well during pre-optimized transfection conditions (>6 fold) (Table 14) indicating that this technology is suitable for in-vivo gene delivery where tissue transfection efficiency can be challenging.

TABLE 14

| Integrase | Prime Editing | | Integration | |
|---|---|---|---|---|
| | Editing Frequency | Stdev. | Editing Frequency | Stdev. |
| No Integrase | 43.51% | 1.49% | 0.01% | 0.01% |
| Bxb1-c4 | 38.97% | 1.94% | 0.04% | 0.01% |
| Bxb1-c32 | 10.47% | 0.38% | 2.41% | 0.60% |
| Bxb1-c27 | 11.15% | 1.11% | 2.42% | 0.61% |
| Bxb1-c28 | 10.06% | 1.62% | 2.45% | 1.02% |
| Bxb1-c31 | 11.49% | 1.29% | 2.80% | 0.48% |
| Bxb1-c17 | 11.95% | 0.84% | 3.26% | 0.70% |
| WT Bxb1 | 39.57% | 4.85% | 3.66% | 1.19% |
| Bxb1-c5 | 39.05% | 1.91% | 4.45% | 0.68% |
| Bxb1-c24 | 16.13% | 2.13% | 6.08% | 2.04% |
| Bxb1-c6 | 41.33% | 0.63% | 6.17% | 0.97% |
| Bxb1-c23 | 16.57% | 0.75% | 6.57% | 1.21% |
| Bxb1-c25 | 15.97% | 2.50% | 6.88% | 2.43% |
| Bxb1-c11 | 17.20% | 0.94% | 6.92% | 1.77% |
| Bxb1-c16 | 40.27% | 2.49% | 8.74% | 0.90% |
| Bxb1-c30 | 22.93% | 0.78% | 10.89% | 0.98% |
| Bxb1-c20 | 27.17% | 2.41% | 11.68% | 2.15% |
| Bxb1-c18 | 27.25% | 1.74% | 11.94% | 0.49% |
| Bxb1-c21 | 23.90% | 0.98% | 12.22% | 1.04% |
| Bxb1-c29 | 25.26% | 1.68% | 12.73% | 0.88% |
| Bxb1-c7 | 28.25% | 0.75% | 13.05% | 1.87% |
| Bxb1-c12 | 35.80% | 3.68% | 13.83% | 2.20% |
| Bxb1-c8 | 29.40% | 2.63% | 14.39% | 1.20% |
| Bxb1-c19 | 27.07% | 2.75% | 14.76% | 1.26% |
| Bxb1-c13 | 36.53% | 0.68% | 16.07% | 1.12% |
| Bxb1-c3 | 39.99% | 4.86% | 16.66% | 4.04% |
| Bxb1-c14 | 37.80% | 2.45% | 17.59% | 1.93% |
| Bxb1-c26 | 33.05% | 6.52% | 18.35% | 4.97% |
| Bxb1-c10 | 36.48% | 0.89% | 19.09% | 1.78% |
| Bxb1-c15 | 35.55% | 0.60% | 19.19% | 1.66% |
| Bxb1-c9 | 37.34% | 6.71% | 19.91% | 5.51% |
| Bxb1-c22 | 36.49% | 2.85% | 21.44% | 1.89% |
| Bxb1-c2 | 39.05% | 4.50% | 21.85% | 2.94% |

TABLE 15

| Name | Spacer | Spacer SEQ ID NO: | Scaffold | RT Template | RT Template SEQ ID NO: |
|---|---|---|---|---|---|
| aav peg spacer1a attB35 | aagtggttgataaacccacg | 248 | cr772 | ggggagcccaagggcacg ccctggcac | 289 |

TABLE 15-continued

| Name | Spacer | Spacer SEQ ID NO: | Scaffold | RT Template | RT Template SEQ ID NO: |
|---|---|---|---|---|---|
| aav peg spacer1b attB35 | ccggccagtttctccacctg | 249 | cr772 | ggcgtgcccttgggctccc cgggcgcgt | 290 |
| aav peg spacer2a attB35 | caggtaaaactgacgcacgg | 250 | cr772 | ggggagcccaagggcacg ccctggcac | 291 |
| aav peg spacer2b attB35 | gcttccttacacttcccaag | 251 | cr772 | ggcgtgcccttgggctccc cgggcgcgt | 292 |
| aav peg spacer3a attB35 | gatcagtgaaacgcaccaga | 252 | cr772 | ggggagcccaagggcacg ccctggcac | 293 |
| aav peg spacer3b attB35 | gatggagccagagaggatcC | 253 | cr772 | ggcgtgcccttgggctccc cgggcgcgt | 294 |
| aav peg spacer4a attB35 | gcagctcaggttctgggaga | 254 | cr772 | ggggagcccaagggcacg ccctggcac | 295 |
| aav peg spacer1a attP41 | aagtggttgataaacccacg | 255 | cr772 | tggggtaacctttgagttctc tcagttgggggc | 296 |
| aav peg spacer1b attP41 | ccggccagtttctccacctg | 256 | cr772 | actgagagaactcaaaggtt accccagttgggg | 297 |
| aav peg spacer2a attP41 | caggtaaaactgacgcacgg | 257 | cr772 | tggggtaacctttgagttctc tcagttgggggc | 298 |
| aav peg spacer2b attP41 | gcttccttacacttcccaag | 258 | cr772 | actgagagaactcaaaggtt accccagttgggg | 299 |
| aav peg spacer3a attP41 | gatcagtgaaacgcaccaga | 259 | cr772 | tggggtaacctttgagttctc tcagttgggggc | 300 |
| aav peg spacer3b attP41 | gatggagccagagaggatcc | 260 | cr772 | actgagagaactcaaaggtt accccagttgggc | 301 |
| xq22 peg spacer1a attB35 | ctactctaattaaacctgta | 261 | cr772 | ggggagcccaagggcacg ccctggcac | 302 |
| xq22 peg spacer1b attB35 | taatgcctcatttaatctat | 262 | cr772 | ggcgtgcccttgggctccc cggg | 303 |
| xq22 peg spacer2a attB35 | aatgagcaaactctagaatg | 263 | cr772 | ggggagcccaagggcacg ccctggcac | 304 |
| xq22 peg spacer2b attB35 | aatggtccccaggttacatt | 264 | cr772 | ggcgtgcccttgggctccc cgggcgcgt | 305 |
| xq22 peg spacer1a attP41 | ctactctaattaaacctgta | 265 | cr772 | tggggtaacctttgagttctc tcagttggggg | 306 |
| xq22 peg spacer1b attP41 | taatgcctcatttaatctat | 266 | cr772 | actgagagaactcaaaggtt accccagttgggc | 307 |

TABLE 15-continued

| Name | Spacer | Spacer SEQ ID NO: | Scaffold | RT Template | RT Template SEQ ID NO: |
|---|---|---|---|---|---|
| xq22 peg spacer2a attP41 | aatgagcaaactctagaatg | 267 | cr772 | tggggtaacctttgagttctc tcagttgggggc | 308 |
| xq22 peg spacer2b attP41 | aatggtccccaggttacatt | 268 | cr772 | actgagagaactcaaaggtt accccagttggggc | 309 |
| rosa peg spacer1a attB35 | tcgacaccaactctagtccg | 269 | cr772 | ggggagcccaagggcacg ccctggcac | 310 |
| rosa peg spacer1b attB35 | agtcgcttctcgattatgg | 270 | cr772 | ggcgtgcccttgggctccc cgggcgcgt | 311 |
| rosa peg spacer2b attB35 | ccctgggcgttgccctgcag | 271 | cr772 | ggcgtgcccttgggctccc cgggcgcgt | 312 |
| rosa peg spacer3a attB35 | tctcaaatggtataaaactc | 272 | cr772 | ggggagcccaagggcacg ccctggcac | 313 |
| rosa peg spacer3b attB35 | ggagcttagtcattcacctg | 273 | cr772 | ggcgtgcccttgggctccc cgggcgcgt | 314 |
| rosa peg spacer4a attB35 | atgcctggtagggatgcaaa | 274 | cr772 | ggggagcccaagggcacg ccctggcac | 315 |
| rosa peg spacer4b attB35 | caccaccaaagtgtagcatc | 275 | cr772 | ggcgtgcccttgggctccc cgggcgcgt | 316 |
| rosa peg spacer1a attP41 | tcgacaccaactctagtccg | 276 | cr772 | tggggtaacctttgagttctc tcagttgggggc | 317 |
| rosa peg spacer1b attP41 | agtcgcttctcgattatggg | 277 | cr772 | actgagagaactcaaaggtt accccagttggggc | 318 |
| rosa peg spacer2b attP41 | ccctgggcgttgccctgcag | 278 | cr772 | actgagagaactcaaaggtt accccagttgggg | 319 |
| rosa peg spacer3a attP41 | tctcaaatggtataaaactc | 279 | cr772 | tggggtaacctttgagttctc tcagttgggggc | 320 |
| rosa peg spacer3b attP41 | ggagcttagtcattcacctg | 280 | cr772 | actgagagaactcaaaggtt accccagttggggc | 321 |
| rosa peg spacer4a attP41 | atgcctggtagggatgcaaa | 281 | cr772 | tggggtaacctttgagttctc tcagttgggggc | 322 |
| rosa peg spacer4b attP41 | caccaccaaagtgtagcatc | 282 | cr772 | actgagagaactcaaaggtt accccagttggggc | 323 |
| rosa peg spacer4a BxblattP48 | atgcctggtagggatgcaaa | 283 | cr772 | taccgtacaccactgagac cgcggtggttgaccagaca aacct | 324 |
| rosa peg spacer4b Bxb1attP48 | caccaccaaagtgtagcatc | 284 | cr772 | gtctggtcaaccaccgcgg tctcagtggtgtacggtaca aacct | 325 |

TABLE 15-continued

| Name | Spacer | Spacer SEQ ID NO: | Scaffold | RT Template | RT Template SEQ ID NO: |
|---|---|---|---|---|---|
| rosa peg spacer4a Bxb1attB38 | atgcctggtagggatgcaaa | 285 | cr772 | acgacggcggtctccgtcg tcaggatcat | 326 |
| rosa peg spacer4b Bxb1attP38 | caccaccaaagtgtagcatc | 286 | cr772 | acgacggagaccgccgtc gtcgacaagcc | 327 |
| rosa peg spacer 4a pa1 attB | atgcctggtagggatgcaaa | 287 | cr772 | CCTACATGCTCG AAGGGCGTATGC GCC | 328 |
| rosa peg spacer 4b pa1 attB | caccaccaaagtgtagcatc | 288 | cr772 | ACGCCCTTCGAG CATGTAGGTCAC GG | 329 |

TABLE 16

| Name | PBS | PBS SEQ ID NO: | Linker | TevopreQ1 |
|---|---|---|---|---|
| aav peg spacer1a attB35 | gggtttatcaacc | 330 | GGAATGCC | tevopreQ1 |
| aav peg spacer1b attB35 | gtggagaaactgg | 331 | AATTAATG | tevopreQ1 |
| aav peg spacer2a attB35 | tgcgtcagtttta | 332 | AGGTTCAA | tevopreQ1 |
| aav peg spacer2b attB35 | gggaagtgtaagg | 333 | TCAAATGA | tevopreQ1 |
| aav peg spacer3a attB35 | ggtgcgtttcact | 334 | CTATAAGA | tevopreQ1 |
| aav peg spacer3b attB35 | tcctctctggctc | 335 | GTAATAAT | tevopreQ1 |
| aav peg spacer4a attB35 | cccagaacctgag | 336 | AATTAATT | tevopreQ1 |
| aav peg spacer1a attP41 | gggtttatcaacc | 337 | TTCAGACC | tevopreQ1 |
| aav peg spacer1b attP41 | gtggagaaactgg | 338 | AATTATAA | tevopreQ1 |
| aav peg spacer2a attP41 | tgcgtcagtttta | 339 | AAGGTCAC | tevopreQ1 |
| aav peg spacer2b attP41 | gggaagtgtaagg | 340 | CCTCAATT | tevopreQ1 |
| aav peg spacer3a attP41 | ggtgcgtttcact | 341 | TTATAATA | tevopreQ1 |
| aav peg spacer3b attP41 | tcctctctggctc | 342 | AACTGAAA | tevopreQ1 |
| xq22 peg spacer1a attB35 | aggtttaattaga | 343 | TGCCATAA | tevopreQ1 |
| xq22 peg spacer1b attB35 | gattaaatgaggc | 344 | CCGAAGAA | tevopreQ1 |
| xq22 peg spacer2a attB35 | tctagagtttgct | 345 | GCCCGGAT | tevopreQ1 |
| xq22 peg spacer2b attB35 | gtaacctggggac | 346 | GTCCGACA | tevopreQ1 |
| xq22 peg spacer1a attP41 | aggtttaattaga | 347 | TTCCCATC | tevopreQ1 |
| xq22 peg spacer1b attP41 | gattaaatgaggc | 348 | CGAAATGC | tevopreQ1 |
| xq22 peg spacer2a attP41 | tctagagtttgct | 349 | AAGGGACA | tevopreQ1 |
| xq22 peg spacer2b attP41 | gtaacctggggac | 350 | AAGAATTA | tevopreQ1 |
| rosa peg spacer1a attB35 | actagagttggtg | 351 | AATAGTAC | tevopreQ1 |
| rosa peg spacer1b attB35 | ataatcgagaagc | 352 | AAATAACG | tevopreQ1 |
| rosa peg spacer2b attB35 | cagggcaacgccc | 353 | GCTTAACT | tevopreQ1 |
| rosa peg spacer3a attB35 | ttttataccattt | 354 | TACACACG | tevopreQ1 |

TABLE 16-continued

| Name | PBS | PBS SEQ ID NO: | Linker | TevopreQ1 |
|---|---|---|---|---|
| rosa peg spacer3b attB35 | gtgaatgactaag | 355 | AGAAAGAT | tevopreQ1 |
| rosa peg spacer4a attB35 | gcatccctaccag | 356 | ATCTCAGA | tevopreQ1 |
| rosa peg spacer4b attB35 | gctacactttggt | 357 | TATTATAA | tevopreQ1 |
| rosa peg spacer1a attP41 | actagagttggtg | 358 | AAACCCTT | tevopreQ1 |
| rosa peg spacer1b attP41 | ataatcgagaagc | 359 | AAATATAA | tevopreQ1 |
| rosa peg spacer2b attP41 | cagggcaacgccc | 360 | CTTTCAAA | tevopreQ1 |
| rosa peg spacer3a attP41 | tttataccattt | 361 | TTCTACTA | tevopreQ1 |
| rosa peg spacer3b attP41 | gtgaatgactaag | 362 | AATAAGAA | tevopreQ1 |
| rosa peg spacer4a attP41 | gcatccctaccag | 363 | ATCTAATG | tevopreQ1 |
| rosa peg spacer4b attP41 | gctacactttggt | 364 | TAATAACG | tevopreQ1 |
| rosa peg spacer4a BxblattP48 | gcatccctaccag | 365 | AAACCACA | tevopreQ1 |
| rosa peg spacer4b BxblattP48 | gctacactttggt | 366 | CTCATCTT | tevopreQ1 |
| rosa peg spacer4a BxblattB38 | gcatccctaccag | 367 | AACTTCGT | tevopreQ1 |
| rosa peg spacer4b BxblattP38 | gctacactttggt | 368 | CCATATAA | tevopreQ1 |
| rosa peg spacer 4a pa1 attB | gcatccctaccag | 369 | ATCCTACA | tevopreQ1 |
| rosa peg spacer 4b pa1 attB | gctacactttggt | 370 | CCATATAA | tevopreQ1 | cr772 Scaffold:
(SEQ ID NO: 371)
GTTTAAGAGCTAAGCTGGAAACAGCATAGCAAGTTTAAATAAGGCTAGTC
CGTTATCAACTCGAAAGAGTGGCA CCGAGTCGGTGC TevopreQ1:
(SEQ ID NO: 372)
CGCGGTTCTATCTAGTTACGCGTTAAACCAACTAGAA

Example 3: Further Directed Evolution of Bxb1

The Bxb1 integrase of SEQ ID NO:1 was further evolved as described herein to generate additional mutant Bxb1 integrases including combinations of amino acid substitutions (Table 17).

TABLE 17

| Bxb1 Mutant | Mutations |
|---|---|
| Bxb1-c35 | I87L, D45G |
| Bxb1-c36 | I87L, R57K, R63K |
| Bxb1-c37 | I87L, D36N |
| Bxb1-c38 | I87L, A341D |
| Bxb1-c39 | I87L, R287H |
| Bxb1-c40 | I87L, A49S |
| Bxb1-c41 | I87L, A341D, R287H |
| Bxb1-c42 | H95Y, D45G |
| Bxb1-c43 | H95Y, R57K, R63K |
| Bxb1-c44 | H95Y, D36N |
| Bxb1-c45 | H95Y, A341D |
| Bxb1-c46 | H95Y, R287H |
| Bxb1-c47 | H95Y, A49S |
| Bxb1-c48 | H95Y, A341D, R287H |
| Bxb1-c49 | A369P, E434G, D45G |
| Bxb1-c50 | A369P, E434G, R57K, R63K |
| Bxb1-c51 | A369P, E434G, D36N |
| Bxb1-c52 | A369P, E434G, A341D |
| Bxb1-c53 | A369P, E434G, R287H |
| Bxb1-c54 | A369P, E434G, A49S |
| Bxb1-c55 | A369P, E434G, A341D, R287H |
| Bxb1-c56 | I87L, A369P, E434G, D45G |
| Bxb1-c57 | I87L, A369P, E434G, R57K, R63K |
| Bxb1-c58 | I87L, A369P, E434G, D36N |
| Bxb1-c59 | I87L, A369P, E434G, A341D |
| Bxb1-c60 | I87L, A369P, E434G, R287H |
| Bxb1-c61 | I87L, A369P, E434G, A49S |
| Bxb1-c62 | I87L, A369P, E434G, A341D, R287H |
| Bxb1-c63 | V122M, A369P, E434G, D45G |
| Bxb1-c64 | V122M, A369P, E434G, R57K, R63K |
| Bxb1-c65 | V122M, A369P, E434G, D36N |
| Bxb1-c66 | V122M, A369P, E434G, A341D |
| Bxb1-c67 | V122M, A369P, E434G, R287H |
| Bxb1-c68 | V122M, A369P, E434G, A49S |
| Bxb1-c69 | V122M, A369P, E434G, A341D, R287H |
| Bxb1-c71 | V76I, E434G |
| Bxb1-c72 | V76I, A369P, E434G |
| Bxb1-c73 | I87L, E434G, D36E |
| Bxb1-c74 | V122M, E434G, D36E |
| Bxb1-c75 | V76I, I87L |
| Bxb1-c76 | V76I, I87L, A369P, E434G |
| Bxb1-c77 | V76I, V122M, A369P, E434G |
| Bxb1-c78 | I87L, V175A |
| Bxb1-c79 | I87L, V175A, A369P, E434G |
| Bxb1-c80 | V122M, V175A, A369P, E434G |
| Bxb1-c81 | R63K, I87L |
| Bxb1-c82 | R63K, I87L, A369P, E434G |
| Bxb1-c83 | R63K, V122M, A369P, E434G |

TABLE 17-continued

| Bxb1 Mutant | Mutations |
|---|---|
| Bxb1-c84 | I87L, N194D |
| Bxb1-c85 | I87L, N194D, A369P, E434G |
| Bxb1-c86 | V122M, N194D, A369P, E434G |
| Bxb1-c87 | I87L, V175A, N194D |
| Bxb1-c88 | I87L, V175A, N194D, A369P, E434G |
| Bxb1-c89 | V122M, V175A, N194D, A369P, E434G |
| Bxb1-c90 | I87L, V175A, D359A |
| Bxb1-c91 | I87L, V175A, D359A, A369P, E434G |
| Bxb1-c92 | V122M, V175A, D359A, A369P, E434G |
| Bxb1-c93 | R57K, I87L |
| Bxb1-c94 | R57K, I87L, A369P, E434G |
| Bxb1-c95 | R57K, V122M, A369P, E434G |
| Bxb1-c96 | D36E, V76I |
| Bxb1-c97 | V175A, N194D |
| Bxb1-c98 | R63K, V76I |
| Bxb1-c99 | D36N, R63K |
| Bxb1-c100 | V76I, N194D |
| Bxb1-c101 | D36N, V76I, I87L |
| Bxb1-c103 | V76I, I87L, R63K |
| Bxb1-c105 | I87L, A369P, E434G, D36E, V76I |
| Bxb1-c107 | D36N, R63K, V76I, I87L, A369P, E434G |
| Bxb1-c108 | D36N, R63K, V76I, V175A |
| Bxb1-c109 | V74I, I75V |
| Bxb1-c110 | V74I, V76I |
| Bxb1-c111 | V74I |
| Bxb1-c113 | I75V, V76I |
| Bxb1-c114 | V76I |
| Bxb1-c116 | I75V |
| Bxb1-c117 | I87L, D359A |
| Bxb1-c118 | I87L, D359A, A369P, E434G |
| Bxb1-c119 | V122M, D359A, A369P, E434G |
| Bxb1-c120 | L4I, I87L |
| Bxb1-c121 | I87L, H111P |
| Bxb1-c122 | I87L, A119S |
| Bxb1-c123 | I87L, R319K |
| Bxb1-c124 | I87L, A425T |
| Bxb1-c125 | I87L, V179A |
| Bxb1-c126 | V40I, I87L |
| Bxb1-c127 | I87L, V466M |
| Bxb1-c128 | I87L, K313R |
| Bxb1-c129 | E42K, I87L |
| Bxb1-c130 | I87L, L479I |
| Bxb1-c131 | L4I, H95Y, A369P, E434G |
| Bxb1-c132 | H95Y, H111P, A369P, E434G |
| Bxb1-c133 | H95Y, A119S, A369P, E434G |
| Bxb1-c134 | H95Y, R319K, A369P, E434G |
| Bxb1-c135 | H95Y, A369P, A425T, E434G |
| Bxb1-c136 | H95Y, V179A, A369P, E434G |
| Bxb1-c137 | V40I, H95Y, A369P, E434G |
| Bxb1-c138 | H95Y, A369P, E434G, V466M |
| Bxb1-c139 | H95Y, K313R, A369P, E434G |
| Bxb1-c140 | E42K, H95Y, A369P, E434G |
| Bxb1-c141 | H95Y, A369P, E434G, L479I |
| Bxb1-c142 | L4I, I87L, A369P, E434G |
| Bxb1-c143 | I87L, H111P, A369P, E434G |
| Bxb1-c144 | I87L, A119S, A369P, E434G |
| Bxb1-c145 | I87L, R319K, A369P, E434G |
| Bxb1-c146 | I87L, A369P, A425T, E434G |
| Bxb1-c147 | L4I, V122M, A369P, E434G |
| Bxb1-c148 | H111P, V122M, A369P, E434G |
| Bxb1-c149 | A119S, V122M, A369P, E434G |
| Bxb1-c150 | V122M, R319K, A369P, E434G |
| Bxb1-c151 | V122M, A369P, A425T, E434G |
| Bxb1-c152 | L4I, V76I |
| Bxb1-c153 | V76I, H111P |
| Bxb1-c154 | V76I, A119S |
| Bxb1-c155 | L4I, D36N |
| Bxb1-c156 | D36N, H111P |
| Bxb1-c157 | D36N, A119S |
| Bxb1-c158 | L4I, A369P, E434G |
| Bxb1-c159 | H111P, A369P, E434G |
| Bxb1-c160 | A119S, A369P, E434G |
| Bxb1-c161 | V40I, A369P, E434G |
| Bxb1-c162 | E42K, A369P, E434G |

As demonstrated elsewhere herein, evolved Bxb1 integrases outcompeted wild-type Bxb1 (Tables 18 and 19).

TABLE 18

| | Prime Editing | | Integration | |
|---|---|---|---|---|
| Integrase | Editing Frequency | Stdev. | Editing Frequency | Stdev. |
| No Integrase | 49.11% | 1.55% | 0.00% | 0.00% |
| WT Bxb1 | 50.93% | 4.08% | 9.61% | 0.94% |
| Bxb1-c2 | 39.79% | 2.58% | 12.92% | 1.17% |
| Bxb1-c35 | 29.81% | 2.84% | 3.09% | 0.41% |
| Bxb1-c36 | 55.21% | 2.78% | 29.04% | 0.90% |
| Bxb1-c37 | 52.28% | 3.22% | 28.64% | 2.10% |
| Bxb1-c38 | 50.63% | 1.92% | 21.92% | 0.94% |
| Bxb1-c39 | 49.15% | 2.21% | 22.38% | 1.63% |
| Bxb1-c40 | 53.21% | 3.72% | 26.07% | 1.06% |
| Bxb1-c41 | 50.73% | 2.06% | 16.11% | 0.54% |
| Bxb1-c42 | 35.91% | 0.41% | 4.63% | 0.23% |
| Bxb1-c43 | 55.77% | 1.08% | 24.76% | 0.83% |
| Bxb1-c44 | 54.69% | 2.76% | 23.67% | 2.02% |
| Bxb1-c45 | 54.19% | 2.12% | 17.62% | 1.15% |
| Bxb1-c46 | 49.82% | 0.73% | 15.92% | 0.46% |
| Bxb1-c47 | 50.15% | 0.74% | 23.59% | 1.26% |
| Bxb1-c48 | 45.72% | 1.09% | 7.43% | 0.18% |
| Bxb1-c16 | 43.40% | 1.77% | 10.93% | 1.50% |
| Bxb1-c49 | 44.39% | 0.95% | 16.74% | 0.50% |
| Bxb1-c50 | 47.31% | 2.01% | 12.75% | 0.77% |
| Bxb1-c51 | 47.59% | 1.27% | 14.16% | 0.10% |
| Bxb1-c52 | 46.47% | 1.18% | 8.66% | 0.44% |
| Bxb1-c53 | 49.94% | 1.10% | 10.19% | 0.45% |
| Bxb1-c54 | 46.19% | 0.77% | 16.48% | 0.34% |
| Bxb1-c55 | 47.00% | 1.99% | 4.78% | 0.44% |
| Bxb1-c22 | 51.54% | 1.39% | 26.97% | 0.68% |
| Bxb1-c56 | 24.92% | 2.63% | 1.72% | 0.30% |
| Bxb1-c57 | 47.79% | 0.38% | 25.21% | 1.07% |
| Bxb1-c58 | 47.36% | 0.68% | 24.71% | 1.37% |
| Bxb1-c59 | 51.57% | 0.38% | 23.59% | 0.45% |
| Bxb1-c60 | 47.67% | 2.70% | 22.02% | 1.68% |
| Bxb1-c61 | 50.78% | 3.08% | 26.73% | 1.82% |
| Bxb1-c62 | 45.81% | 2.34% | 19.16% | 1.77% |
| Bxb1-c26 | 44.72% | 1.59% | 23.23% | 1.33% |
| Bxb1-c63 | 23.13% | 1.47% | 2.53% | 0.14% |
| Bxb1-c64 | 45.74% | 0.55% | 23.05% | 0.40% |
| Bxb1-c65 | 46.96% | 0.48% | 24.99% | 0.38% |
| Bxb1-c66 | 44.30% | 2.64% | 18.19% | 2.53% |
| Bxb1-c67 | 47.63% | 0.85% | 23.04% | 0.80% |
| Bxb1-c68 | 43.37% | 1.94% | 17.42% | 1.63% |
| Bxb1-c69 | 47.23% | 0.31% | 16.53% | 1.05% |

TABLE 19

| | Prime Editing | | Integration | |
|---|---|---|---|---|
| Integrase | Editing Frequency | Stdev. | Editing Frequency | Stdev. |
| No Integrase | 79.24% | 1.04% | 0.00% | 0.00% |
| WT Bxb1 | 79.17% | 0.07% | 25.85% | 0.29% |
| Bxb1-c22 | 87.65% | 0.67% | 50.61% | 1.92% |
| Bxb1-c2 | 88.07% | 2.33% | 46.18% | 4.19% |
| Bxb1-c26 | 75.74% | 0.55% | 35.22% | 1.61% |
| Bxb1-c71 | 81.38% | 0.61% | 37.69% | 0.03% |
| Bxb1-c72 | 85.05% | 0.18% | 44.18% | 1.95% |
| Bxb1-c73 | 72.33% | 0.35% | 32.08% | 0.41% |
| Bxb1-c74 | 76.91% | 2.32% | 34.79% | 1.70% |
| Bxb1-c75 | 67.89% | 3.40% | 25.16% | 2.68% |
| Bxb1-c76 | 69.08% | 2.28% | 25.26% | 1.07% |
| Bxb1-c77 | 65.78% | 1.04% | 25.70% | 0.31% |
| Bxb1-c78 | 66.80% | 1.81% | 26.65% | 2.02% |
| Bxb1-c79 | 74.70% | 1.77% | 33.37% | 1.80% |
| Bxb1-c80 | 87.37% | 1.06% | 51.83% | 1.83% |
| Bxb1-c81 | 85.81% | 0.04% | 48.94% | 1.29% |
| Bxb1-c82 | 82.12% | 1.06% | 44.28% | 0.53% |
| Bxb1-c83 | 86.04% | 1.78% | 46.53% | 0.44% |
| Bxb1-c84 | 81.58% | 0.96% | 38.90% | 0.32% |
| Bxb1-c85 | 81.61% | 1.81% | 36.61% | 0.35% |
| Bxb1-c86 | 68.62% | 0.37% | 22.77% | 0.77% |
| Bxb1-c87 | 70.83% | 0.22% | 17.80% | 0.12% |
| Bxb1-c88 | 73.89% | 1.14% | 23.31% | 0.63% |

TABLE 19-continued

| Integrase | Prime Editing Editing Frequency | Stdev. | Integration Editing Frequency | Stdev. |
|---|---|---|---|---|
| Bxb1-c89 | 69.51% | 0.31% | 21.08% | 0.64% |
| Bxb1-c90 | 83.90% | 0.69% | 46.54% | 1.72% |
| Bxb1-c91 | 68.32% | 1.58% | 27.84% | 0.48% |
| Bxb1-c92 | 78.52% | 1.04% | 42.75% | 0.20% |
| Bxb1-c93 | 73.92% | 1.58% | 32.51% | 0.87% |
| Bxb1-c94 | 82.06% | 3.61% | 42.67% | 3.28% |
| Bxb1-c95 | 78.00% | 2.56% | 36.61% | 0.83% |
| Bxb1-c96 | 74.01% | 1.88% | 25.84% | 1.38% |
| Bxb1-c97 | 72.68% | 1.11% | 11.24% | 0.16% |
| Bxb1-c98 | 83.42% | 1.93% | 33.31% | 0.05% |
| Bxb1-c99 | 82.67% | 1.95% | 29.75% | 1.38% |
| Bxb1-c100 | 75.64% | 2.78% | 20.30% | 0.53% |
| Bxb1-c101 | 78.73% | 1.28% | 33.54% | 0.20% |
| Bxb1-c103 | 75.27% | 2.89% | 36.69% | 2.84% |
| Bxb1-c105 | 72.70% | 0.37% | 33.25% | 0.56% |
| Bxb1-c107 | 70.06% | 3.06% | 25.34% | 1.83% |
| Bxb1-c108 | 73.37% | 1.33% | 30.09% | 0.61% |
| Bxb1-c109 | 83.45% | 0.23% | 43.86% | 1.17% |
| Bxb1-c110 | 84.97% | 0.84% | 45.47% | 0.66% |
| Bxb1-c111 | 79.40% | 1.13% | 33.49% | 2.61% |
| Bxb1-c113 | 80.24% | 1.37% | 41.60% | 2.32% |
| Bxb1-c114 | 81.91% | 1.16% | 31.52% | 0.45% |
| Bxb1-c116 | 83.41% | 1.98% | 41.69% | 0.07% |
| Bxb1-c117 | 82.20% | 0.73% | 45.68% | 0.56% |
| Bxb1-c118 | 83.11% | 0.76% | 48.18% | 2.50% |
| Bxb1-c119 | 82.72% | 0.92% | 49.67% | 0.55% |
| Bxb1-c120 | 80.14% | 1.65% | 45.48% | 2.48% |
| Bxb1-c121 | 60.79% | 2.14% | 8.57% | 0.03% |
| Bxb1-c122 | 74.89% | 2.82% | 33.19% | 0.48% |
| Bxb1-c123 | 85.72% | 2.20% | 44.23% | 3.63% |
| Bxb1-c124 | 81.55% | 0.13% | 44.94% | 0.84% |
| Bxb1-c125 | 82.44% | 1.38% | 41.34% | 0.80% |
| Bxb1-c126 | 80.87% | 2.55% | 44.45% | 2.57% |
| Bxb1-c127 | 84.60% | 2.55% | 48.58% | 0.88% |
| Bxb1-c128 | 84.93% | 1.12% | 46.44% | 2.28% |
| Bxb1-c129 | 84.29% | 1.76% | 44.91% | 3.18% |
| Bxb1-c130 | 84.49% | 1.19% | 44.77% | 2.61% |
| Bxb1-c131 | 82.52% | 0.20% | 47.52% | 1.06% |
| Bxb1-c132 | 57.30% | 0.86% | 11.07% | 0.28% |
| Bxb1-c133 | 66.87% | 0.43% | 24.46% | 0.56% |
| Bxb1-c134 | 83.49% | 0.23% | 43.57% | 1.16% |
| Bxb1-c135 | 82.88% | 0.13% | 44.72% | 0.06% |
| Bxb1-c136 | 80.87% | 0.69% | 42.13% | 0.67% |
| Bxb1-c137 | 81.64% | 0.84% | 47.90% | 1.32% |
| Bxb1-c138 | 85.77% | 1.48% | 46.63% | 2.67% |
| Bxb1-c139 | 81.46% | 0.15% | 40.54% | 2.15% |
| Bxb1-c140 | 83.43% | 0.55% | 42.39% | 0.17% |
| Bxb1-c141 | 80.05% | 2.03% | 44.04% | 0.33% |
| Bxb1-c142 | 80.59% | 1.45% | 43.43% | 1.06% |
| Bxb1-c143 | 56.52% | 1.71% | 8.72% | 0.81% |
| Bxb1-c144 | 66.03% | 0.09% | 24.49% | 0.54% |
| Bxb1-c145 | 86.33% | 1.44% | 45.19% | 0.09% |
| Bxb1-c146 | 85.79% | 1.16% | 48.03% | 2.63% |
| Bxb1-c147 | 79.61% | 1.01% | 45.01% | 1.26% |
| Bxb1-c148 | 57.59% | 1.75% | 9.46% | 0.23% |
| Bxb1-c149 | 77.38% | 1.64% | 37.42% | 0.46% |
| Bxb1-c150 | 83.43% | 0.50% | 45.31% | 1.17% |
| Bxb1-c151 | 82.98% | 2.07% | 48.04% | 2.11% |
| Bxb1-c152 | 79.90% | 1.67% | 40.97% | 2.78% |
| Bxb1-c153 | 64.72% | 2.12% | 17.22% | 1.27% |
| Bxb1-c154 | 83.55% | 0.71% | 50.51% | 3.56% |
| Bxb1-c155 | 82.06% | 1.53% | 33.17% | 0.87% |
| Bxb1-c156 | 71.23% | 4.05% | 25.56% | 1.41% |
| Bxb1-c157 | 83.86% | 2.41% | 49.37% | 2.50% |
| Bxb1-c158 | 80.07% | 2.53% | 40.24% | 1.36% |
| Bxb1-c159 | 70.51% | 4.18% | 28.53% | 0.16% |
| Bxb1-c160 | 82.10% | 0.89% | 47.74% | 2.00% |
| Bxb1-c161 | 80.71% | 1.13% | 36.46% | 1.23% |
| Bxb1-c162 | 78.70% | 1.38% | 36.73% | 2.97% |

Additional amino acid substitutions were introduced at positions 87, 91, 95 and 98 of Bxb1 or SEQ ID NO:1. Prime editing efficiency and integration of these mutants were analyzed (Table 20).

TABLE 20

| Integrase mutations | Prime Editing Editing Frequency | Stdev. | Integration Editing Frequency | Stdev. |
|---|---|---|---|---|
| No Integrase | 70.57% | 57.85% | 0.01% | 0.01% |
| WT Bxb1 | 73.27% | 60.05% | 20.48% | 16.79% |
| I87L A369P E434G | 74.27% | 60.87% | 46.44% | 38.05% |
| I87D | 41.97% | 34.40% | 1.23% | 1.01% |
| I87K | 41.60% | 34.10% | 1.56% | 1.28% |
| I87H | 43.94% | 36.01% | 4.19% | 3.43% |
| I87Y | 39.06% | 32.02% | 1.93% | 1.58% |
| I87L | 75.71% | 62.06% | 45.44% | 37.24% |
| I87A | 69.71% | 57.14% | 41.93% | 34.37% |
| I87S | 61.76% | 50.62% | 29.38% | 24.08% |
| Q91E | 72.63% | 59.53% | 0.31% | 0.26% |
| Q91K | 68.04% | 55.77% | 0.02% | 0.01% |
| Q91Y | 69.42% | 56.90% | 0.04% | 0.03% |
| Q91L | 73.04% | 59.87% | 2.12% | 1.74% |
| Q91A | 70.04% | 57.41% | 0.00% | 0.00% |
| Q91S | 69.48% | 56.95% | 0.02% | 0.01% |
| H95D | 42.61% | 34.93% | 2.17% | 1.78% |
| H95K | 70.13% | 57.48% | 0.16% | 0.13% |
| H95Y | 73.54% | 60.28% | 37.62% | 30.84% |
| H95L | 67.35% | 55.21% | 2.57% | 2.11% |
| H95A | 74.70% | 61.23% | 1.84% | 1.51% |
| H95S | 69.82% | 57.23% | 0.54% | 0.45% |
| E98D | 76.67% | 62.85% | 18.48% | 15.15% |
| E98K | 76.11% | 62.39% | 3.16% | 2.59% |
| E98H | 75.89% | 62.21% | 4.55% | 3.73% |
| E98Y | 70.86% | 58.09% | 12.20% | 10.00% |
| E98L | 71.81% | 58.86% | 4.73% | 3.88% |
| E98A | 72.45% | 59.38% | 3.18% | 2.61% |
| E98S | 75.12% | 61.57% | 14.99% | 12.29% |

Example 4: Combinations of Mutations of Bxb1

In some aspects, an evolved Bxb1 integrase may include a mutation (e.g., an amino acid substitution) at one or more of positions I87 to H100 of SEQ ID NO:1, or any position or range of positions therein. In certain aspects, an evolved Bxb1 integrase includes an amino acid substitution at position I87, H89, Q91, Q92, H95, E98, D99 and/or H100 of SEQ ID NO:1, e.g., I87L, I87V, I87A, I87S, I87D, I87K, I87H, I87Y, H89Y, H89G, Q91E, Q91K, Q91Y, Q91L, Q91A, Q91S, Q92H, H95Y, H95D, H95K, H95L, H95A, H95S, E98D, E98K, E98H, E98Y, E98L, E98A, E98S, D99N, and/or H100N.

In some aspects, an evolved Bxb1 integrase may include a mutation (e.g., an amino acid substitution) at one or more of positions K101 to P117 of SEQ ID NO:1, or any position or range of positions therein. In certain aspects, an evolved Bxb1 integrase includes an amino acid substitution at position V105, A110, and/or H111 of SEQ ID NO:1, e.g., V105A, A110T and/or H111P.

In some aspects, an evolved Bxb1 integrase may include a mutation (e.g., an amino acid substitution) at one or more of positions F118 to I137 of SEQ ID NO:1, or any position or range of positions therein. In certain aspects, an evolved Bxb1 integrase includes an amino acid substitution at positions A119 and/or V122 of SEQ ID NO:1, e.g., A119S and/or V122M.

In some aspects, an evolved Bxb1 integrase may include a mutation (e.g., an amino acid substitution) at one or more of positions A3 to I7, V74 to V76, and/or L103 to V105 of SEQ ID NO:1, or any position or range of positions therein. In certain aspects, an evolved Bxb1 integrase includes an amino acid substitution, e.g., a conservative amino acid substitution, at position L4, V74, I75, V76, and/or V105 of SEQ ID NO:1, e.g., L4I, V74I, I75V, V76I, and/or V105A.

In some aspects, an evolved Bxb1 integrase may include a mutation (e.g., an amino acid substitution) at one or more of positions P19 to Q32, P59 to A66, and/or V80 to L83 of SEQ ID NO:1, or any position or range of positions therein. In certain aspects, an evolved Bxb1 integrase includes an amino acid substitution at position L61 and/or R63 of SEQ ID NO:1, e.g., L61F and/or R63K.

In some aspects, an evolved Bxb1 integrase may include a mutation (e.g., an amino acid substitution) at one or more of positions G39 to L44 of SEQ ID NO:1, or any position or range of positions therein. In certain aspects, an evolved Bxb1 integrase includes an amino acid substitution at position V40 and/or E42 of SEQ ID NO:1, e.g., V40I, V40A and/or E42K.

In some aspects, an evolved Bxb1 integrase may include a mutation (e.g., an amino acid substitution) at one or more of positions R33 to V38, F67 to D73, and/or S106 to P117 of SEQ ID NO:1, or any position or range of positions therein. In certain aspects, an evolved Bxb1 integrase includes an amino acid substitution at position G34, D36, F67, E69, Q70, V105, and/or S106, A110, and/or H111 of SEQ ID NO:1, e.g., G34D, D36A, D36N, F67S, E69A, Q70H, V105A, A110T and/or H111P.

In some aspects, an evolved Bxb1 integrase may include a mutation (e.g., an amino acid substitution) at one or more of positions A374 to G422 of SEQ ID NO:1, or any position or range of positions therein. In certain aspects, an evolved Bxb1 integrase includes an amino acid substitution at position V380, T388, A398, R409, A411, A414, A415 and/or R416 of SEQ ID NO:1, e.g., V380I, T388M, A398S, R409H, A411V, A414V, A415S, and/or R416K.

In some aspects, an evolved Bxb1 integrase may include a mutation (e.g., an amino acid substitution) at one or more of positions D359 to A374 and/or L423 to R438 of SEQ ID NO:1, or any position or range of positions therein. In certain aspects, an evolved Bxb1 integrase includes an amino acid substitution at position D359, A360, R362, A369, A425, R426, R433 and/or E434 of SEQ ID NO:1, e.g., D359A, D359N, A360T, A360V, R362K, V366I, A369E, A369P, A369T, A369S, A425T, R426K, R433K, and/or E434G.

What is claimed is:

1. A Bxb1 integrase comprising:
   an amino acid sequence that is at least 98% identical to the amino acid sequence of SEQ ID NO: 1; and
   one or more amino acid mutations at positions selected from L4I, E42K, R57K, R63K, V76I, H111P, V122M, and V187I, relative to SEQ ID NO: 1.

2. The Bxb1 integrase of claim 1, comprising an amino acid sequence that is at least 99% identical to the amino acid sequence of SEQ ID NO: 1.

3. The Bxb1 integrase of claim 1, further comprising one or more amino acid mutations selected from D36N, V40A, A49S, V74I, I87L or I87A or I87S, H89G, V175A, V179A, R287H, A288V, T453I, and H496N.

4. The Bxb1 integrase of claim 1, further comprising one or more amino acid mutations selected from V40I, D45G, I75V, H95Y, A119S, A280T, A311V, E434G, and V466M.

5. The Bxb1 integrase of claim 1, wherein one or more of the following amino acids relative to SEQ ID NO: 1 are not mutated: A62, H100, G209, P295, L302, C307, L387, E419, S428, E483, and R487.

6. The Bxb1 integrase of claim 1, comprising the mutation V122M.

7. The Bxb1 integrase of claim 6, further comprising the mutation A369P.

8. A Bxb1 integrase comprising an amino acid sequence that is at least 99% identical to the amino acid sequence of SEQ ID NO: 1 and having the amino acid mutations I87L, A369P, and E434G; the amino acid mutations V122M, A369P, and E434G; or the amino acid mutations H95Y, A369P, and E434G.

9. A Bxb1 integrase comprising:
   an amino acid sequence that is at least 98% identical to the amino acid sequence of SEQ ID NO: 1; and
   one or more amino acid mutations selected from R319K, A341D, D359A, A369P, A398S, R416K, A425T, L479I, and M499T, relative to SEQ ID NO: 1.

10. The Bxb1 integrase of claim 9, comprising an amino acid that is at least 99% identical to the amino acid sequence of SEQ ID NO: 1.

11. The Bxb1 integrase of claim 9, further comprising one or more amino acid mutations selected from D36N, V40A, A49S, V74I, I87L or I87A or I87S, H89G, V175A, V179A, R287H, A288V, T453I, and H496N.

12. The Bxb1 integrase of claim 9, further comprising one or more amino acid mutations selected from V40I, D45G, I75V, H95Y, A119S, A280T, A311V, E434G, and V466M.

13. The Bxb1 integrase of claim 9, wherein one or more of the following amino acids relative to SEQ ID NO: 1 are not mutated: A62, H100, Q191, P195, G209, P295, L302, C307, L387, E419, S428, E483, and R487.

14. The Bxb1 integrase of claim 9, further comprising the mutation V122M.

15. The Bxb1 integrase of claim 9, comprising the mutation A369P.

16. A Bxb1 integrase comprising:
an amino acid sequence that is at least 98% identical to the amino acid sequence of SEQ ID NO: 1; and
a combination of amino acid mutations selected from:
A119S, A369P, and E434G;
A288V, A311V, A398S, R416K, T453I, H496N, and E42K,
A369P and E434G;
A49S, A369P, and E434G;
A49S, I87L, A369P, and E434G;
A49S, V122M, A369P, and E434G;
D36N, A369P, and E434G;
D36N, I87L, A369P, and E434G;
D36N, V122M, A369P, and E434G;
D45G, A369P, and E434G;
E42K, H95Y, A369P, and E434G;
E42K, V76I, and I87L;
H111P and E434G
H95, V122M and A369P;
H95Y and A341D;
H95Y and A369P;
H95Y and K313R;
H95Y and V122M;
H95Y, A369P, A425T, and E434G;
H95Y, A369P, and E434G;
H95Y, A369P, E434G, and L479I;
H95Y, A369P, E434G, and V466M;
H95Y, R319K, A369P, and E434G;
H95Y, V122M and E434G;
H95Y, V179A, A369P, and E434G;
I75V and V76I;
I87L and A341D;
I87L and A369P;
I87L and A425T;
I 87L and D359A;
I87L and L479I;
I87L and L4I;
I87L and R319K;
I87L and V122M;
I87L, A341D, A369P, and E434G;
I87L, A341D, and R287H;
I87L, A369P, A425T, and E434G;
I87L, A369P, and E434G;
I87L, A369P, E434G, and R319K;
I87L, D359A, A369P, and E434G;
I87L, H95Y, A369P and E434G;
I87L, H95Y, and A369P;
I87L, H95Y, V122M, and E434G;
I87L, R287H, A369P, and E434G;
I87L, R287H, A369P, E434G, and A341D;
I87L, R57K, and R63K;
I87L, V122, A369P, and E434G;
I87L, V122M, and A369P;
I87L, V122M, and E434G;
I87L, V175A, and D359A;
L4I and V76I;
L4I, H95Y, A369P, and E434G;
L4I, I87L, A369P, and E434G;
L4I, V122M, A369P, and E434G;
R57K, I87L, A369P, and E434G;
R57K, R63K and H95Y;
R57K, R63K, I87L, A369P, and E434G;
R57K, R63K, V122M, A369P, and E434G;
R63K and I87L;
R63K and V122M;
R63K, A119S, and M499T;
R63K, I87L, A369P, and E434G;
R63K, I87V, and N194D;
R63K, V122M, A369P, and E434G;
R63K, V122M, R319K, and V40I;
V122M and A369P;
V122M and E434G;
V122M, A369P, A425T, and E434G;
V122M, A369P, and E434G;
V122M, A369P, E434G, and A341D;
V122M, A369P, E434G, and R319K;
V122M, A369P, E434G, and V175A;
V122M, D359A, A369P, and E434G;
V122M, R287H, A341D, A369P, and E434G;
V122M, R287H, A369P, and E434G;
V122M, V175A, D359A, A369P, and E434G;
V40A, R63K, and H89G;
V40I, H95Y, A369P, and E434G;
V74I and V76I;
V74I, I75V, and V76I;
V76I and A119S;
V76I and A369P;
V76I and V122M;
V76I, A369P, and E434G;
V76I, I87L, and K313R; and
V76I, V122M, and A369P.

* * * * *

SEQUENCE LISTING

```
Sequence total quantity: 372
SEQ ID NO: 1            moltype = AA  length = 500
FEATURE                 Location/Qualifiers
source                  1..500
                        mol_type = protein
                        note = Mycobacterium phage
                        organism = unidentified
SEQUENCE: 1
MRALVVIRLS RVTDATTSPE RQLESCQQLC AQRGWDVVGV AEDLDVSGAV DPFDRKRRPN   60
LARWLAFEEQ PFDVIVAYRV DRLTRSIRHL QQLVHWAEDH KKLVVSATEA HFDTTTPFAA  120
VVIALMGTVA QMELEAIKER NRSAAHFNIR AGKYRGSLPP WGYLPTRVDG EWRLVPDPVQ  180
RERILEVYHR VVDNHEPLHL VAHDLNRRGV LSPKDYFAQL QGREPQGREW SATALKRSMI  240
SEAMLGYATL NGKTVRDDDG APLVRAEPIL TREQLEALRA ELVKTSRAKP AVSTPSLLLR  300
VLFCAVCGEP AYKFAGGGRK HPRYRCRSMG FPKHCGNGTV AMAEWDAFCE EQVLDLLGDA  360
ERLEKVWVAG SDSAVELAEV NAELVDLTSL IGSPAYRAGS PQREALDARI AALAARQEEL  420
EGLEARPSGW EWRETGQRFG DWWREQDTAA KNTWLRSMNV RLTFDVRGGL TRTIDFGDLQ  480
EYEQHLRLGS VVERLHTGMS                                              500

SEQ ID NO: 2            moltype = AA  length = 605
FEATURE                 Location/Qualifiers
source                  1..605
                        mol_type = protein
                        note = Streptomyces phage C31
                        organism = unidentified
SEQUENCE: 2
MDTYAGAYDR QSRERENSSA ASPATQRSAN EDKAADLQRE VERDGGRFRF VGHFSEAPGT   60
SAFGTAERPE FERILNECRA GRLNMIIVYD VSRFSRLKVM DAIPIVSELL ALGVTIVSTQ  120
EGVFRQGNVM DLIHLIMRLD ASHKESSLKS AKILDTKNLQ RELGGYVGGK APYGFELVSE  180
TKEITRNGRM VNVVINKLAH STTPLTGPFE FEPDVIRWWW REIKTHKHLP FKPGSQAAIH  240
PGSITGLCKR MDADAVPTRG ETIGKKTASS AWDPATVMRI LRDPRIAGFA AEVIYKKKPD  300
GTPTTKIEGY RIQRDPITLR PVELDCGPII EPAEWYELQA WLDGRGRGKG LSRGQAILSA  360
MDKLYCECGA VMTSKRGEES IKDSYRCRRR KVVDPSAPGQ HEGTCNVSMA ALDKFVAERI  420
FNKIRHAEGD EETLALLWEA ARRFGKLTEA PEKSGERANL VAERADALNA LEELYEDRAA  480
GAYDGPVGRK HFRKQQAALT LRQQGAEERL AELEAAEAPK LPLDQWFPED ADAPTGPKS   540
WWGRASVDDK RVFVGLFVDK IVVTKSTTGR GQGTPIEKRA SITWAKPPTD DDEDDAQDGT  600
EDVAA                                                              605

SEQ ID NO: 3            moltype = AA  length = 8
FEATURE                 Location/Qualifiers
source                  1..8
                        mol_type = protein
                        organism = synthetic construct
SEQUENCE: 3
MIQGVVSG                                                             8

SEQ ID NO: 4            moltype = AA  length = 8
FEATURE                 Location/Qualifiers
source                  1..8
                        mol_type = protein
                        organism = synthetic construct
SEQUENCE: 4
```

-continued

```
MIQEVVSG                                                                    8

SEQ ID NO: 5              moltype = AA   length = 40
FEATURE                   Location/Qualifiers
source                    1..40
                          mol_type = protein
                          organism = synthetic construct
SEQUENCE: 5
MTMITPSAQL TLTKGNKSWS SLVTAASVLE FATMIQGVAG                                 40

SEQ ID NO: 6              moltype = AA   length = 41
FEATURE                   Location/Qualifiers
source                    1..41
                          mol_type = protein
                          organism = synthetic construct
SEQUENCE: 6
MTMIYPFPAQ LTLTKGNKSW SSLVTAASVL EFATMIQGVA G                               41

SEQ ID NO: 7              moltype = AA   length = 40
FEATURE                   Location/Qualifiers
source                    1..40
                          mol_type = protein
                          organism = synthetic construct
SEQUENCE: 7
MTMITPSAQL TLTKSNKSWN SLVTAASVLE FATMIQGVAG                                 40

SEQ ID NO: 8              moltype = AA   length = 40
FEATURE                   Location/Qualifiers
source                    1..40
                          mol_type = protein
                          organism = synthetic construct
SEQUENCE: 8
MTMITPSAQL TLTKGNKSWS SLVTAASVLE FATMIQGVAG                                 40

SEQ ID NO: 9              moltype = AA   length = 40
FEATURE                   Location/Qualifiers
source                    1..40
                          mol_type = protein
                          organism = synthetic construct
SEQUENCE: 9
MTMITPSAQL TLTKSNKSWS SLVTAASVLE FATMIQGVTG                                 40

SEQ ID NO: 10             moltype = AA   length = 40
FEATURE                   Location/Qualifiers
source                    1..40
                          mol_type = protein
                          organism = synthetic construct
SEQUENCE: 10
MTMITPSAQL TLTKDNKSWS SLVTAASVLE FATMIQGVAG                                 40

SEQ ID NO: 11             moltype = AA   length = 40
FEATURE                   Location/Qualifiers
source                    1..40
                          mol_type = protein
                          organism = synthetic construct
SEQUENCE: 11
MTMITPSAQL TLTKSNKSWS SLVTAASVLE FATMIQGVAG                                 40

SEQ ID NO: 12             moltype = AA   length = 40
FEATURE                   Location/Qualifiers
source                    1..40
                          mol_type = protein
                          organism = synthetic construct
SEQUENCE: 12
MTMITPSAQL TLTKSNKSWS SLVTAASVLE FATMIQGVAG                                 40

SEQ ID NO: 13             moltype = DNA  length = 38
FEATURE                   Location/Qualifiers
source                    1..38
                          mol_type = other DNA
                          organism = synthetic construct
SEQUENCE: 13
ggcttgtcga cgacggcggt ctccgtcgtc aggatcat                                   38

SEQ ID NO: 14             moltype = DNA  length = 48
FEATURE                   Location/Qualifiers
source                    1..48
                          mol_type = other DNA
                          organism = synthetic construct
```

```
SEQUENCE: 14
ggtttgtctg gtcaaccacc gcggtctcag tggtgtacgg tacaaacc              48

SEQ ID NO: 15           moltype = DNA   length = 35
FEATURE                 Location/Qualifiers
source                  1..35
                        mol_type = other DNA
                        organism = synthetic construct
SEQUENCE: 15
gtgccagggc gtgcccttgg gctccccggg cgcgt                            35

SEQ ID NO: 16           moltype = DNA   length = 42
FEATURE                 Location/Qualifiers
source                  1..42
                        mol_type = other DNA
                        organism = synthetic construct
SEQUENCE: 16
tgccccaact ggggtaacct ttgagttctc tcagttgggg gc                    42

SEQ ID NO: 17           moltype = DNA   length = 63
FEATURE                 Location/Qualifiers
source                  1..63
                        mol_type = other DNA
                        organism = synthetic construct
SEQUENCE: 17
tcgtcggcag cgtcagatgt gtataagaga caggatgacc taactgcttc tcctcttggg  60
aag                                                                63

SEQ ID NO: 18           moltype = DNA   length = 63
FEATURE                 Location/Qualifiers
source                  1..63
                        mol_type = other DNA
                        organism = synthetic construct
SEQUENCE: 18
tcgtcggcag cgtcagatgt gtataagaga cagctgtctg taactgcttc tcctcttggg  60
aag                                                                63

SEQ ID NO: 19           moltype = DNA   length = 63
FEATURE                 Location/Qualifiers
source                  1..63
                        mol_type = other DNA
                        organism = synthetic construct
SEQUENCE: 19
tcgtcggcag cgtcagatgt gtataagaga cagcacacag taactgcttc tcctcttggg  60
aag                                                                63

SEQ ID NO: 20           moltype = DNA   length = 63
FEATURE                 Location/Qualifiers
source                  1..63
                        mol_type = other DNA
                        organism = synthetic construct
SEQUENCE: 20
tcgtcggcag cgtcagatgt gtataagaga cagaaccggt taactgcttc tcctcttggg  60
aag                                                                63

SEQ ID NO: 21           moltype = DNA   length = 63
FEATURE                 Location/Qualifiers
source                  1..63
                        mol_type = other DNA
                        organism = synthetic construct
SEQUENCE: 21
tcgtcggcag cgtcagatgt gtataagaga cagtctctca gaactgcttc tcctcttggg  60
aag                                                                63

SEQ ID NO: 22           moltype = DNA   length = 63
FEATURE                 Location/Qualifiers
source                  1..63
                        mol_type = other DNA
                        organism = synthetic construct
SEQUENCE: 22
tcgtcggcag cgtcagatgt gtataagaga caggagtcac taactgcttc tcctcttggg  60
aag                                                                63

SEQ ID NO: 23           moltype = DNA   length = 63
FEATURE                 Location/Qualifiers
source                  1..63
                        mol_type = other DNA
                        organism = synthetic construct
SEQUENCE: 23
```

```
                                              -continued tcgtcggcag cgtcagatgt gtataagaga cagagactga gaactgcttc tcctcttggg    60
aag                                                                  63

SEQ ID NO: 24            moltype = DNA   length = 63
FEATURE                  Location/Qualifiers
source                   1..63
                         mol_type = other DNA
                         organism = synthetic construct
SEQUENCE: 24
tcgtcggcag cgtcagatgt gtataagaga cagggaatac gaactgcttc tcctcttggg    60
aag                                                                  63

SEQ ID NO: 25            moltype = DNA   length = 63
FEATURE                  Location/Qualifiers
source                   1..63
                         mol_type = other DNA
                         organism = synthetic construct
SEQUENCE: 25
tcgtcggcag cgtcagatgt gtataagaga cagagacctg taactgcttc tcctcttggg    60
aag                                                                  63

SEQ ID NO: 26            moltype = DNA   length = 63
FEATURE                  Location/Qualifiers
source                   1..63
                         mol_type = other DNA
                         organism = synthetic construct
SEQUENCE: 26
tcgtcggcag cgtcagatgt gtataagaga cagtaggcgt taactgcttc tcctcttggg    60
aag                                                                  63

SEQ ID NO: 27            moltype = DNA   length = 63
FEATURE                  Location/Qualifiers
source                   1..63
                         mol_type = other DNA
                         organism = synthetic construct
SEQUENCE: 27
tcgtcggcag cgtcagatgt gtataagaga cagtgacgac taactgcttc tcctcttggg    60
aag                                                                  63

SEQ ID NO: 28            moltype = DNA   length = 63
FEATURE                  Location/Qualifiers
source                   1..63
                         mol_type = other DNA
                         organism = synthetic construct
SEQUENCE: 28
tcgtcggcag cgtcagatgt gtataagaga cagagagact gaactgcttc tcctcttggg    60
aag                                                                  63

SEQ ID NO: 29            moltype = DNA   length = 63
FEATURE                  Location/Qualifiers
source                   1..63
                         mol_type = other DNA
                         organism = synthetic construct
SEQUENCE: 29
tcgtcggcag cgtcagatgt gtataagaga cagatatgcc gaactgcttc tcctcttggg    60
aag                                                                  63

SEQ ID NO: 30            moltype = DNA   length = 61
FEATURE                  Location/Qualifiers
source                   1..61
                         mol_type = other DNA
                         organism = synthetic construct
SEQUENCE: 30
tcgtcggcag cgtcagatgt gtataagaga cagcctacga acactaaggc aattggggtg    60
c                                                                    61

SEQ ID NO: 31            moltype = DNA   length = 61
FEATURE                  Location/Qualifiers
source                   1..61
                         mol_type = other DNA
                         organism = synthetic construct
SEQUENCE: 31
tcgtcggcag cgtcagatgt gtataagaga cagcgtagga acactaaggc aattggggtg    60
c                                                                    61

SEQ ID NO: 32            moltype = DNA   length = 56
FEATURE                  Location/Qualifiers
source                   1..56
                         mol_type = other DNA
```

```
                          organism = synthetic construct
SEQUENCE: 32
tcgtcggcag cgtcagatgt gtataagaga cagctctgac tgccaggacg gggctg        56

SEQ ID NO: 33            moltype = DNA   length = 56
FEATURE                  Location/Qualifiers
source                   1..56
                         mol_type = other DNA
                         organism = synthetic construct
SEQUENCE: 33
tcgtcggcag cgtcagatgt gtataagaga caggtcatca ggccaggacg gggctg        56

SEQ ID NO: 34            moltype = DNA   length = 74
FEATURE                  Location/Qualifiers
source                   1..74
                         mol_type = other DNA
                         organism = synthetic construct
SEQUENCE: 34
tcgtcggcag cgtcagatgt gtataagaga cagtcactct gaaggagaat gacagacaat    60
agtatatatg aaat                                                      74

SEQ ID NO: 35            moltype = DNA   length = 74
FEATURE                  Location/Qualifiers
source                   1..74
                         mol_type = other DNA
                         organism = synthetic construct
SEQUENCE: 35
tcgtcggcag cgtcagatgt gtataagaga cagctgacag taaggagaat gacagacaat    60
agtatatatg aaat                                                      74

SEQ ID NO: 36            moltype = DNA   length = 74
FEATURE                  Location/Qualifiers
source                   1..74
                         mol_type = other DNA
                         organism = synthetic construct
SEQUENCE: 36
tcgtcggcag cgtcagatgt gtataagaga cagagtgaca gaaggagaat gacagacaat    60
agtatatatg aaat                                                      74

SEQ ID NO: 37            moltype = DNA   length = 74
FEATURE                  Location/Qualifiers
source                   1..74
                         mol_type = other DNA
                         organism = synthetic construct
SEQUENCE: 37
tcgtcggcag cgtcagatgt gtataagaga cagacctacc taaggagaat gacagacaat    60
agtatatatg aaat                                                      74

SEQ ID NO: 38            moltype = DNA   length = 74
FEATURE                  Location/Qualifiers
source                   1..74
                         mol_type = other DNA
                         organism = synthetic construct
SEQUENCE: 38
tcgtcggcag cgtcagatgt gtataagaga cagcatgtgg taaggagaat gacagacaat    60
agtatatatg aaat                                                      74

SEQ ID NO: 39            moltype = DNA   length = 74
FEATURE                  Location/Qualifiers
source                   1..74
                         mol_type = other DNA
                         organism = synthetic construct
SEQUENCE: 39
tcgtcggcag cgtcagatgt gtataagaga cagttcgtag gaaggagaat gacagacaat    60
agtatatatg aaat                                                      74

SEQ ID NO: 40            moltype = DNA   length = 74
FEATURE                  Location/Qualifiers
source                   1..74
                         mol_type = other DNA
                         organism = synthetic construct
SEQUENCE: 40
tcgtcggcag cgtcagatgt gtataagaga caggtcttga gaaggagaat gacagacaat    60
agtatatatg aaat                                                      74

SEQ ID NO: 41            moltype = DNA   length = 74
FEATURE                  Location/Qualifiers
source                   1..74
                         mol_type = other DNA
```

```
                organism = synthetic construct
SEQUENCE: 41
tcgtcggcag cgtcagatgt gtataagaga cagacagagt gaaggagaat gacagacaat    60
agtatatatg aaat                                                      74

SEQ ID NO: 42           moltype = DNA   length = 65
FEATURE                 Location/Qualifiers
source                  1..65
                        mol_type = other DNA
                        organism = synthetic construct
SEQUENCE: 42
tcgtcggcag cgtcagatgt gtataagaga cagttcgaac ggtgaatgac taagctccat    60
ttccc                                                                65

SEQ ID NO: 43           moltype = DNA   length = 65
FEATURE                 Location/Qualifiers
source                  1..65
                        mol_type = other DNA
                        organism = synthetic construct
SEQUENCE: 43
tcgtcggcag cgtcagatgt gtataagaga caggatgagg tgtgaatgac taagctccat    60
ttccc                                                                65

SEQ ID NO: 44           moltype = DNA   length = 65
FEATURE                 Location/Qualifiers
source                  1..65
                        mol_type = other DNA
                        organism = synthetic construct
SEQUENCE: 44
tcgtcggcag cgtcagatgt gtataagaga cagcctacgt tgtgaatgac taagctccat    60
ttccc                                                                65

SEQ ID NO: 45           moltype = DNA   length = 65
FEATURE                 Location/Qualifiers
source                  1..65
                        mol_type = other DNA
                        organism = synthetic construct
SEQUENCE: 45
tcgtcggcag cgtcagatgt gtataagaga caggagttga ggtgaatgac taagctccat    60
ttccc                                                                65

SEQ ID NO: 46           moltype = DNA   length = 59
FEATURE                 Location/Qualifiers
source                  1..59
                        mol_type = other DNA
                        organism = synthetic construct
SEQUENCE: 46
tcgtcggcag cgtcagatgt gtataagaga cagttcgaac gctccatttc cctacccca    59

SEQ ID NO: 47           moltype = DNA   length = 59
FEATURE                 Location/Qualifiers
source                  1..59
                        mol_type = other DNA
                        organism = synthetic construct
SEQUENCE: 47
tcgtcggcag cgtcagatgt gtataagaga caggatgagg tctccatttc cctacccca    59

SEQ ID NO: 48           moltype = DNA   length = 59
FEATURE                 Location/Qualifiers
source                  1..59
                        mol_type = other DNA
                        organism = synthetic construct
SEQUENCE: 48
tcgtcggcag cgtcagatgt gtataagaga cagcctacgt tctccatttc cctacccca    59

SEQ ID NO: 49           moltype = DNA   length = 59
FEATURE                 Location/Qualifiers
source                  1..59
                        mol_type = other DNA
                        organism = synthetic construct
SEQUENCE: 49
tcgtcggcag cgtcagatgt gtataagaga caggagttga gctccatttc cctacccca    59

SEQ ID NO: 50           moltype = DNA   length = 60
FEATURE                 Location/Qualifiers
source                  1..60
                        mol_type = other DNA
                        organism = synthetic construct
SEQUENCE: 50
```

```
tcgtcggcag cgtcagatgt gtataagaga cagggttcga tgggagggaa gcactggttt    60

SEQ ID NO: 51              moltype = DNA   length = 60
FEATURE                    Location/Qualifiers
source                     1..60
                           mol_type = other DNA
                           organism = synthetic construct SEQUENCE: 51
tcgtcggcag cgtcagatgt gtataagaga cagatcgttg ggggagggaa gcactggttt    60

SEQ ID NO: 52              moltype = DNA   length = 64
FEATURE                    Location/Qualifiers
source                     1..64
                           mol_type = other DNA
                           organism = synthetic construct SEQUENCE: 52
tcgtcggcag cgtcagatgt gtataagaga cagagactct ggagagggag aaagctagtg    60
ctat                                                                 64

SEQ ID NO: 53              moltype = DNA   length = 64
FEATURE                    Location/Qualifiers
source                     1..64
                           mol_type = other DNA
                           organism = synthetic construct SEQUENCE: 53
tcgtcggcag cgtcagatgt gtataagaga cagcagtact ggagagggag aaagctagtg    60
ctat                                                                 64

SEQ ID NO: 54              moltype = DNA   length = 60
FEATURE                    Location/Qualifiers
source                     1..60
                           mol_type = other DNA
                           organism = synthetic construct SEQUENCE: 54
gtctcgtggg ctcggagatg tgtataagag acagcatcca agcccccatt tcctggagcc    60

SEQ ID NO: 55              moltype = DNA   length = 60
FEATURE                    Location/Qualifiers
source                     1..60
                           mol_type = other DNA
                           organism = synthetic construct SEQUENCE: 55
gtctcgtggg ctcggagatg tgtataagag acagcgttgg atcccccatt tcctggagcc    60

SEQ ID NO: 56              moltype = DNA   length = 60
FEATURE                    Location/Qualifiers
source                     1..60
                           mol_type = other DNA
                           organism = synthetic construct SEQUENCE: 56
gtctcgtggg ctcggagatg tgtataagag acaggatctg gtcccccatt tcctggagcc    60

SEQ ID NO: 57              moltype = DNA   length = 60
FEATURE                    Location/Qualifiers
source                     1..60
                           mol_type = other DNA
                           organism = synthetic construct SEQUENCE: 57
gtctcgtggg ctcggagatg tgtataagag acaggttcct tgcccccatt tcctggagcc    60

SEQ ID NO: 58              moltype = DNA   length = 60
FEATURE                    Location/Qualifiers
source                     1..60
                           mol_type = other DNA
                           organism = synthetic construct SEQUENCE: 58
gtctcgtggg ctcggagatg tgtataagag acagctagtg gtcccccatt tcctggagcc    60

SEQ ID NO: 59              moltype = DNA   length = 60
FEATURE                    Location/Qualifiers
source                     1..60
                           mol_type = other DNA
                           organism = synthetic construct SEQUENCE: 59
gtctcgtggg ctcggagatg tgtataagag acagcagtca gtcccccatt tcctggagcc    60

SEQ ID NO: 60              moltype = DNA   length = 60
FEATURE                    Location/Qualifiers
source                     1..60
```

```
                              mol_type = other DNA
                              organism = synthetic construct
SEQUENCE: 60
gtctcgtggg ctcggagatg tgtataagag acaggtgtac tgcccccatt tcctggagcc   60

SEQ ID NO: 61                 moltype = DNA  length = 60
FEATURE                       Location/Qualifiers
source                        1..60
                              mol_type = other DNA
                              organism = synthetic construct
SEQUENCE: 61
gtctcgtggg ctcggagatg tgtataagag acaggttgtc ctcccccatt tcctggagcc   60

SEQ ID NO: 62                 moltype = DNA  length = 60
FEATURE                       Location/Qualifiers
source                        1..60
                              mol_type = other DNA
                              organism = synthetic construct
SEQUENCE: 62
gtctcgtggg ctcggagatg tgtataagag acagaccatg gtcccccatt tcctggagcc   60

SEQ ID NO: 63                 moltype = DNA  length = 60
FEATURE                       Location/Qualifiers
source                        1..60
                              mol_type = other DNA
                              organism = synthetic construct
SEQUENCE: 63
gtctcgtggg ctcggagatg tgtataagag acagcacaac tgcccccatt tcctggagcc   60

SEQ ID NO: 64                 moltype = DNA  length = 63
FEATURE                       Location/Qualifiers
source                        1..63
                              mol_type = other DNA
                              organism = synthetic construct
SEQUENCE: 64
tcgtcggcag cgtcagatgt gtataagaga caggatgacc taactgcttc tcctcttggg   60
aag                                                                 63

SEQ ID NO: 65                 moltype = DNA  length = 63
FEATURE                       Location/Qualifiers
source                        1..63
                              mol_type = other DNA
                              organism = synthetic construct
SEQUENCE: 65
tcgtcggcag cgtcagatgt gtataagaga cagctgtctg taactgcttc tcctcttggg   60
aag                                                                 63

SEQ ID NO: 66                 moltype = DNA  length = 63
FEATURE                       Location/Qualifiers
source                        1..63
                              mol_type = other DNA
                              organism = synthetic construct
SEQUENCE: 66
tcgtcggcag cgtcagatgt gtataagaga cagcacacag taactgcttc tcctcttggg   60
aag                                                                 63

SEQ ID NO: 67                 moltype = DNA  length = 63
FEATURE                       Location/Qualifiers
source                        1..63
                              mol_type = other DNA
                              organism = synthetic construct
SEQUENCE: 67
tcgtcggcag cgtcagatgt gtataagaga cagaaccggt taactgcttc tcctcttggg   60
aag                                                                 63

SEQ ID NO: 68                 moltype = DNA  length = 63
FEATURE                       Location/Qualifiers
source                        1..63
                              mol_type = other DNA
                              organism = synthetic construct
SEQUENCE: 68
tcgtcggcag cgtcagatgt gtataagaga cagtctctca gaactgcttc tcctcttggg   60
aag                                                                 63

SEQ ID NO: 69                 moltype = DNA  length = 63
FEATURE                       Location/Qualifiers
source                        1..63
                              mol_type = other DNA
                              organism = synthetic construct
```

```
SEQUENCE: 69
tcgtcggcag cgtcagatgt gtataagaga caggagtcac taactgcttc tcctcttggg    60
aag                                                                  63

SEQ ID NO: 70          moltype = DNA   length = 63
FEATURE                Location/Qualifiers
source                 1..63
                       mol_type = other DNA
                       organism = synthetic construct
SEQUENCE: 70
tcgtcggcag cgtcagatgt gtataagaga cagagactga gaactgcttc tcctcttggg    60
aag                                                                  63

SEQ ID NO: 71          moltype = DNA   length = 63
FEATURE                Location/Qualifiers
source                 1..63
                       mol_type = other DNA
                       organism = synthetic construct
SEQUENCE: 71
tcgtcggcag cgtcagatgt gtataagaga cagggaatac gaactgcttc tcctcttggg    60
aag                                                                  63

SEQ ID NO: 72          moltype = DNA   length = 63
FEATURE                Location/Qualifiers
source                 1..63
                       mol_type = other DNA
                       organism = synthetic construct
SEQUENCE: 72
tcgtcggcag cgtcagatgt gtataagaga cagagacctg taactgcttc tcctcttggg    60
aag                                                                  63

SEQ ID NO: 73          moltype = DNA   length = 63
FEATURE                Location/Qualifiers
source                 1..63
                       mol_type = other DNA
                       organism = synthetic construct
SEQUENCE: 73
tcgtcggcag cgtcagatgt gtataagaga cagtaggcgt taactgcttc tcctcttggg    60
aag                                                                  63

SEQ ID NO: 74          moltype = DNA   length = 63
FEATURE                Location/Qualifiers
source                 1..63
                       mol_type = other DNA
                       organism = synthetic construct
SEQUENCE: 74
tcgtcggcag cgtcagatgt gtataagaga cagtgacgac taactgcttc tcctcttggg    60
aag                                                                  63

SEQ ID NO: 75          moltype = DNA   length = 63
FEATURE                Location/Qualifiers
source                 1..63
                       mol_type = other DNA
                       organism = synthetic construct
SEQUENCE: 75
tcgtcggcag cgtcagatgt gtataagaga cagagagact gaactgcttc tcctcttggg    60
aag                                                                  63

SEQ ID NO: 76          moltype = DNA   length = 63
FEATURE                Location/Qualifiers
source                 1..63
                       mol_type = other DNA
                       organism = synthetic construct
SEQUENCE: 76
tcgtcggcag cgtcagatgt gtataagaga cagatatgcc gaactgcttc tcctcttggg    60
aag                                                                  63

SEQ ID NO: 77          moltype = DNA   length = 61
FEATURE                Location/Qualifiers
source                 1..61
                       mol_type = other DNA
                       organism = synthetic construct
SEQUENCE: 77
tcgtcggcag cgtcagatgt gtataagaga cagcctacga acactaaggc aattggggtg    60
c                                                                    61

SEQ ID NO: 78          moltype = DNA   length = 61
FEATURE                Location/Qualifiers
source                 1..61
```

```
                        mol_type = other DNA
                        organism = synthetic construct
SEQUENCE: 78
tcgtcggcag cgtcagatgt gtataagaga cagcgtagga acactaaggc aattggggtg    60
c                                                                    61

SEQ ID NO: 79           moltype = DNA   length = 56
FEATURE                 Location/Qualifiers
source                  1..56
                        mol_type = other DNA
                        organism = synthetic construct
SEQUENCE: 79
tcgtcggcag cgtcagatgt gtataagaga cagctctgac tgccaggacg gggctg        56

SEQ ID NO: 80           moltype = DNA   length = 56
FEATURE                 Location/Qualifiers
source                  1..56
                        mol_type = other DNA
                        organism = synthetic construct
SEQUENCE: 80
tcgtcggcag cgtcagatgt gtataagaga caggtcatca ggccaggacg gggctg        56

SEQ ID NO: 81           moltype = DNA   length = 74
FEATURE                 Location/Qualifiers
source                  1..74
                        mol_type = other DNA
                        organism = synthetic construct
SEQUENCE: 81
tcgtcggcag cgtcagatgt gtataagaga cagtcactct gaaggagaat gacagacaat    60
agtatatatg aaat                                                      74

SEQ ID NO: 82           moltype = DNA   length = 74
FEATURE                 Location/Qualifiers
source                  1..74
                        mol_type = other DNA
                        organism = synthetic construct
SEQUENCE: 82
tcgtcggcag cgtcagatgt gtataagaga cagctgacag taaggagaat gacagacaat    60
agtatatatg aaat                                                      74

SEQ ID NO: 83           moltype = DNA   length = 74
FEATURE                 Location/Qualifiers
source                  1..74
                        mol_type = other DNA
                        organism = synthetic construct
SEQUENCE: 83
tcgtcggcag cgtcagatgt gtataagaga cagagtgaca gaaggagaat gacagacaat    60
agtatatatg aaat                                                      74

SEQ ID NO: 84           moltype = DNA   length = 74
FEATURE                 Location/Qualifiers
source                  1..74
                        mol_type = other DNA
                        organism = synthetic construct
SEQUENCE: 84
tcgtcggcag cgtcagatgt gtataagaga cagacctacc taaggagaat gacagacaat    60
agtatatatg aaat                                                      74

SEQ ID NO: 85           moltype = DNA   length = 74
FEATURE                 Location/Qualifiers
source                  1..74
                        mol_type = other DNA
                        organism = synthetic construct
SEQUENCE: 85
tcgtcggcag cgtcagatgt gtataagaga cagcatgtgg taaggagaat gacagacaat    60
agtatatatg aaat                                                      74

SEQ ID NO: 86           moltype = DNA   length = 74
FEATURE                 Location/Qualifiers
source                  1..74
                        mol_type = other DNA
                        organism = synthetic construct
SEQUENCE: 86
tcgtcggcag cgtcagatgt gtataagaga cagttcgtag gaaggagaat gacagacaat    60
agtatatatg aaat                                                      74

SEQ ID NO: 87           moltype = DNA   length = 74
FEATURE                 Location/Qualifiers
source                  1..74
```

```
                              mol_type = other DNA
                              organism = synthetic construct
SEQUENCE: 87
tcgtcggcag cgtcagatgt gtataagaga caggtcttga gaaggagaat gacagacaat    60
agtatatatg aaat                                                      74

SEQ ID NO: 88             moltype = DNA   length = 74
FEATURE                   Location/Qualifiers
source                    1..74
                          mol_type = other DNA
                          organism = synthetic construct
SEQUENCE: 88
tcgtcggcag cgtcagatgt gtataagaga cagacagagt gaaggagaat gacagacaat    60
agtatatatg aaat                                                      74

SEQ ID NO: 89             moltype = DNA   length = 65
FEATURE                   Location/Qualifiers
source                    1..65
                          mol_type = other DNA
                          organism = synthetic construct
SEQUENCE: 89
tcgtcggcag cgtcagatgt gtataagaga cagttcgaac ggtgaatgac taagctccat    60
ttccc                                                                65

SEQ ID NO: 90             moltype = DNA   length = 65
FEATURE                   Location/Qualifiers
source                    1..65
                          mol_type = other DNA
                          organism = synthetic construct
SEQUENCE: 90
tcgtcggcag cgtcagatgt gtataagaga caggatgagg tgtgaatgac taagctccat    60
ttccc                                                                65

SEQ ID NO: 91             moltype = DNA   length = 65
FEATURE                   Location/Qualifiers
source                    1..65
                          mol_type = other DNA
                          organism = synthetic construct
SEQUENCE: 91
tcgtcggcag cgtcagatgt gtataagaga cagcctacgt tgtgaatgac taagctccat    60
ttccc                                                                65

SEQ ID NO: 92             moltype = DNA   length = 65
FEATURE                   Location/Qualifiers
source                    1..65
                          mol_type = other DNA
                          organism = synthetic construct
SEQUENCE: 92
tcgtcggcag cgtcagatgt gtataagaga caggagttga ggtgaatgac taagctccat    60
ttccc                                                                65

SEQ ID NO: 93             moltype = DNA   length = 59
FEATURE                   Location/Qualifiers
source                    1..59
                          mol_type = other DNA
                          organism = synthetic construct
SEQUENCE: 93
tcgtcggcag cgtcagatgt gtataagaga cagttcgaac gctccatttc cctacccca     59

SEQ ID NO: 94             moltype = DNA   length = 59
FEATURE                   Location/Qualifiers
source                    1..59
                          mol_type = other DNA
                          organism = synthetic construct
SEQUENCE: 94
tcgtcggcag cgtcagatgt gtataagaga caggatgagg tctccatttc cctacccca     59

SEQ ID NO: 95             moltype = DNA   length = 59
FEATURE                   Location/Qualifiers
source                    1..59
                          mol_type = other DNA
                          organism = synthetic construct
SEQUENCE: 95
tcgtcggcag cgtcagatgt gtataagaga cagcctacgt tctccatttc cctacccca     59

SEQ ID NO: 96             moltype = DNA   length = 59
FEATURE                   Location/Qualifiers
source                    1..59
                          mol_type = other DNA
```

```
                        organism = synthetic construct
SEQUENCE: 96
tcgtcggcag cgtcagatgt gtataagaga caggagttga gctccatttc cctacccca     59

SEQ ID NO: 97           moltype = DNA   length = 60
FEATURE                 Location/Qualifiers
source                  1..60
                        mol_type = other DNA
                        organism = synthetic construct
SEQUENCE: 97
tcgtcggcag cgtcagatgt gtataagaga cagggttcga tgggagggaa gcactggttt     60

SEQ ID NO: 98           moltype = DNA   length = 60
FEATURE                 Location/Qualifiers
source                  1..60
                        mol_type = other DNA
                        organism = synthetic construct
SEQUENCE: 98
tcgtcggcag cgtcagatgt gtataagaga cagatcgttg ggggagggaa gcactggttt     60

SEQ ID NO: 99           moltype = DNA   length = 64
FEATURE                 Location/Qualifiers
source                  1..64
                        mol_type = other DNA
                        organism = synthetic construct
SEQUENCE: 99
tcgtcggcag cgtcagatgt gtataagaga cagagactct ggagagggag aaagctagtg     60
ctat                                                                  64

SEQ ID NO: 100          moltype = DNA   length = 64
FEATURE                 Location/Qualifiers
source                  1..64
                        mol_type = other DNA
                        organism = synthetic construct
SEQUENCE: 100
tcgtcggcag cgtcagatgt gtataagaga cagcagtact ggagagggag aaagctagtg     60
ctat                                                                  64

SEQ ID NO: 101          moltype = DNA   length = 60
FEATURE                 Location/Qualifiers
source                  1..60
                        mol_type = other DNA
                        organism = synthetic construct
SEQUENCE: 101
gtctcgtggg ctcggagatg tgtataagag acagcatcca agcccccatt tcctggagcc     60

SEQ ID NO: 102          moltype = DNA   length = 60
FEATURE                 Location/Qualifiers
source                  1..60
                        mol_type = other DNA
                        organism = synthetic construct
SEQUENCE: 102
gtctcgtggg ctcggagatg tgtataagag acagcgttgg atcccccatt tcctggagcc     60

SEQ ID NO: 103          moltype = DNA   length = 60
FEATURE                 Location/Qualifiers
source                  1..60
                        mol_type = other DNA
                        organism = synthetic construct
SEQUENCE: 103
gtctcgtggg ctcggagatg tgtataagag acaggatctg gtcccccatt tcctggagcc     60

SEQ ID NO: 104          moltype = DNA   length = 60
FEATURE                 Location/Qualifiers
source                  1..60
                        mol_type = other DNA
                        organism = synthetic construct
SEQUENCE: 104
gtctcgtggg ctcggagatg tgtataagag acaggttcct tgcccccatt tcctggagcc     60

SEQ ID NO: 105          moltype = DNA   length = 60
FEATURE                 Location/Qualifiers
source                  1..60
                        mol_type = other DNA
                        organism = synthetic construct
SEQUENCE: 105
gtctcgtggg ctcggagatg tgtataagag acagctagtg gtcccccatt tcctggagcc     60

SEQ ID NO: 106          moltype = DNA   length = 60
```

```
FEATURE              Location/Qualifiers
source               1..60
                     mol_type = other DNA
                     organism = synthetic construct
SEQUENCE: 106
gtctcgtggg ctcggagatg tgtataagag acagcagtca gtcccccatt tcctggagcc   60

SEQ ID NO: 107       moltype = DNA  length = 60
FEATURE              Location/Qualifiers
source               1..60
                     mol_type = other DNA
                     organism = synthetic construct
SEQUENCE: 107
gtctcgtggg ctcggagatg tgtataagag acaggtgtac tgcccccatt tcctggagcc   60

SEQ ID NO: 108       moltype = DNA  length = 60
FEATURE              Location/Qualifiers
source               1..60
                     mol_type = other DNA
                     organism = synthetic construct
SEQUENCE: 108
gtctcgtggg ctcggagatg tgtataagag acaggttgtc ctcccccatt tcctggagcc   60

SEQ ID NO: 109       moltype = DNA  length = 60
FEATURE              Location/Qualifiers
source               1..60
                     mol_type = other DNA
                     organism = synthetic construct
SEQUENCE: 109
gtctcgtggg ctcggagatg tgtataagag acagaccatg gtcccccatt tcctggagcc   60

SEQ ID NO: 110       moltype = DNA  length = 60
FEATURE              Location/Qualifiers
source               1..60
                     mol_type = other DNA
                     organism = synthetic construct
SEQUENCE: 110
gtctcgtggg ctcggagatg tgtataagag acagcacaac tgcccccatt tcctggagcc   60

SEQ ID NO: 111       moltype = DNA  length = 60
FEATURE              Location/Qualifiers
source               1..60
                     mol_type = other DNA
                     organism = synthetic construct
SEQUENCE: 111
gtctcgtggg ctcggagatg tgtataagag acagctctct ctcccccatt tcctggagcc   60

SEQ ID NO: 112       moltype = DNA  length = 60
FEATURE              Location/Qualifiers
source               1..60
                     mol_type = other DNA
                     organism = synthetic construct
SEQUENCE: 112
gtctcgtggg ctcggagatg tgtataagag acagtaggaa cgcccccatt tcctggagcc   60

SEQ ID NO: 113       moltype = DNA  length = 60
FEATURE              Location/Qualifiers
source               1..60
                     mol_type = other DNA
                     organism = synthetic construct
SEQUENCE: 113
gtctcgtggg ctcggagatg tgtataagag acagtctcca gtcccccatt tcctggagcc   60

SEQ ID NO: 114       moltype = DNA  length = 65
FEATURE              Location/Qualifiers
source               1..65
                     mol_type = other DNA
                     organism = synthetic construct
SEQUENCE: 114
gtctcgtggg ctcggagatg tgtataagag acagagtcga ctgcctagtt ttagcactga   60
aaccc                                                               65

SEQ ID NO: 115       moltype = DNA  length = 65
FEATURE              Location/Qualifiers
source               1..65
                     mol_type = other DNA
                     organism = synthetic construct
SEQUENCE: 115
gtctcgtggg ctcggagatg tgtataagag acagaacgta gggcctagtt ttagcactga   60
```

```
aaccc                                                              65

SEQ ID NO: 116          moltype = DNA   length = 58
FEATURE                 Location/Qualifiers
source                  1..58
                        mol_type = other DNA
                        organism = synthetic construct
SEQUENCE: 116
gtctcgtggg ctcggagatg tgtataagag acagactgga ctggccaccc tgcgctac    58

SEQ ID NO: 117          moltype = DNA   length = 58
FEATURE                 Location/Qualifiers
source                  1..58
                        mol_type = other DNA
                        organism = synthetic construct
SEQUENCE: 117
gtctcgtggg ctcggagatg tgtataagag acagactcac agggccaccc tgcgctac    58

SEQ ID NO: 118          moltype = DNA   length = 68
FEATURE                 Location/Qualifiers
source                  1..68
                        mol_type = other DNA
                        organism = synthetic construct
SEQUENCE: 118
gtctcgtggg ctcggagatg tgtataagag acagctacgt agcccaggtt acatttggtt  60
gatatgtc                                                           68

SEQ ID NO: 119          moltype = DNA   length = 68
FEATURE                 Location/Qualifiers
source                  1..68
                        mol_type = other DNA
                        organism = synthetic construct
SEQUENCE: 119
gtctcgtggg ctcggagatg tgtataagag acagttccgg ttcccaggtt acatttggtt  60
gatatgtc                                                           68

SEQ ID NO: 120          moltype = DNA   length = 66
FEATURE                 Location/Qualifiers
source                  1..66
                        mol_type = other DNA
                        organism = synthetic construct
SEQUENCE: 120
gtctcgtggg ctcggagatg tgtataagag acaggacatg agcaggtatt ttaaatggtc  60
cccagg                                                             66

SEQ ID NO: 121          moltype = DNA   length = 66
FEATURE                 Location/Qualifiers
source                  1..66
                        mol_type = other DNA
                        organism = synthetic construct
SEQUENCE: 121
gtctcgtggg ctcggagatg tgtataagag acagcaacca tgcaggtatt ttaaatggtc  60
cccagg                                                             66

SEQ ID NO: 122          moltype = DNA   length = 66
FEATURE                 Location/Qualifiers
source                  1..66
                        mol_type = other DNA
                        organism = synthetic construct
SEQUENCE: 122
gtctcgtggg ctcggagatg tgtataagag acagacacct ctcaggtatt ttaaatggtc  60
cccagg                                                             66

SEQ ID NO: 123          moltype = DNA   length = 66
FEATURE                 Location/Qualifiers
source                  1..66
                        mol_type = other DNA
                        organism = synthetic construct
SEQUENCE: 123
gtctcgtggg ctcggagatg tgtataagag acagctcaac agcaggtatt ttaaatggtc  60
cccagg                                                             66

SEQ ID NO: 124          moltype = DNA   length = 66
FEATURE                 Location/Qualifiers
source                  1..66
                        mol_type = other DNA
                        organism = synthetic construct
SEQUENCE: 124
gtctcgtggg ctcggagatg tgtataagag acagacgttg gtcaggtatt ttaaatggtc  60
```

```
cccagg                                                                      66

SEQ ID NO: 125           moltype = DNA   length = 66
FEATURE                  Location/Qualifiers
source                   1..66
                         mol_type = other DNA
                         organism = synthetic construct
SEQUENCE: 125
gtctcgtggg ctcggagatg tgtataagag acagaacgat ggcaggtatt ttaaatggtc    60
cccagg                                                               66

SEQ ID NO: 126           moltype = DNA   length = 64
FEATURE                  Location/Qualifiers
source                   1..64
                         mol_type = other DNA
                         organism = synthetic construct
SEQUENCE: 126
gtctcgtggg ctcggagatg tgtataagag acagactgtg tgagaagagg tcagaaagcc    60
agtc                                                                 64

SEQ ID NO: 127           moltype = DNA   length = 64
FEATURE                  Location/Qualifiers
source                   1..64
                         mol_type = other DNA
                         organism = synthetic construct
SEQUENCE: 127
gtctcgtggg ctcggagatg tgtataagag acagtggtga agagaagagg tcagaaagcc    60
agtc                                                                 64

SEQ ID NO: 128           moltype = DNA   length = 64
FEATURE                  Location/Qualifiers
source                   1..64
                         mol_type = other DNA
                         organism = synthetic construct
SEQUENCE: 128
gtctcgtggg ctcggagatg tgtataagag acagcttctc ctagaagagg tcagaaagcc    60
agtc                                                                 64

SEQ ID NO: 129           moltype = DNA   length = 64
FEATURE                  Location/Qualifiers
source                   1..64
                         mol_type = other DNA
                         organism = synthetic construct
SEQUENCE: 129
gtctcgtggg ctcggagatg tgtataagag acaggagtgt ctagaagagg tcagaaagcc    60
agtc                                                                 64

SEQ ID NO: 130           moltype = DNA   length = 60
FEATURE                  Location/Qualifiers
source                   1..60
                         mol_type = other DNA
                         organism = synthetic construct
SEQUENCE: 130
gtctcgtggg ctcggagatg tgtataagag acagactgtg tggtcagaaa gccagtcgcg    60

SEQ ID NO: 131           moltype = DNA   length = 60
FEATURE                  Location/Qualifiers
source                   1..60
                         mol_type = other DNA
                         organism = synthetic construct
SEQUENCE: 131
gtctcgtggg ctcggagatg tgtataagag acagtggtga aggtcagaaa gccagtcgcg    60

SEQ ID NO: 132           moltype = DNA   length = 60
FEATURE                  Location/Qualifiers
source                   1..60
                         mol_type = other DNA
                         organism = synthetic construct
SEQUENCE: 132
gtctcgtggg ctcggagatg tgtataagag acagcttctc ctgtcagaaa gccagtcgcg    60

SEQ ID NO: 133           moltype = DNA   length = 60
FEATURE                  Location/Qualifiers
source                   1..60
                         mol_type = other DNA
                         organism = synthetic construct
SEQUENCE: 133
gtctcgtggg ctcggagatg tgtataagag acaggagtgt ctgtcagaaa gccagtcgcg    60
```

```
SEQ ID NO: 134           moltype = DNA  length = 68
FEATURE                  Location/Qualifiers
source                   1..68
                         mol_type = other DNA
                         organism = synthetic construct
SEQUENCE: 134
gtctcgtggg ctcggagatg tgtataagag acagtctcag agggttattg taataagggt    60
ggggtagg                                                             68

SEQ ID NO: 135           moltype = DNA  length = 68
FEATURE                  Location/Qualifiers
source                   1..68
                         mol_type = other DNA
                         organism = synthetic construct
SEQUENCE: 135
gtctcgtggg ctcggagatg tgtataagag acagcagttc agggttattg taataagggt    60
ggggtagg                                                             68

SEQ ID NO: 136           moltype = DNA  length = 68
FEATURE                  Location/Qualifiers
source                   1..68
                         mol_type = other DNA
                         organism = synthetic construct
SEQUENCE: 136
gtctcgtggg ctcggagatg tgtataagag acagagtgca ctcctgagtt ttataccatt    60
tgagaccc                                                             68

SEQ ID NO: 137           moltype = DNA  length = 68
FEATURE                  Location/Qualifiers
source                   1..68
                         mol_type = other DNA
                         organism = synthetic construct
SEQUENCE: 137
gtctcgtggg ctcggagatg tgtataagag acagacctag gtcctgagtt ttataccatt    60
tgagaccc                                                             68

SEQ ID NO: 138           moltype = DNA  length = 65
FEATURE                  Location/Qualifiers
source                   1..65
                         mol_type = other DNA
                         organism = synthetic construct
SEQUENCE: 138
tcgtcggcag cgtcagatgt gtataagaga cagttcgaac ggtgaatgac taagctccat    60
ttccc                                                                65

SEQ ID NO: 139           moltype = DNA  length = 65
FEATURE                  Location/Qualifiers
source                   1..65
                         mol_type = other DNA
                         organism = synthetic construct
SEQUENCE: 139
tcgtcggcag cgtcagatgt gtataagaga caggatgagg tgtgaatgac taagctccat    60
ttccc                                                                65

SEQ ID NO: 140           moltype = DNA  length = 65
FEATURE                  Location/Qualifiers
source                   1..65
                         mol_type = other DNA
                         organism = synthetic construct
SEQUENCE: 140
tcgtcggcag cgtcagatgt gtataagaga cagcctacgt tgtgaatgac taagctccat    60
ttccc                                                                65

SEQ ID NO: 141           moltype = DNA  length = 65
FEATURE                  Location/Qualifiers
source                   1..65
                         mol_type = other DNA
                         organism = synthetic construct
SEQUENCE: 141
tcgtcggcag cgtcagatgt gtataagaga caggagttga ggtgaatgac taagctccat    60
ttccc                                                                65

SEQ ID NO: 142           moltype = DNA  length = 59
FEATURE                  Location/Qualifiers
source                   1..59
                         mol_type = other DNA
                         organism = synthetic construct
SEQUENCE: 142
tcgtcggcag cgtcagatgt gtataagaga cagttcgaac gctccatttc cctacccca    59
```

```
SEQ ID NO: 143          moltype = DNA  length = 59
FEATURE                 Location/Qualifiers
source                  1..59
                        mol_type = other DNA
                        organism = synthetic construct
SEQUENCE: 143
tcgtcggcag cgtcagatgt gtataagaga caggatgagg tctccatttc cctacccca      59

SEQ ID NO: 144          moltype = DNA  length = 59
FEATURE                 Location/Qualifiers
source                  1..59
                        mol_type = other DNA
                        organism = synthetic construct
SEQUENCE: 144
tcgtcggcag cgtcagatgt gtataagaga cagcctacgt tctccatttc cctacccca      59

SEQ ID NO: 145          moltype = DNA  length = 59
FEATURE                 Location/Qualifiers
source                  1..59
                        mol_type = other DNA
                        organism = synthetic construct
SEQUENCE: 145
tcgtcggcag cgtcagatgt gtataagaga caggagttga gctccatttc cctacccca      59

SEQ ID NO: 146          moltype = DNA  length = 64
FEATURE                 Location/Qualifiers
source                  1..64
                        mol_type = other DNA
                        organism = synthetic construct
SEQUENCE: 146
gtctcgtggg ctcggagatg tgtataagag acagactgtg tgagaagagg tcagaaagcc     60
agtc                                                                  64

SEQ ID NO: 147          moltype = DNA  length = 64
FEATURE                 Location/Qualifiers
source                  1..64
                        mol_type = other DNA
                        organism = synthetic construct
SEQUENCE: 147
gtctcgtggg ctcggagatg tgtataagag acagtggtga agagaagagg tcagaaagcc     60
agtc                                                                  64

SEQ ID NO: 148          moltype = DNA  length = 64
FEATURE                 Location/Qualifiers
source                  1..64
                        mol_type = other DNA
                        organism = synthetic construct
SEQUENCE: 148
gtctcgtggg ctcggagatg tgtataagag acagcttctc ctagaagagg tcagaaagcc     60
agtc                                                                  64

SEQ ID NO: 149          moltype = DNA  length = 64
FEATURE                 Location/Qualifiers
source                  1..64
                        mol_type = other DNA
                        organism = synthetic construct
SEQUENCE: 149
gtctcgtggg ctcggagatg tgtataagag acaggagtgt ctagaagagg tcagaaagcc     60
agtc                                                                  64

SEQ ID NO: 150          moltype = DNA  length = 60
FEATURE                 Location/Qualifiers
source                  1..60
                        mol_type = other DNA
                        organism = synthetic construct
SEQUENCE: 150
gtctcgtggg ctcggagatg tgtataagag acagactgtg tggtcagaaa gccagtcgcg     60

SEQ ID NO: 151          moltype = DNA  length = 60
FEATURE                 Location/Qualifiers
source                  1..60
                        mol_type = other DNA
                        organism = synthetic construct
SEQUENCE: 151
gtctcgtggg ctcggagatg tgtataagag acagtggtga aggtcagaaa gccagtcgcg     60

SEQ ID NO: 152          moltype = DNA  length = 60
FEATURE                 Location/Qualifiers
```

```
source                      1..60
                            mol_type = other DNA
                            organism = synthetic construct
SEQUENCE: 152
gtctcgtggg ctcggagatg tgtataagag acagcttctc ctgtcagaaa gccagtcgcg    60

SEQ ID NO: 153              moltype = DNA   length = 60
FEATURE                     Location/Qualifiers
source                      1..60
                            mol_type = other DNA
                            organism = synthetic construct
SEQUENCE: 153
gtctcgtggg ctcggagatg tgtataagag acaggagtgt ctgtcagaaa gccagtcgcg    60

SEQ ID NO: 154              moltype = DNA   length = 24
FEATURE                     Location/Qualifiers
source                      1..24
                            mol_type = other DNA
                            organism = synthetic construct
SEQUENCE: 154
gtgaatgact aagctccatt tccc                                           24

SEQ ID NO: 155              moltype = DNA   length = 22
FEATURE                     Location/Qualifiers
source                      1..22
                            mol_type = other DNA
                            organism = synthetic construct
SEQUENCE: 155
agaagaggtc agaaagccag tc                                             22

SEQ ID NO: 156              moltype = DNA   length = 18
FEATURE                     Location/Qualifiers
source                      1..18
                            mol_type = other DNA
                            organism = synthetic construct
SEQUENCE: 156
ctccatttcc ctacccca                                                  18

SEQ ID NO: 157              moltype = DNA   length = 18
FEATURE                     Location/Qualifiers
source                      1..18
                            mol_type = other DNA
                            organism = synthetic construct
SEQUENCE: 157
gtcagaaagc cagtcgcg                                                  18

SEQ ID NO: 158              moltype = DNA   length = 21
FEATURE                     Location/Qualifiers
source                      1..21
                            mol_type = other DNA
                            organism = synthetic construct
SEQUENCE: 158
ccctacccca cccttattac a                                              21

SEQ ID NO: 159              moltype = DNA   length = 20
FEATURE                     Location/Qualifiers
source                      1..20
                            mol_type = other DNA
                            organism = synthetic construct
SEQUENCE: 159
gaggtcagaa agccagtcgc                                                20

SEQ ID NO: 160              moltype = DNA   length = 259
FEATURE                     Location/Qualifiers
source                      1..259
                            mol_type = other DNA
                            organism = synthetic construct
SEQUENCE: 160
cactaaggca attggggtgc aggaatgggg gcagggtacc agcctcacca agtggttgat    60
aaacccacgt ggggtaccct aagaacttgg gaacagccac agcagggggg cgatgcttgg   120
ggacctgcct ggagaaggat gcaggacgag aaacacagcc ccaggtggag aaactggccg   180
ggaatcaaga gtcacccaga gacagtgacc aaccatccct gttttcctag gactgagggt   240
ttcagtgcta aaactaggc                                                259

SEQ ID NO: 161              moltype = DNA   length = 196
FEATURE                     Location/Qualifiers
source                      1..196
                            mol_type = other DNA
                            organism = synthetic construct
```

```
SEQUENCE: 161
cactaaggca attggggtgc aggaatgggg cagggtacc agcctcacca agtggttgat      60
aaacccgtgc cagggcgtgc ccttgggctc cccgggcgcg tgtggagaaa ctggccggga    120
atcaagagtc acccagagac agtgaccaac catccctgtt ttcctaggac tgagggtttc    180
agtgctaaaa ctaggc                                                    196

SEQ ID NO: 162           moltype = DNA   length = 202
FEATURE                  Location/Qualifiers
source                   1..202
                         mol_type = other DNA
                         organism = synthetic construct
SEQUENCE: 162
cactaaggca attggggtgc aggaatgggg cagggtacc agcctcacca agtggttgat      60
aaacccgccc ccaactgaga gaactcaaag gttacccag ttggggcgtg gagaaactgg    120
ccgggaatca agagtcaccc agagacagtg accaaccatc cctgttttcc taggactgag    180
ggtttcagtg ctaaaactag gc                                             202

SEQ ID NO: 163           moltype = DNA   length = 251
FEATURE                  Location/Qualifiers
source                   1..251
                         mol_type = other DNA
                         organism = synthetic construct
SEQUENCE: 163
gccaggacgg ggctggctac tggccttatc tcacaggtaa aactgacgca cggaggaaca     60
atataaattg gggactagaa aggtgaagag ccaaagttag aactcaggac caacttattc    120
tgatttgtt tttccaaact gcttctcctc ttgggaagtg taaggaagct gcagcaccag    180
gatcagtgaa acgcaccaga cagccgcgtc agagcagctc aggttctggg agagggtagc    240
gcagggtggc c                                                         251

SEQ ID NO: 164           moltype = DNA   length = 184
FEATURE                  Location/Qualifiers
source                   1..184
                         mol_type = other DNA
                         organism = synthetic construct
SEQUENCE: 164
gccaggacgg ggctggctac tggccttatc tcacaggtaa aactgacgca gtgccagggc     60
gtgcccttgg gctccccggg cgcgtgggaa gtgtaaggaa gctgcagcac caggatcagt    120
gaaacgcacc agacagccgc gtcagagcag ctcaggttct gggagagggt agcgcagggt    180
ggcc                                                                 184

SEQ ID NO: 165           moltype = DNA   length = 190
FEATURE                  Location/Qualifiers
source                   1..190
                         mol_type = other DNA
                         organism = synthetic construct
SEQUENCE: 165
gccaggacgg ggctggctac tggccttatc tcacaggtaa aactgacgca gcccccaact     60
gagagaactc aaaggttacc ccagttgggg cgggaagtgt aaggaagctg cagcaccagg    120
atcagtgaaa cgcaccagac agccgcgtca gagcagctca ggttctggga gagggtagcg    180
cagggtggcc                                                           190

SEQ ID NO: 166           moltype = DNA   length = 256
FEATURE                  Location/Qualifiers
source                   1..256
                         mol_type = other DNA
                         organism = synthetic construct
SEQUENCE: 166
aactgcttct cctcttggga agtgtaagga agctgcagca ccaggatcag tgaaacgcac     60
cagacagccg cgtcagagca gctcaggttc tgggagaggg tagcgcaggg tggccactga    120
gaaccgggca ggtcacgcat ccccccttc cctcccaccc cctgccaagc tctccctccc    180
aggatcctct ctggctccat cgtaagcaaa ccttagaggt tctggcaagg agagagatgg    240
ctccaggaaa tggggg                                                    256

SEQ ID NO: 167           moltype = DNA   length = 182
FEATURE                  Location/Qualifiers
source                   1..182
                         mol_type = other DNA
                         organism = synthetic construct
SEQUENCE: 167
aactgcttct cctcttggga agtgtaagga agctgcagca ccaggatcag tgaaacgcac     60
caggtttgtc tggtcaacca ccgcggtctc agtggtgtac ggtacaaacc tcctctctgg    120
ctccatcgta agcaaacctt agaggttctg gcaaggagag gatggctccc aggaaatggg    180
gg                                                                   182

SEQ ID NO: 168           moltype = DNA   length = 168
FEATURE                  Location/Qualifiers
source                   1..168
                         mol_type = other DNA
                         organism = synthetic construct
```

```
SEQUENCE: 168
aactgcttct cctcttggga agtgtaagga agctgcagca ccaggatcag tgaaacgcac    60
cgtgccaggg cgtgcccttg ggctcccggg gcgcgttcct ctctggctcc atcgtaagca   120
aaccttagag gttctggcaa ggagagagat ggctccagga aatggggg               168

SEQ ID NO: 169          moltype = DNA   length = 174
FEATURE                 Location/Qualifiers
source                  1..174
                        mol_type = other DNA
                        organism = synthetic construct
SEQUENCE: 169
aactgcttct cctcttggga agtgtaagga agctgcagca ccaggatcag tgaaacgcac    60
cgcccccaac tgagagaact caaaggttac cccagttggg gctcctctct ggctccatcg   120
taagcaaacc ttagaggttc tggcaaggag agagatggcc caggaaatg gggg          174

SEQ ID NO: 170          moltype = DNA   length = 256
FEATURE                 Location/Qualifiers
source                  1..256
                        mol_type = other DNA
                        organism = synthetic construct
SEQUENCE: 170
aactgcttct cctcttggga agtgtaagga agctgcagca ccaggatcag tgaaacgcac    60
cagacagccg cgtcagagca gctcaggttc tgggagaggg tagcgcaggg tggccactga   120
gaaccgggca ggtcacgcat ccccccttc cctcccaccc cctgccaagc tctccctccc   180
aggatcctct ctggctccat cgtaagcaaa ccttagaggt tctggcaagg agagagatgg   240
ctccaggaaa tggggg                                                   256

SEQ ID NO: 171          moltype = DNA   length = 215
FEATURE                 Location/Qualifiers
source                  1..215
                        mol_type = other DNA
                        organism = synthetic construct
SEQUENCE: 171
aactgcttct cctcttggga agtgtaagga agctgcagca ccaggatcag tgaaacgcac    60
cagacagccg cgtcagagca gctcaggttc tgggaggttt gtctggtcaa ccaccgcggt   120
ctcagtggtg tacggtacaa acctcctctc tggctccatc gtaagcaaac cttagaggtt   180
ctggcaagga gagagatggc tccaggaaat ggggg                              215

SEQ ID NO: 172          moltype = DNA   length = 201
FEATURE                 Location/Qualifiers
source                  1..201
                        mol_type = other DNA
                        organism = synthetic construct
SEQUENCE: 172
aactgcttct cctcttggga agtgtaagga agctgcagca ccaggatcag tgaaacgcac    60
cagacagccg cgtcagagca gctcaggttc tggggtgcca gggcgtgccc ttgggctccc   120
cgggcgcgtt cctctctggc tccatcgtaa gcaaaccttg aggttctgg caaggagaga   180
gatggctcca ggaaatgggg g                                             201

SEQ ID NO: 173          moltype = DNA   length = 207
FEATURE                 Location/Qualifiers
source                  1..207
                        mol_type = other DNA
                        organism = synthetic construct
SEQUENCE: 173
aactgcttct cctcttggga agtgtaagga agctgcagca ccaggatcag tgaaacgcac    60
cagacagccg cgtcagagca gctcaggttc tggggccccc aactgagaga actcaaaggt   120
taccccagtt ggggctcctc tctggctcca tcgtaagcaa accttagagg ttctggcaag   180
gagagagatg gctccaggaa atggggg                                       207

SEQ ID NO: 174          moltype = DNA   length = 249
FEATURE                 Location/Qualifiers
source                  1..249
                        mol_type = other DNA
                        organism = synthetic construct
SEQUENCE: 174
gggagggaag cactggtttc tcaagcaaaa gctaaaattt ttctattaag atttaacctg    60
atgctacact ttggtggtgc agcaagggtc tcaaatggta taaaactcag gtgatcatgc   120
tttatgtctg tctctagaaa aatgctccaa aaatgataag tagtgataat ccgcagtctc   180
gttgcataaa atcagcccca ggtgaatgac taagctccat ttccctaccc caccttatt   240
acaataacc                                                           249

SEQ ID NO: 175          moltype = DNA   length = 188
FEATURE                 Location/Qualifiers
source                  1..188
                        mol_type = other DNA
                        organism = synthetic construct
SEQUENCE: 175
gggagggaag cactggtttc tcaagcaaaa gctaaaattt ttctattaag atttaacctg    60
```

```
atgctacact ttggtggtgc agcaagggtc tcaaatggta taaaagtgcc agggcgtgcc   120
cttgggctcc ccgggcgcgt gtgaatgact aagctccatt tccctacccc acccttatta   180
caataacc                                                            188

SEQ ID NO: 176           moltype = DNA   length = 194
FEATURE                  Location/Qualifiers
source                   1..194
                         mol_type = other DNA
                         organism = synthetic construct
SEQUENCE: 176
gggagggaag cactggtttc tcaagcaaaa gctaaaattt ttctattaag atttaacctg   60
atgctacact ttggtggtgc agcaagggtc tcaaatggta taaaagcccc caactgagag   120
aactcaaagg ttaccccagt tggggcgtga atgactaagc tccatttccc taccccaccc   180
ttattacaat aacc                                                     194

SEQ ID NO: 177           moltype = DNA   length = 251
FEATURE                  Location/Qualifiers
source                   1..251
                         mol_type = other DNA
                         organism = synthetic construct
SEQUENCE: 177
gagagggaga aagctagtgc tatgtctgaa tactagagga gcaagtacaa caaatggaaa   60
atgggatcaa gtatgagtga gagttgctaa gatgcctggt agggatgcaa agggtagag   120
agcctgggga gagagggtga gggagggaag cactggtttc tcaagcaaaa gctaaaattt   180
ttctattaag atttaacctg atgctacact ttggtggtgc agcaagggtc tcaaatggta   240
taaaactcag g                                                        251

SEQ ID NO: 178           moltype = DNA   length = 192
FEATURE                  Location/Qualifiers
source                   1..192
                         mol_type = other DNA
                         organism = synthetic construct
SEQUENCE: 178
gagagggaga aagctagtgc tatgtctgaa tactagagga gcaagtacaa caaatggaaa   60
atgggatcaa gtatgagtga gagttgctaa gatgcctggt agggatgcgc gccagggcgt   120
gcccttgggc tccccgggcg cgtgctacac tttggtggtg cagcaagggt ctcaaatggt   180
ataaaactca gg                                                       192

SEQ ID NO: 179           moltype = DNA   length = 198
FEATURE                  Location/Qualifiers
source                   1..198
                         mol_type = other DNA
                         organism = synthetic construct
SEQUENCE: 179
gagagggaga aagctagtgc tatgtctgaa tactagagga gcaagtacaa caaatggaaa   60
atgggatcaa gtatgagtga gagttgctaa gatgcctggt agggatgcgc cccaactga   120
gagaactcaa aggttacccc agttgggcg ctacactttg tggtgcagc aagggtctca   180
aatggtataa aactcagg                                                 198

SEQ ID NO: 180           moltype = DNA   length = 261
FEATURE                  Location/Qualifiers
source                   1..261
                         mol_type = other DNA
                         organism = synthetic construct
SEQUENCE: 180
aaggagaatg acagacaata gtatatatga aatattctta tcaaaagata agatctactc   60
taattaaacc tgtagggaaa aagggacaa aggagcatgt taaacaatat catgagaata   120
gaatgagcaa actctagaat gtgggaaact taggaagaca cccagtttct tcaacaaaaa   180
aattgcaaaa ataaaaagga caaggagaa cctatagatt aaatgaggca ttaaagacat   240
atcaaccaaa tgtaacctgg g                                             261

SEQ ID NO: 181           moltype = DNA   length = 151
FEATURE                  Location/Qualifiers
source                   1..151
                         mol_type = other DNA
                         organism = synthetic construct
SEQUENCE: 181
aaggagaatg acagacaata gtatatatga aatattctta tcaaaagata agatctactc   60
taattaaacc tgtgccaggg cgtgcccttg gctccccgg gcgcgtgatt aaatgaggca   120
ttaaagacat atcaaccaaa tgtaacctgg g                                  151

SEQ ID NO: 182           moltype = DNA   length = 157
FEATURE                  Location/Qualifiers
source                   1..157
                         mol_type = other DNA
                         organism = synthetic construct
SEQUENCE: 182
aaggagaatg acagacaata gtatatatga aatattctta tcaaaagata agatctactc   60
taattaaacc tgccccaac tgagagaact caaaggttac cccagttggg gcgattaaat   120
```

```
gaggcattaa agacatatca accaaatgta acctggg                                   157

SEQ ID NO: 183          moltype = DNA   length = 279
FEATURE                 Location/Qualifiers
source                  1..279
                        mol_type = other DNA
                        organism = synthetic construct
SEQUENCE: 183
aaggagaatg acagacaata gtatatatga aatattctta tcaaaagata agatctactc          60
taattaaacc tgtagggaaa aaagggacaa aggagcatgt taaacaatat catgagaata         120
gaatgagcaa actctagaat gtgggaaact taggaagaca cccagtttct tcaacaaaaa         180
aattgcaaaa ataaaaagga acaaggagaa cctatagatt aaatgaggca ttaaagacat         240
atcaaccaaa tgtaacctgg ggaccattta aaatacctg                                279

SEQ ID NO: 184          moltype = DNA   length = 134
FEATURE                 Location/Qualifiers
source                  1..134
                        mol_type = other DNA
                        organism = synthetic construct
SEQUENCE: 184
aaggagaatg acagacaata gtatatatga aatattctta tcaaaagata agatctactc          60
taattaaacc tgtgccaggg cgtgcccttg ggctccccgg gcgcgtgtaa cctggggacc         120
atttaaaata cctg                                                           134

SEQ ID NO: 185          moltype = DNA   length = 140
FEATURE                 Location/Qualifiers
source                  1..140
                        mol_type = other DNA
                        organism = synthetic construct
SEQUENCE: 185
aaggagaatg acagacaata gtatatatga aatattctta tcaaaagata agatctactc          60
taattaaacc tgcccccaac tgagagaact caaaggttac cccagttggg gcgtaacctg         120
gggaccattt aaaatacctg                                                     140

SEQ ID NO: 186          moltype = DNA   length = 279
FEATURE                 Location/Qualifiers
source                  1..279
                        mol_type = other DNA
                        organism = synthetic construct
SEQUENCE: 186
aaggagaatg acagacaata gtatatatga aatattctta tcaaaagata agatctactc          60
taattaaacc tgtagggaaa aaagggacaa aggagcatgt taaacaatat catgagaata         120
gaatgagcaa actctagaat gtgggaaact taggaagaca cccagtttct tcaacaaaaa         180
aattgcaaaa ataaaaagga acaaggagaa cctatagatt aaatgaggca ttaaagacat         240
atcaaccaaa tgtaacctgg ggaccattta aaatacctg                                279

SEQ ID NO: 187          moltype = DNA   length = 236
FEATURE                 Location/Qualifiers
source                  1..236
                        mol_type = other DNA
                        organism = synthetic construct
SEQUENCE: 187
aaggagaatg acagacaata gtatatatga aatattctta tcaaaagata agatctactc          60
taattaaacc tgtagggaaa aaagggacaa aggagcatgt taaacaatat catgagaata         120
gaatgagcaa actctagagt gccagggcgt gcccttgggc tccccgggcg cgtgattaaa         180
tgaggcatta aagacatatc aaccaaatgt aacctgggga ccatttaaaa tacctg             236

SEQ ID NO: 188          moltype = DNA   length = 242
FEATURE                 Location/Qualifiers
source                  1..242
                        mol_type = other DNA
                        organism = synthetic construct
SEQUENCE: 188
aaggagaatg acagacaata gtatatatga aatattctta tcaaaagata agatctactc          60
taattaaacc tgtagggaaa aaagggacaa aggagcatgt taaacaatat catgagaata         120
gaatgagcaa actctagagc ccccaactga gagaactcaa aggttacccc agttggggcg         180
attaaatgag gcattaaaga catatcaacc aaatgtaacc tggggaccat ttaaaatacc         240
tg                                                                        242

SEQ ID NO: 189          moltype = DNA   length = 279
FEATURE                 Location/Qualifiers
source                  1..279
                        mol_type = other DNA
                        organism = synthetic construct
SEQUENCE: 189
aaggagaatg acagacaata gtatatatga aatattctta tcaaaagata agatctactc          60
taattaaacc tgtagggaaa aaagggacaa aggagcatgt taaacaatat catgagaata         120
gaatgagcaa actctagaat gtgggaaact taggaagaca cccagtttct tcaacaaaaa         180
aattgcaaaa ataaaaagga acaaggagaa cctatagatt aaatgaggca ttaaagacat         240
```

-continued

```
atcaaccaaa tgtaacctgg ggaccattta aaatacctg                                279

SEQ ID NO: 190          moltype = DNA   length = 201
FEATURE                 Location/Qualifiers
source                  1..201
                        mol_type = other DNA
                        organism = synthetic construct
SEQUENCE: 190
aaggagaatg acagacaata gtatatatga aatattctta tcaaaagata agatctactc          60
taattaaacc tgtagggaaa aaagggacaa aggagcatgt taaacaatat catgagaata         120
gaatgagcaa actctagagt gccagggcgt gcccttgggc tccccgggcg cgtgtaacct         180
ggggaccatt taaaatacct g                                                   201

SEQ ID NO: 191          moltype = DNA   length = 207
FEATURE                 Location/Qualifiers
source                  1..207
                        mol_type = other DNA
                        organism = synthetic construct
SEQUENCE: 191
aaggagaatg acagacaata gtatatatga aatattctta tcaaaagata agatctactc          60
taattaaacc tgtagggaaa aaagggacaa aggagcatgt taaacaatat catgagaata         120
gaatgagcaa actctagagc ccccaactga gagaactcaa aggttacccc agttgggcg         180
taacctgggg accatttaaa atacctg                                             207

SEQ ID NO: 192          moltype = DNA   length = 20
FEATURE                 Location/Qualifiers
source                  1..20
                        mol_type = other DNA
                        organism = synthetic construct
SEQUENCE: 192
gtttgtccaa actcagcggc                                                      20

SEQ ID NO: 193          moltype = DNA   length = 20
FEATURE                 Location/Qualifiers
source                  1..20
                        mol_type = other DNA
                        organism = synthetic construct
SEQUENCE: 193
gaaggtacgc ctgcaggtac                                                      20

SEQ ID NO: 194          moltype = DNA   length = 20
FEATURE                 Location/Qualifiers
source                  1..20
                        mol_type = other DNA
                        organism = synthetic construct
SEQUENCE: 194
atccagcctc cggactctag                                                      20

SEQ ID NO: 195          moltype = DNA   length = 16
FEATURE                 Location/Qualifiers
source                  1..16
                        mol_type = other DNA
                        organism = synthetic construct
SEQUENCE: 195
ccggggagcc caaggg                                                          16

SEQ ID NO: 196          moltype = DNA   length = 20
FEATURE                 Location/Qualifiers
source                  1..20
                        mol_type = other DNA
                        organism = synthetic construct
SEQUENCE: 196
gagttctctc agttggggc                                                       20

SEQ ID NO: 197          moltype = DNA   length = 22
FEATURE                 Location/Qualifiers
source                  1..22
                        mol_type = other DNA
                        organism = synthetic construct
SEQUENCE: 197
ccaactgggg taacctttga gt                                                   22

SEQ ID NO: 198          moltype = DNA   length = 20
FEATURE                 Location/Qualifiers
source                  1..20
                        mol_type = other DNA
                        organism = synthetic construct
SEQUENCE: 198
tccgcagtct cgttgcataa                                                      20
```

```
SEQ ID NO: 199           moltype = DNA   length = 23
FEATURE                  Location/Qualifiers
source                   1..23
                         mol_type = other DNA
                         organism = synthetic construct
SEQUENCE: 199
acaacaaatg gaaaatggga tca                                               23

SEQ ID NO: 200           moltype = DNA   length = 20
FEATURE                  Location/Qualifiers
source                   1..20
                         mol_type = other DNA
                         organism = synthetic construct
SEQUENCE: 200
agaacgtgaa ctagggagga                                                   20

SEQ ID NO: 201           moltype = DNA   length = 25
FEATURE                  Location/Qualifiers
source                   1..25
                         mol_type = other DNA
                         organism = synthetic construct
SEQUENCE: 201
agcctctata ttctaatcca cttgt                                             25

SEQ ID NO: 202           moltype = DNA   length = 20
FEATURE                  Location/Qualifiers
source                   1..20
                         mol_type = other DNA
                         organism = synthetic construct
SEQUENCE: 202
ctgtgcctag cctaagcctc                                                   20

SEQ ID NO: 203           moltype = DNA   length = 20
FEATURE                  Location/Qualifiers
source                   1..20
                         mol_type = other DNA
                         organism = synthetic construct
SEQUENCE: 203
tgctggaatt acaggcgtga                                                   20

SEQ ID NO: 204           moltype = DNA   length = 23
FEATURE                  Location/Qualifiers
source                   1..23
                         mol_type = other DNA
                         organism = synthetic construct
SEQUENCE: 204
gcttctcctc ttgggaagtg taa                                               23

SEQ ID NO: 205           moltype = DNA   length = 20
FEATURE                  Location/Qualifiers
source                   1..20
                         mol_type = other DNA
                         organism = synthetic construct
SEQUENCE: 205
aagggagttt tccacacgga                                                   20

SEQ ID NO: 206           moltype = DNA   length = 20
FEATURE                  Location/Qualifiers
source                   1..20
                         mol_type = other DNA
                         organism = synthetic construct
SEQUENCE: 206
cactaaggca attgggtgc                                                    20

SEQ ID NO: 207           moltype = DNA   length = 18
FEATURE                  Location/Qualifiers
source                   1..18
                         mol_type = other DNA
                         organism = synthetic construct
SEQUENCE: 207
gtcgacgacg gcggtctc                                                     18

SEQ ID NO: 208           moltype = DNA   length = 20
FEATURE                  Location/Qualifiers
source                   1..20
                         mol_type = other DNA
                         organism = synthetic construct
SEQUENCE: 208
```
ctccgtcgtc aggatcatcc                                                    20

SEQ ID NO: 209         moltype = DNA   length = 19
FEATURE                Location/Qualifiers
source                 1..19
                       mol_type = other DNA
                       organism = synthetic construct SEQUENCE: 209
gtacaccact gagaccgcg                                                     19

SEQ ID NO: 210         moltype = DNA   length = 19
FEATURE                Location/Qualifiers
source                 1..19
                       mol_type = other DNA
                       organism = synthetic construct SEQUENCE: 210
ccgtgaccta catgctcgc                                                     19

SEQ ID NO: 211         moltype = DNA   length = 18
FEATURE                Location/Qualifiers
source                 1..18
                       mol_type = other DNA
                       organism = synthetic construct SEQUENCE: 211
ctcgaagggc gtatgcgc                                                      18

SEQ ID NO: 212         moltype = DNA   length = 33
FEATURE                Location/Qualifiers
source                 1..33
                       mol_type = other DNA
                       organism = synthetic construct SEQUENCE: 212
ccccaggtga atgactaagc tccatttccc tac                                     33

SEQ ID NO: 213         moltype = DNA   length = 20
FEATURE                Location/Qualifiers
source                 1..20
                       mol_type = other DNA
                       organism = synthetic construct SEQUENCE: 213
ggggagtgag cagctgtaag                                                    20

SEQ ID NO: 214         moltype = DNA   length = 33
FEATURE                Location/Qualifiers
source                 1..33
                       mol_type = other DNA
                       organism = synthetic construct SEQUENCE: 214
agtgagagtt gctaagatgc ctggtaggga tgc                                     33

SEQ ID NO: 215         moltype = DNA   length = 20
FEATURE                Location/Qualifiers
source                 1..20
                       mol_type = other DNA
                       organism = synthetic construct SEQUENCE: 215
tgctgcacca ccaaagtgta                                                    20

SEQ ID NO: 216         moltype = DNA   length = 33
FEATURE                Location/Qualifiers
source                 1..33
                       mol_type = other DNA
                       organism = synthetic construct SEQUENCE: 216
tagggccctg atatgggcac ccaaatgtag ctt                                     33

SEQ ID NO: 217         moltype = DNA   length = 20
FEATURE                Location/Qualifiers
source                 1..20
                       mol_type = other DNA
                       organism = synthetic construct SEQUENCE: 217
aacatgctcc tttgtcccttt                                                   20

SEQ ID NO: 218         moltype = DNA   length = 28
FEATURE                Location/Qualifiers
source                 1..28
                       mol_type = other DNA
                       organism = synthetic construct

| | | |
|---|---|---|
| SEQUENCE: 218 | | |
| ctgcagcacc aggatcagtg aaacgcac | | 28 |
| SEQ ID NO: 219 | moltype = DNA  length = 19 | |
| FEATURE | Location/Qualifiers | |
| source | 1..19 | |
| | mol_type = other DNA | |
| | organism = synthetic construct | |
| SEQUENCE: 219 | | |
| gttctcagtg gccaccctg | | 19 |
| SEQ ID NO: 220 | moltype = DNA  length = 24 | |
| FEATURE | Location/Qualifiers | |
| source | 1..24 | |
| | mol_type = other DNA | |
| | organism = synthetic construct | |
| SEQUENCE: 220 | | |
| cccctcctca ccacagccct gcca | | 24 |
| SEQ ID NO: 221 | moltype = DNA  length = 22 | |
| FEATURE | Location/Qualifiers | |
| source | 1..22 | |
| | mol_type = other DNA | |
| | organism = synthetic construct | |
| SEQUENCE: 221 | | |
| ggctcttcac ctttctagtc cc | | 22 |
| SEQ ID NO: 222 | moltype = DNA  length = 33 | |
| FEATURE | Location/Qualifiers | |
| source | 1..33 | |
| | mol_type = other DNA | |
| | organism = synthetic construct | |
| SEQUENCE: 222 | | |
| taccagcctc accaagtggt tgataaaccc acg | | 33 |
| SEQ ID NO: 223 | moltype = DNA  length = 20 | |
| FEATURE | Location/Qualifiers | |
| source | 1..20 | |
| | mol_type = other DNA | |
| | organism = synthetic construct | |
| SEQUENCE: 223 | | |
| ctcgtcctgc atccttctcc | | 20 |
| SEQ ID NO: 224 | moltype = DNA  length = 17 | |
| FEATURE | Location/Qualifiers | |
| source | 1..17 | |
| | mol_type = other DNA | |
| | organism = synthetic construct | |
| SEQUENCE: 224 | | |
| acactgtgcc catctac | | 17 |
| SEQ ID NO: 225 | moltype = DNA  length = 18 | |
| FEATURE | Location/Qualifiers | |
| source | 1..18 | |
| | mol_type = other DNA | |
| | organism = synthetic construct | |
| SEQUENCE: 225 | | |
| aatgtcacgc acgatttc | | 18 |
| SEQ ID NO: 226 | moltype = DNA  length = 19 | |
| FEATURE | Location/Qualifiers | |
| source | 1..19 | |
| | mol_type = other DNA | |
| | organism = synthetic construct | |
| SEQUENCE: 226 | | |
| agatttggac ctgcgagcg | | 19 |
| SEQ ID NO: 227 | moltype = DNA  length = 20 | |
| FEATURE | Location/Qualifiers | |
| source | 1..20 | |
| | mol_type = other DNA | |
| | organism = synthetic construct | |
| SEQUENCE: 227 | | |
| gagcggctgt ctccacaagt | | 20 |
| SEQ ID NO: 228 | moltype = DNA  length = 24 | |
| FEATURE | Location/Qualifiers | |
| source | 1..24 | |
| | mol_type = other DNA | |

```
                          organism = synthetic construct
SEQUENCE: 228
gtactcttgt ccatctgttc tctg                                            24

SEQ ID NO: 229          moltype = DNA  length = 22
FEATURE                 Location/Qualifiers
source                  1..22
                        mol_type = other DNA
                        organism = synthetic construct
SEQUENCE: 229
ggccgatatt cagcccttaa ac                                              22

SEQ ID NO: 230          moltype = DNA  length = 33
FEATURE                 Location/Qualifiers
source                  1..33
                        mol_type = other DNA
                        organism = synthetic construct
SEQUENCE: 230
ccgtgaccta catgctcgaa gggcgtatgc gcc                                  33

SEQ ID NO: 231          moltype = DNA  length = 104
FEATURE                 Location/Qualifiers
source                  1..104
                        mol_type = other DNA
                        organism = synthetic construct
SEQUENCE: 231
gtaacgctct tcgagaaagc agattctcat atccatcttg agtcttcttt ctcgcaagac     60
aacacgaaat agacacagtc tcttccctag ctgtacactg agcc                     104

SEQ ID NO: 232          moltype = DNA  length = 28
FEATURE                 Location/Qualifiers
source                  1..28
                        mol_type = other DNA
                        organism = synthetic construct
SEQUENCE: 232
ttctagagac agacataaag catgatca                                        28

SEQ ID NO: 233          moltype = DNA  length = 26
FEATURE                 Location/Qualifiers
source                  1..26
                        mol_type = other DNA
                        organism = synthetic construct
SEQUENCE: 233
ggaaataagt tatcacaatg ggaaat                                          26

SEQ ID NO: 234          moltype = DNA  length = 22
FEATURE                 Location/Qualifiers
source                  1..22
                        mol_type = other DNA
                        organism = synthetic construct
SEQUENCE: 234
tcgcgattct taaaaggaga gg                                              22

SEQ ID NO: 235          moltype = DNA  length = 24
FEATURE                 Location/Qualifiers
source                  1..24
                        mol_type = other DNA
                        organism = synthetic construct
SEQUENCE: 235
ccattcatat tttgaaacaa aagg                                            24

SEQ ID NO: 236          moltype = DNA  length = 23
FEATURE                 Location/Qualifiers
source                  1..23
                        mol_type = other DNA
                        organism = synthetic construct
SEQUENCE: 236
gcattgcact cctacataca aca                                             23

SEQ ID NO: 237          moltype = DNA  length = 20
FEATURE                 Location/Qualifiers
source                  1..20
                        mol_type = other DNA
                        organism = synthetic construct
SEQUENCE: 237
gctgtggtta ttcccagctc                                                 20

SEQ ID NO: 238          moltype = DNA  length = 22
FEATURE                 Location/Qualifiers
```

```
                          source              1..22
                                              mol_type = other DNA
                                              organism = synthetic construct
SEQUENCE: 238
ctgggaacac tggacaaaat cc                                                    22

SEQ ID NO: 239            moltype = DNA   length = 21
FEATURE                   Location/Qualifiers
source                    1..21
                          mol_type = other DNA
                          organism = synthetic construct
SEQUENCE: 239
ggaaagcttt gacaagtgga a                                                     21

SEQ ID NO: 240            moltype = DNA   length = 20
FEATURE                   Location/Qualifiers
source                    1..20
                          mol_type = other DNA
                          organism = synthetic construct
SEQUENCE: 240
gcctacttgc ccttcttcct                                                       20

SEQ ID NO: 241            moltype = DNA   length = 23
FEATURE                   Location/Qualifiers
source                    1..23
                          mol_type = other DNA
                          organism = synthetic construct
SEQUENCE: 241
agggaccttt gcctgtgtga gtc                                                   23

SEQ ID NO: 242            moltype = DNA   length = 20
FEATURE                   Location/Qualifiers
source                    1..20
                          mol_type = other DNA
                          organism = synthetic construct
SEQUENCE: 242
cactcacaca gacagaggcc                                                       20

SEQ ID NO: 243            moltype = DNA   length = 26
FEATURE                   Location/Qualifiers
source                    1..26
                          mol_type = other DNA
                          organism = synthetic construct
SEQUENCE: 243
ccaggtgaga gtcagggtag tgttca                                                26

SEQ ID NO: 244            moltype = DNA   length = 17
FEATURE                   Location/Qualifiers
source                    1..17
                          mol_type = other DNA
                          organism = synthetic construct
SEQUENCE: 244
gcttgcgcgg cctacgt                                                          17

SEQ ID NO: 245            moltype = DNA   length = 21
FEATURE                   Location/Qualifiers
source                    1..21
                          mol_type = other DNA
                          organism = synthetic construct
SEQUENCE: 245
tcagctctgt gctgaggcga a                                                     21

SEQ ID NO: 246            moltype = DNA   length = 18
FEATURE                   Location/Qualifiers
source                    1..18
                          mol_type = other DNA
                          organism = synthetic construct
SEQUENCE: 246
gcacaaccct ggctgtcc                                                         18

SEQ ID NO: 247            moltype = DNA   length = 27
FEATURE                   Location/Qualifiers
source                    1..27
                          mol_type = other DNA
                          organism = synthetic construct
SEQUENCE: 247
tgaatgcaat tgttgttgtt aacttgt                                               27

SEQ ID NO: 248            moltype = DNA   length = 20
```

```
FEATURE                 Location/Qualifiers
source                  1..20
                        mol_type = other DNA
                        organism = synthetic construct
SEQUENCE: 248
aagtggttga taaacccacg                                                    20

SEQ ID NO: 249          moltype = DNA   length = 20
FEATURE                 Location/Qualifiers
source                  1..20
                        mol_type = other DNA
                        organism = synthetic construct
SEQUENCE: 249
ccggccagtt tctccacctg                                                    20

SEQ ID NO: 250          moltype = DNA   length = 20
FEATURE                 Location/Qualifiers
source                  1..20
                        mol_type = other DNA
                        organism = synthetic construct
SEQUENCE: 250
caggtaaaac tgacgcacgg                                                    20

SEQ ID NO: 251          moltype = DNA   length = 20
FEATURE                 Location/Qualifiers
source                  1..20
                        mol_type = other DNA
                        organism = synthetic construct
SEQUENCE: 251
gcttccttac acttcccaag                                                    20

SEQ ID NO: 252          moltype = DNA   length = 20
FEATURE                 Location/Qualifiers
source                  1..20
                        mol_type = other DNA
                        organism = synthetic construct
SEQUENCE: 252
gatcagtgaa acgcaccaga                                                    20

SEQ ID NO: 253          moltype = DNA   length = 20
FEATURE                 Location/Qualifiers
source                  1..20
                        mol_type = other DNA
                        organism = synthetic construct
SEQUENCE: 253
gatggagcca gagaggatcc                                                    20

SEQ ID NO: 254          moltype = DNA   length = 20
FEATURE                 Location/Qualifiers
source                  1..20
                        mol_type = other DNA
                        organism = synthetic construct
SEQUENCE: 254
gcagctcagg ttctgggaga                                                    20

SEQ ID NO: 255          moltype = DNA   length = 20
FEATURE                 Location/Qualifiers
source                  1..20
                        mol_type = other DNA
                        organism = synthetic construct
SEQUENCE: 255
aagtggttga taaacccacg                                                    20

SEQ ID NO: 256          moltype = DNA   length = 20
FEATURE                 Location/Qualifiers
source                  1..20
                        mol_type = other DNA
                        organism = synthetic construct
SEQUENCE: 256
ccggccagtt tctccacctg                                                    20

SEQ ID NO: 257          moltype = DNA   length = 20
FEATURE                 Location/Qualifiers
source                  1..20
                        mol_type = other DNA
                        organism = synthetic construct
SEQUENCE: 257
caggtaaaac tgacgcacgg                                                    20
```

| | | |
|---|---|---|
| SEQ ID NO: 258<br>FEATURE<br>source | moltype = DNA   length = 20<br>Location/Qualifiers<br>1..20<br>mol_type = other DNA<br>organism = synthetic construct | |
| SEQUENCE: 258<br>gcttccttac acttcccaag | | 20 |
| SEQ ID NO: 259<br>FEATURE<br>source | moltype = DNA   length = 20<br>Location/Qualifiers<br>1..20<br>mol_type = other DNA<br>organism = synthetic construct | |
| SEQUENCE: 259<br>gatcagtgaa acgcaccaga | | 20 |
| SEQ ID NO: 260<br>FEATURE<br>source | moltype = DNA   length = 20<br>Location/Qualifiers<br>1..20<br>mol_type = other DNA<br>organism = synthetic construct | |
| SEQUENCE: 260<br>gatggagcca gagaggatcc | | 20 |
| SEQ ID NO: 261<br>FEATURE<br>source | moltype = DNA   length = 20<br>Location/Qualifiers<br>1..20<br>mol_type = other DNA<br>organism = synthetic construct | |
| SEQUENCE: 261<br>ctactctaat taaacctgta | | 20 |
| SEQ ID NO: 262<br>FEATURE<br>source | moltype = DNA   length = 20<br>Location/Qualifiers<br>1..20<br>mol_type = other DNA<br>organism = synthetic construct | |
| SEQUENCE: 262<br>taatgcctca tttaatctat | | 20 |
| SEQ ID NO: 263<br>FEATURE<br>source | moltype = DNA   length = 20<br>Location/Qualifiers<br>1..20<br>mol_type = other DNA<br>organism = synthetic construct | |
| SEQUENCE: 263<br>aatgagcaaa ctctagaatg | | 20 |
| SEQ ID NO: 264<br>FEATURE<br>source | moltype = DNA   length = 20<br>Location/Qualifiers<br>1..20<br>mol_type = other DNA<br>organism = synthetic construct | |
| SEQUENCE: 264<br>aatggtcccc aggttacatt | | 20 |
| SEQ ID NO: 265<br>FEATURE<br>source | moltype = DNA   length = 20<br>Location/Qualifiers<br>1..20<br>mol_type = other DNA<br>organism = synthetic construct | |
| SEQUENCE: 265<br>ctactctaat taaacctgta | | 20 |
| SEQ ID NO: 266<br>FEATURE<br>source | moltype = DNA   length = 20<br>Location/Qualifiers<br>1..20<br>mol_type = other DNA<br>organism = synthetic construct | |
| SEQUENCE: 266<br>taatgcctca tttaatctat | | 20 |
| SEQ ID NO: 267<br>FEATURE<br>source | moltype = DNA   length = 20<br>Location/Qualifiers<br>1..20<br>mol_type = other DNA<br>organism = synthetic construct | |
| SEQUENCE: 267<br>aatgagcaaa ctctagaatg | | 20 |

```
SEQ ID NO: 268          moltype = DNA  length = 20
FEATURE                 Location/Qualifiers
source                  1..20
                        mol_type = other DNA
                        organism = synthetic construct
SEQUENCE: 268
aatggtcccc aggttacatt                                                       20

SEQ ID NO: 269          moltype = DNA  length = 20
FEATURE                 Location/Qualifiers
source                  1..20
                        mol_type = other DNA
                        organism = synthetic construct
SEQUENCE: 269
tcgacaccaa ctctagtccg                                                       20

SEQ ID NO: 270          moltype = DNA  length = 20
FEATURE                 Location/Qualifiers
source                  1..20
                        mol_type = other DNA
                        organism = synthetic construct
SEQUENCE: 270
agtcgcttct cgattatggg                                                       20

SEQ ID NO: 271          moltype = DNA  length = 20
FEATURE                 Location/Qualifiers
source                  1..20
                        mol_type = other DNA
                        organism = synthetic construct
SEQUENCE: 271
ccctgggcgt tgccctgcag                                                       20

SEQ ID NO: 272          moltype = DNA  length = 20
FEATURE                 Location/Qualifiers
source                  1..20
                        mol_type = other DNA
                        organism = synthetic construct
SEQUENCE: 272
tctcaaatgg tataaaactc                                                       20

SEQ ID NO: 273          moltype = DNA  length = 20
FEATURE                 Location/Qualifiers
source                  1..20
                        mol_type = other DNA
                        organism = synthetic construct
SEQUENCE: 273
ggagcttagt cattcacctg                                                       20

SEQ ID NO: 274          moltype = DNA  length = 20
FEATURE                 Location/Qualifiers
source                  1..20
                        mol_type = other DNA
                        organism = synthetic construct
SEQUENCE: 274
atgcctggta gggatgcaaa                                                       20

SEQ ID NO: 275          moltype = DNA  length = 20
FEATURE                 Location/Qualifiers
source                  1..20
                        mol_type = other DNA
                        organism = synthetic construct
SEQUENCE: 275
caccaccaaa gtgtagcatc                                                       20

SEQ ID NO: 276          moltype = DNA  length = 20
FEATURE                 Location/Qualifiers
source                  1..20
                        mol_type = other DNA
                        organism = synthetic construct
SEQUENCE: 276
tcgacaccaa ctctagtccg                                                       20

SEQ ID NO: 277          moltype = DNA  length = 20
FEATURE                 Location/Qualifiers
source                  1..20
                        mol_type = other DNA
                        organism = synthetic construct
SEQUENCE: 277
```
agtcgcttct cgattatggg                                              20

SEQ ID NO: 278         moltype = DNA  length = 20
FEATURE                Location/Qualifiers
source                 1..20
                       mol_type = other DNA
                       organism = synthetic construct SEQUENCE: 278
ccctgggcgt tgccctgcag                                              20

SEQ ID NO: 279         moltype = DNA  length = 20
FEATURE                Location/Qualifiers
source                 1..20
                       mol_type = other DNA
                       organism = synthetic construct SEQUENCE: 279
tctcaaatgg tataaaactc                                              20

SEQ ID NO: 280         moltype = DNA  length = 20
FEATURE                Location/Qualifiers
source                 1..20
                       mol_type = other DNA
                       organism = synthetic construct SEQUENCE: 280
ggagcttagt cattcacctg                                              20

SEQ ID NO: 281         moltype = DNA  length = 20
FEATURE                Location/Qualifiers
source                 1..20
                       mol_type = other DNA
                       organism = synthetic construct SEQUENCE: 281
atgcctggta gggatgcaaa                                              20

SEQ ID NO: 282         moltype = DNA  length = 20
FEATURE                Location/Qualifiers
source                 1..20
                       mol_type = other DNA
                       organism = synthetic construct SEQUENCE: 282
caccaccaaa gtgtagcatc                                              20

SEQ ID NO: 283         moltype = DNA  length = 20
FEATURE                Location/Qualifiers
source                 1..20
                       mol_type = other DNA
                       organism = synthetic construct SEQUENCE: 283
atgcctggta gggatgcaaa                                              20

SEQ ID NO: 284         moltype = DNA  length = 20
FEATURE                Location/Qualifiers
source                 1..20
                       mol_type = other DNA
                       organism = synthetic construct SEQUENCE: 284
caccaccaaa gtgtagcatc                                              20

SEQ ID NO: 285         moltype = DNA  length = 20
FEATURE                Location/Qualifiers
source                 1..20
                       mol_type = other DNA
                       organism = synthetic construct SEQUENCE: 285
atgcctggta gggatgcaaa                                              20

SEQ ID NO: 286         moltype = DNA  length = 20
FEATURE                Location/Qualifiers
source                 1..20
                       mol_type = other DNA
                       organism = synthetic construct SEQUENCE: 286
caccaccaaa gtgtagcatc                                              20

SEQ ID NO: 287         moltype = DNA  length = 20
FEATURE                Location/Qualifiers
source                 1..20
                       mol_type = other DNA
                       organism = synthetic construct

```
SEQUENCE: 287
atgcctggta gggatgcaaa                                                      20

SEQ ID NO: 288         moltype = DNA   length = 20
FEATURE                Location/Qualifiers
source                 1..20
                       mol_type = other DNA
                       organism = synthetic construct
SEQUENCE: 288
caccaccaaa gtgtagcatc                                                      20

SEQ ID NO: 289         moltype = DNA   length = 27
FEATURE                Location/Qualifiers
source                 1..27
                       mol_type = other DNA
                       organism = synthetic construct
SEQUENCE: 289
ggggagccca agggcacgcc ctggcac                                              27

SEQ ID NO: 290         moltype = DNA   length = 28
FEATURE                Location/Qualifiers
source                 1..28
                       mol_type = other DNA
                       organism = synthetic construct
SEQUENCE: 290
ggcgtgccct tgggctcccc gggcgcgt                                             28

SEQ ID NO: 291         moltype = DNA   length = 27
FEATURE                Location/Qualifiers
source                 1..27
                       mol_type = other DNA
                       organism = synthetic construct
SEQUENCE: 291
ggggagccca agggcacgcc ctggcac                                              27

SEQ ID NO: 292         moltype = DNA   length = 28
FEATURE                Location/Qualifiers
source                 1..28
                       mol_type = other DNA
                       organism = synthetic construct
SEQUENCE: 292
ggcgtgccct tgggctcccc gggcgcgt                                             28

SEQ ID NO: 293         moltype = DNA   length = 27
FEATURE                Location/Qualifiers
source                 1..27
                       mol_type = other DNA
                       organism = synthetic construct
SEQUENCE: 293
ggggagccca agggcacgcc ctggcac                                              27

SEQ ID NO: 294         moltype = DNA   length = 28
FEATURE                Location/Qualifiers
source                 1..28
                       mol_type = other DNA
                       organism = synthetic construct
SEQUENCE: 294
ggcgtgccct tgggctcccc gggcgcgt                                             28

SEQ ID NO: 295         moltype = DNA   length = 27
FEATURE                Location/Qualifiers
source                 1..27
                       mol_type = other DNA
                       organism = synthetic construct
SEQUENCE: 295
ggggagccca agggcacgcc ctggcac                                              27

SEQ ID NO: 296         moltype = DNA   length = 33
FEATURE                Location/Qualifiers
source                 1..33
                       mol_type = other DNA
                       organism = synthetic construct
SEQUENCE: 296
tggggtaacc tttgagttct ctcagttggg ggc                                       33

SEQ ID NO: 297         moltype = DNA   length = 34
FEATURE                Location/Qualifiers
source                 1..34
                       mol_type = other DNA
```

-continued

```
                         organism = synthetic construct
SEQUENCE: 297
actgagagaa ctcaaaggtt accccagttg gggc                                    34

SEQ ID NO: 298          moltype = DNA  length = 33
FEATURE                 Location/Qualifiers
source                  1..33
                        mol_type = other DNA
                        organism = synthetic construct
SEQUENCE: 298
tggggtaacc tttgagttct ctcagttggg ggc                                     33

SEQ ID NO: 299          moltype = DNA  length = 34
FEATURE                 Location/Qualifiers
source                  1..34
                        mol_type = other DNA
                        organism = synthetic construct
SEQUENCE: 299
actgagagaa ctcaaaggtt accccagttg gggc                                    34

SEQ ID NO: 300          moltype = DNA  length = 33
FEATURE                 Location/Qualifiers
source                  1..33
                        mol_type = other DNA
                        organism = synthetic construct
SEQUENCE: 300
tggggtaacc tttgagttct ctcagttggg ggc                                     33

SEQ ID NO: 301          moltype = DNA  length = 34
FEATURE                 Location/Qualifiers
source                  1..34
                        mol_type = other DNA
                        organism = synthetic construct
SEQUENCE: 301
actgagagaa ctcaaaggtt accccagttg gggc                                    34

SEQ ID NO: 302          moltype = DNA  length = 27
FEATURE                 Location/Qualifiers
source                  1..27
                        mol_type = other DNA
                        organism = synthetic construct
SEQUENCE: 302
ggggagccca agggcacgcc ctggcac                                            27

SEQ ID NO: 303          moltype = DNA  length = 28
FEATURE                 Location/Qualifiers
source                  1..28
                        mol_type = other DNA
                        organism = synthetic construct
SEQUENCE: 303
ggcgtgccct tgggctcccc gggcgcgt                                           28

SEQ ID NO: 304          moltype = DNA  length = 27
FEATURE                 Location/Qualifiers
source                  1..27
                        mol_type = other DNA
                        organism = synthetic construct
SEQUENCE: 304
ggggagccca agggcacgcc ctggcac                                            27

SEQ ID NO: 305          moltype = DNA  length = 28
FEATURE                 Location/Qualifiers
source                  1..28
                        mol_type = other DNA
                        organism = synthetic construct
SEQUENCE: 305
ggcgtgccct tgggctcccc gggcgcgt                                           28

SEQ ID NO: 306          moltype = DNA  length = 33
FEATURE                 Location/Qualifiers
source                  1..33
                        mol_type = other DNA
                        organism = synthetic construct
SEQUENCE: 306
tggggtaacc tttgagttct ctcagttggg ggc                                     33

SEQ ID NO: 307          moltype = DNA  length = 34
FEATURE                 Location/Qualifiers
source                  1..34
```

```
                        mol_type = other DNA
                        organism = synthetic construct
SEQUENCE: 307
actgagagaa ctcaaaggtt accccagttg gggc                              34

SEQ ID NO: 308          moltype = DNA   length = 33
FEATURE                 Location/Qualifiers
source                  1..33
                        mol_type = other DNA
                        organism = synthetic construct
SEQUENCE: 308
tggggtaacc tttgagttct ctcagttggg ggc                               33

SEQ ID NO: 309          moltype = DNA   length = 34
FEATURE                 Location/Qualifiers
source                  1..34
                        mol_type = other DNA
                        organism = synthetic construct
SEQUENCE: 309
actgagagaa ctcaaaggtt accccagttg gggc                              34

SEQ ID NO: 310          moltype = DNA   length = 27
FEATURE                 Location/Qualifiers
source                  1..27
                        mol_type = other DNA
                        organism = synthetic construct
SEQUENCE: 310
ggggagccca agggcacgcc ctggcac                                      27

SEQ ID NO: 311          moltype = DNA   length = 28
FEATURE                 Location/Qualifiers
source                  1..28
                        mol_type = other DNA
                        organism = synthetic construct
SEQUENCE: 311
ggcgtgccct tgggctcccc gggcgcgt                                     28

SEQ ID NO: 312          moltype = DNA   length = 28
FEATURE                 Location/Qualifiers
source                  1..28
                        mol_type = other DNA
                        organism = synthetic construct
SEQUENCE: 312
ggcgtgccct tgggctcccc gggcgcgt                                     28

SEQ ID NO: 313          moltype = DNA   length = 27
FEATURE                 Location/Qualifiers
source                  1..27
                        mol_type = other DNA
                        organism = synthetic construct
SEQUENCE: 313
ggggagccca agggcacgcc ctggcac                                      27

SEQ ID NO: 314          moltype = DNA   length = 28
FEATURE                 Location/Qualifiers
source                  1..28
                        mol_type = other DNA
                        organism = synthetic construct
SEQUENCE: 314
ggcgtgccct tgggctcccc gggcgcgt                                     28

SEQ ID NO: 315          moltype = DNA   length = 27
FEATURE                 Location/Qualifiers
source                  1..27
                        mol_type = other DNA
                        organism = synthetic construct
SEQUENCE: 315
ggggagccca agggcacgcc ctggcac                                      27

SEQ ID NO: 316          moltype = DNA   length = 28
FEATURE                 Location/Qualifiers
source                  1..28
                        mol_type = other DNA
                        organism = synthetic construct
SEQUENCE: 316
ggcgtgccct tgggctcccc gggcgcgt                                     28

SEQ ID NO: 317          moltype = DNA   length = 33
FEATURE                 Location/Qualifiers
```

```
source                  1..33
                        mol_type = other DNA
                        organism = synthetic construct
SEQUENCE: 317
tggggtaacc tttgagttct ctcagttggg ggc                                33

SEQ ID NO: 318          moltype = DNA   length = 34
FEATURE                 Location/Qualifiers
source                  1..34
                        mol_type = other DNA
                        organism = synthetic construct
SEQUENCE: 318
actgagagaa ctcaaaggtt accccagttg gggc                               34

SEQ ID NO: 319          moltype = DNA   length = 34
FEATURE                 Location/Qualifiers
source                  1..34
                        mol_type = other DNA
                        organism = synthetic construct
SEQUENCE: 319
actgagagaa ctcaaaggtt accccagttg gggc                               34

SEQ ID NO: 320          moltype = DNA   length = 33
FEATURE                 Location/Qualifiers
source                  1..33
                        mol_type = other DNA
                        organism = synthetic construct
SEQUENCE: 320
tggggtaacc tttgagttct ctcagttggg ggc                                33

SEQ ID NO: 321          moltype = DNA   length = 34
FEATURE                 Location/Qualifiers
source                  1..34
                        mol_type = other DNA
                        organism = synthetic construct
SEQUENCE: 321
actgagagaa ctcaaaggtt accccagttg gggc                               34

SEQ ID NO: 322          moltype = DNA   length = 33
FEATURE                 Location/Qualifiers
source                  1..33
                        mol_type = other DNA
                        organism = synthetic construct
SEQUENCE: 322
tggggtaacc tttgagttct ctcagttggg ggc                                33

SEQ ID NO: 323          moltype = DNA   length = 34
FEATURE                 Location/Qualifiers
source                  1..34
                        mol_type = other DNA
                        organism = synthetic construct
SEQUENCE: 323
actgagagaa ctcaaaggtt accccagttg gggc                               34

SEQ ID NO: 324          moltype = DNA   length = 43
FEATURE                 Location/Qualifiers
source                  1..43
                        mol_type = other DNA
                        organism = synthetic construct
SEQUENCE: 324
taccgtacac cactgagacc gcggtggttg accagacaaa cct                     43

SEQ ID NO: 325          moltype = DNA   length = 44
FEATURE                 Location/Qualifiers
source                  1..44
                        mol_type = other DNA
                        organism = synthetic construct
SEQUENCE: 325
gtctggtcaa ccaccgcggt ctcagtggtg tacggtacaa acct                    44

SEQ ID NO: 326          moltype = DNA   length = 29
FEATURE                 Location/Qualifiers
source                  1..29
                        mol_type = other DNA
                        organism = synthetic construct
SEQUENCE: 326
acgacggcgg tctccgtcgt caggatcat                                     29

SEQ ID NO: 327          moltype = DNA   length = 29
```

```
FEATURE                 Location/Qualifiers
source                  1..29
                        mol_type = other DNA
                        organism = synthetic construct
SEQUENCE: 327
acgacggaga ccgccgtcgt cgacaagcc                                      29

SEQ ID NO: 328          moltype = DNA   length = 27
FEATURE                 Location/Qualifiers
source                  1..27
                        mol_type = other DNA
                        organism = synthetic construct
SEQUENCE: 328
cctacatgct cgaagggcgt atgcgcc                                        27

SEQ ID NO: 329          moltype = DNA   length = 26
FEATURE                 Location/Qualifiers
source                  1..26
                        mol_type = other DNA
                        organism = synthetic construct
SEQUENCE: 329
acgcccttcg agcatgtagg tcacgg                                         26

SEQ ID NO: 330          moltype = DNA   length = 13
FEATURE                 Location/Qualifiers
source                  1..13
                        mol_type = other DNA
                        organism = synthetic construct
SEQUENCE: 330
gggtttatca acc                                                       13

SEQ ID NO: 331          moltype = DNA   length = 13
FEATURE                 Location/Qualifiers
source                  1..13
                        mol_type = other DNA
                        organism = synthetic construct
SEQUENCE: 331
gtggagaaac tgg                                                       13

SEQ ID NO: 332          moltype = DNA   length = 13
FEATURE                 Location/Qualifiers
source                  1..13
                        mol_type = other DNA
                        organism = synthetic construct
SEQUENCE: 332
tgcgtcagtt tta                                                       13

SEQ ID NO: 333          moltype = DNA   length = 13
FEATURE                 Location/Qualifiers
source                  1..13
                        mol_type = other DNA
                        organism = synthetic construct
SEQUENCE: 333
gggaagtgta agg                                                       13

SEQ ID NO: 334          moltype = DNA   length = 13
FEATURE                 Location/Qualifiers
source                  1..13
                        mol_type = other DNA
                        organism = synthetic construct
SEQUENCE: 334
ggtgcgtttc act                                                       13

SEQ ID NO: 335          moltype = DNA   length = 13
FEATURE                 Location/Qualifiers
source                  1..13
                        mol_type = other DNA
                        organism = synthetic construct
SEQUENCE: 335
tcctctctgg ctc                                                       13

SEQ ID NO: 336          moltype = DNA   length = 13
FEATURE                 Location/Qualifiers
source                  1..13
                        mol_type = other DNA
                        organism = synthetic construct
SEQUENCE: 336
cccagaacct gag                                                       13
```

```
SEQ ID NO: 337        moltype = DNA   length = 13
FEATURE               Location/Qualifiers
source                1..13
                      mol_type = other DNA
                      organism = synthetic construct
SEQUENCE: 337
gggtttatca acc                                                            13

SEQ ID NO: 338        moltype = DNA   length = 13
FEATURE               Location/Qualifiers
source                1..13
                      mol_type = other DNA
                      organism = synthetic construct
SEQUENCE: 338
gtggagaaac tgg                                                            13

SEQ ID NO: 339        moltype = DNA   length = 13
FEATURE               Location/Qualifiers
source                1..13
                      mol_type = other DNA
                      organism = synthetic construct
SEQUENCE: 339
tgcgtcagtt tta                                                            13

SEQ ID NO: 340        moltype = DNA   length = 13
FEATURE               Location/Qualifiers
source                1..13
                      mol_type = other DNA
                      organism = synthetic construct
SEQUENCE: 340
gggaagtgta agg                                                            13

SEQ ID NO: 341        moltype = DNA   length = 13
FEATURE               Location/Qualifiers
source                1..13
                      mol_type = other DNA
                      organism = synthetic construct
SEQUENCE: 341
ggtgcgtttc act                                                            13

SEQ ID NO: 342        moltype = DNA   length = 13
FEATURE               Location/Qualifiers
source                1..13
                      mol_type = other DNA
                      organism = synthetic construct
SEQUENCE: 342
tcctctctgg ctc                                                            13

SEQ ID NO: 343        moltype = DNA   length = 13
FEATURE               Location/Qualifiers
source                1..13
                      mol_type = other DNA
                      organism = synthetic construct
SEQUENCE: 343
aggtttaatt aga                                                            13

SEQ ID NO: 344        moltype = DNA   length = 13
FEATURE               Location/Qualifiers
source                1..13
                      mol_type = other DNA
                      organism = synthetic construct
SEQUENCE: 344
gattaaatga ggc                                                            13

SEQ ID NO: 345        moltype = DNA   length = 13
FEATURE               Location/Qualifiers
source                1..13
                      mol_type = other DNA
                      organism = synthetic construct
SEQUENCE: 345
tctagagttt gct                                                            13

SEQ ID NO: 346        moltype = DNA   length = 13
FEATURE               Location/Qualifiers
source                1..13
                      mol_type = other DNA
                      organism = synthetic construct
SEQUENCE: 346
gtaacctggg gac                                                            13
```

```
SEQ ID NO: 347              moltype = DNA   length = 13
FEATURE                     Location/Qualifiers
source                      1..13
                            mol_type = other DNA
                            organism = synthetic construct SEQUENCE: 347
aggtttaatt aga                                                             13

SEQ ID NO: 348              moltype = DNA   length = 13
FEATURE                     Location/Qualifiers
source                      1..13
                            mol_type = other DNA
                            organism = synthetic construct SEQUENCE: 348
gattaaatga ggc                                                             13

SEQ ID NO: 349              moltype = DNA   length = 13
FEATURE                     Location/Qualifiers
source                      1..13
                            mol_type = other DNA
                            organism = synthetic construct SEQUENCE: 349
tctagagttt gct                                                             13

SEQ ID NO: 350              moltype = DNA   length = 13
FEATURE                     Location/Qualifiers
source                      1..13
                            mol_type = other DNA
                            organism = synthetic construct SEQUENCE: 350
gtaacctggg gac                                                             13

SEQ ID NO: 351              moltype = DNA   length = 13
FEATURE                     Location/Qualifiers
source                      1..13
                            mol_type = other DNA
                            organism = synthetic construct SEQUENCE: 351
actagagttg gtg                                                             13

SEQ ID NO: 352              moltype = DNA   length = 13
FEATURE                     Location/Qualifiers
source                      1..13
                            mol_type = other DNA
                            organism = synthetic construct SEQUENCE: 352
ataatcgaga agc                                                             13

SEQ ID NO: 353              moltype = DNA   length = 13
FEATURE                     Location/Qualifiers
source                      1..13
                            mol_type = other DNA
                            organism = synthetic construct SEQUENCE: 353
cagggcaacg ccc                                                             13

SEQ ID NO: 354              moltype = DNA   length = 13
FEATURE                     Location/Qualifiers
source                      1..13
                            mol_type = other DNA
                            organism = synthetic construct SEQUENCE: 354
ttttatacca ttt                                                             13

SEQ ID NO: 355              moltype = DNA   length = 13
FEATURE                     Location/Qualifiers
source                      1..13
                            mol_type = other DNA
                            organism = synthetic construct SEQUENCE: 355
gtgaatgact aag                                                             13

SEQ ID NO: 356              moltype = DNA   length = 13
FEATURE                     Location/Qualifiers
source                      1..13
                            mol_type = other DNA
                            organism = synthetic construct

SEQUENCE: 356
```
gcatccctac cag                                                                13

SEQ ID NO: 357          moltype = DNA   length = 13
FEATURE                 Location/Qualifiers
source                  1..13
                        mol_type = other DNA
                        organism = synthetic construct SEQUENCE: 357
gctacacttt ggt                                                                13

SEQ ID NO: 358          moltype = DNA   length = 13
FEATURE                 Location/Qualifiers
source                  1..13
                        mol_type = other DNA
                        organism = synthetic construct SEQUENCE: 358
actagagttg gtg                                                                13

SEQ ID NO: 359          moltype = DNA   length = 13
FEATURE                 Location/Qualifiers
source                  1..13
                        mol_type = other DNA
                        organism = synthetic construct SEQUENCE: 359
ataatcgaga agc                                                                13

SEQ ID NO: 360          moltype = DNA   length = 13
FEATURE                 Location/Qualifiers
source                  1..13
                        mol_type = other DNA
                        organism = synthetic construct SEQUENCE: 360
cagggcaacg ccc                                                                13

SEQ ID NO: 361          moltype = DNA   length = 13
FEATURE                 Location/Qualifiers
source                  1..13
                        mol_type = other DNA
                        organism = synthetic construct SEQUENCE: 361
tttttatacca ttt                                                               13

SEQ ID NO: 362          moltype = DNA   length = 13
FEATURE                 Location/Qualifiers
source                  1..13
                        mol_type = other DNA
                        organism = synthetic construct SEQUENCE: 362
gtgaatgact aag                                                                13

SEQ ID NO: 363          moltype = DNA   length = 13
FEATURE                 Location/Qualifiers
source                  1..13
                        mol_type = other DNA
                        organism = synthetic construct SEQUENCE: 363
gcatccctac cag                                                                13

SEQ ID NO: 364          moltype = DNA   length = 13
FEATURE                 Location/Qualifiers
source                  1..13
                        mol_type = other DNA
                        organism = synthetic construct SEQUENCE: 364
gctacacttt ggt                                                                13

SEQ ID NO: 365          moltype = DNA   length = 13
FEATURE                 Location/Qualifiers
source                  1..13
                        mol_type = other DNA
                        organism = synthetic construct SEQUENCE: 365
gcatccctac cag                                                                13

SEQ ID NO: 366          moltype = DNA   length = 13
FEATURE                 Location/Qualifiers
source                  1..13
                        mol_type = other DNA
                        organism = synthetic construct

```
SEQUENCE: 366
gctacacttt ggt                                                                    13

SEQ ID NO: 367          moltype = DNA  length = 13
FEATURE                 Location/Qualifiers
source                  1..13
                        mol_type = other DNA
                        organism = synthetic construct
SEQUENCE: 367
gcatccctac cag                                                                    13

SEQ ID NO: 368          moltype = DNA  length = 13
FEATURE                 Location/Qualifiers
source                  1..13
                        mol_type = other DNA
                        organism = synthetic construct
SEQUENCE: 368
gctacacttt ggt                                                                    13

SEQ ID NO: 369          moltype = DNA  length = 13
FEATURE                 Location/Qualifiers
source                  1..13
                        mol_type = other DNA
                        organism = synthetic construct
SEQUENCE: 369
gcatccctac cag                                                                    13

SEQ ID NO: 370          moltype = DNA  length = 13
FEATURE                 Location/Qualifiers
source                  1..13
                        mol_type = other DNA
                        organism = synthetic construct
SEQUENCE: 370
gctacacttt ggt                                                                    13

SEQ ID NO: 371          moltype = DNA  length = 86
FEATURE                 Location/Qualifiers
source                  1..86
                        mol_type = other DNA
                        organism = synthetic construct
SEQUENCE: 371
gtttaagagc taagctggaa acagcatagc aagtttaaat aaggctagtc cgttatcaac  60
tcgaaagagt ggcaccgagt cggtgc                                      86

SEQ ID NO: 372          moltype = DNA  length = 37
FEATURE                 Location/Qualifiers
source                  1..37
                        mol_type = other DNA
                        organism = synthetic construct
SEQUENCE: 372
cgcggttcta tctagttacg cgttaaacca actagaa                                          37
```